US009475845B2

(12) United States Patent
Asokan et al.

(10) Patent No.: US 9,475,845 B2
(45) Date of Patent: Oct. 25, 2016

(54) MODIFIED VIRUS VECTORS AND METHODS OF MAKING AND USING THE SAME

(71) Applicant: The University of North Carolina at Chapel Hill, Chapel Hill, NC (US)

(72) Inventors: Aravind Asokan, Chapel Hill, NC (US); Richard Jude Samulski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/543,459

(22) Filed: Nov. 17, 2014

(65) Prior Publication Data

US 2015/0152142 A1 Jun. 4, 2015

Related U.S. Application Data

(63) Continuation of application No. 13/201,154, filed as application No. PCT/US2010/023885 on Feb. 11, 2010, now Pat. No. 8,889,641.

(60) Provisional application No. 61/151,736, filed on Feb. 11, 2009.

(51) Int. Cl.
*C07K 14/005* (2006.01)
*C12N 15/86* (2006.01)

(52) U.S. Cl.
CPC ............ *C07K 14/005* (2013.01); *C12N 15/86* (2013.01); *C12N 2750/14122* (2013.01); *C12N 2750/14143* (2013.01); *C12N 2750/14145* (2013.01); *C12N 2810/6027* (2013.01)

(58) Field of Classification Search
None
See application file for complete search history.

(56) References Cited

U.S. PATENT DOCUMENTS

| 5,139,941 A | 8/1992 | Muzyczka et al. |
| 5,436,146 A | 7/1995 | Shenk et al. |
| 5,478,745 A | 12/1995 | Samulski et al. |
| 5,589,377 A | 12/1996 | Lebkowski et al. |
| 5,622,856 A | 4/1997 | Natsoulis |
| 5,658,785 A | 8/1997 | Johnson |
| 5,681,731 A | 10/1997 | Lebkowski et al. |
| 5,753,500 A | 5/1998 | Shenk et al. |
| 5,756,283 A | 5/1998 | Wilson et al. |
| 5,773,289 A | 6/1998 | Samulski et al. |
| 5,780,280 A | 7/1998 | Lebkowski et al. |
| 5,780,447 A | 7/1998 | Nienhuis |
| 5,786,211 A | 7/1998 | Johnson |
| 5,834,441 A | 11/1998 | Philip et al. |
| 5,843,742 A | 12/1998 | Natsoulis et al. |
| 5,846,528 A | 12/1998 | Podsakoff et al. |
| 5,846,546 A | 12/1998 | Hurwitz et al. |
| 5,856,152 A | 1/1999 | Wilson et al. |
| 5,858,351 A | 1/1999 | Podsakoff et al. |
| 5,858,775 A | 1/1999 | Johnson |
| 5,861,171 A | 1/1999 | Philip et al. |
| 5,861,314 A | 1/1999 | Philip et al. |
| 5,863,541 A | 1/1999 | Samulski et al. |
| 5,866,552 A | 2/1999 | Wilson et al. |
| 5,866,696 A | 2/1999 | Carter et al. |
| 5,869,305 A | 2/1999 | Samulski et al. |
| 5,871,982 A | 2/1999 | Wilson et al. |
| 5,872,005 A | 2/1999 | Wang et al. |
| 5,874,304 A | 2/1999 | Zolotukhin et al. |
| 5,874,556 A | 2/1999 | Lupton et al. |
| 5,882,652 A | 3/1999 | Valdes et al. |
| 5,905,040 A | 5/1999 | Mazzara et al. |
| 5,916,563 A | 6/1999 | Young et al. |
| 5,922,315 A | 7/1999 | Roy |
| 5,945,335 A | 8/1999 | Colosi |
| 5,952,221 A | 9/1999 | Kurtzman et al. |
| 5,962,274 A | 10/1999 | Parks |
| 5,962,313 A | 10/1999 | Podsakoff et al. |
| 6,001,371 A | 12/1999 | Young et al. |
| 6,156,303 A | 12/2000 | Russell et al. |
| 6,268,213 B1 * | 7/2001 | Samulski ............... C12N 15/86 435/235.1 |
| 6,410,300 B1 | 6/2002 | Samulski et al. |
| 6,468,524 B1 | 10/2002 | Chiorini et al. |
| 6,468,771 B1 | 10/2002 | Einerhand et al. |

(Continued)

FOREIGN PATENT DOCUMENTS

AU 762220 6/2003
EP WO 2008/145401 A2 * 12/2008

(Continued)

OTHER PUBLICATIONS

Agbandje et al. "Structure Determination of Feline Panleukopenia Virus Empty Particles" *Proteins: Structure, Function, and Genetics* 16:155-171 (1993).
Alexander et al. "Transfer of Contaminants in Adeno-Associated Virus Vector Stocks Can Mimic Transduction and Lead to Artifactual Results" *Human Gene Therapy* 8:1911-1920 (1997).
Anderson, French "Human gene therapy" *Nature* 392(Supp):25-30 (1998).
Antonietti et al. "Characterization of the Cell Type-Specific Determinant in the Genome of Minute Virus of Mice" *Journal of Virology* 62(2):552-557 (1988).
Asokan et al. "AAV does the shuffle" *Nature Biotechnology* 24(2):158-160 (2006).

(Continued)

*Primary Examiner* — Stacy B Chen
(74) *Attorney, Agent, or Firm* — Myers Bigel & Sibley, P.A.

(57) ABSTRACT

The present invention provides AAV capsid proteins (VP1, VP2 and/or VP3) comprising a modification in the amino acid sequence in the three-fold axis loop 4 and virus capsids and virus vectors comprising the modified AAV capsid protein. In particular embodiments, the modification comprises a substitution of one or more amino acids at amino acid positions 585 to 590 (inclusive) of the native AAV2 capsid protein sequence or the corresponding positions of other AAV capsid proteins. The invention also provides methods of administering the virus vectors and virus capsids of the invention to a cell or to a subject in vivo.

8 Claims, 11 Drawing Sheets

(56) References Cited

U.S. PATENT DOCUMENTS

| | | |
|---|---|---|
| 6,491,907 B1 | 12/2002 | Rabinowitz et al. |
| 6,703,237 B2 | 3/2004 | Samulski et al. |
| 6,759,237 B1 | 7/2004 | Wilson et al. |
| 6,984,517 B1 | 1/2006 | Chiorini et al. |
| 7,172,893 B2 | 2/2007 | Rabinowitz et al. |
| 7,252,997 B1 | 8/2007 | Hallek et al. |
| 7,259,151 B2 | 8/2007 | Arbetman et al. |
| 7,285,381 B1 | 10/2007 | Hallek et al. |
| 7,314,912 B1 | 1/2008 | Hallek et al. |
| 2002/0192823 A1 | 12/2002 | Bartlett |
| 2003/0053990 A1 | 3/2003 | Rabinowitz et al. |
| 2003/0215422 A1 | 11/2003 | Chiorini et al. |
| 2004/0057931 A1 | 3/2004 | Wilson et al. |
| 2004/0057932 A1 | 3/2004 | Wilson et al. |
| 2004/0057933 A1 | 3/2004 | Wilson et al. |
| 2004/0086490 A1 | 5/2004 | Chiorini et al. |
| 2005/0106558 A1 | 5/2005 | Perabo et al. |
| 2005/0255089 A1 | 11/2005 | Chiorini et al. |
| 2005/0287122 A1 | 12/2005 | Bartlett et al. |
| 2006/0088936 A1 | 4/2006 | Warrington et al. |
| 2006/0188483 A1 | 8/2006 | Rabinowitz et al. |
| 2006/0188484 A1 | 8/2006 | Rabinowitz et al. |
| 2007/0036757 A1 | 2/2007 | Kleinschmidt et al. |
| 2007/0036760 A1 | 2/2007 | Wilson et al. |
| 2007/0196338 A1 | 8/2007 | Samulski et al. |
| 2007/0238684 A1 | 10/2007 | Hallek et al. |
| 2007/0286870 A1 | 12/2007 | Modrow et al. |
| 2008/0064081 A1 | 3/2008 | Hallek et al. |
| 2008/0269149 A1 | 10/2008 | Bowles et al. |
| 2009/0215879 A1 | 8/2009 | DiPrimio et al. |

FOREIGN PATENT DOCUMENTS

| | | |
|---|---|---|
| WO | WO 95/28493 A1 | 10/1995 |
| WO | WO 9600587 A1 | 1/1996 |
| WO | WO 96/36364 A1 | 11/1996 |
| WO | WO 97/05266 A1 | 2/1997 |
| WO | WO 97/38723 A1 | 10/1997 |
| WO | WO 98/09524 A1 | 3/1998 |
| WO | WO 98/11244 A2 | 3/1998 |
| WO | WO 98/32842 A1 | 7/1998 |
| WO | WO 98/41240 A1 | 9/1998 |
| WO | WO 99/61601 A2 | 12/1999 |
| WO | WO 99/67393 A2 | 12/1999 |
| WO | WO 00/28004 A1 | 5/2000 |
| WO | WO 00/28061 A2 | 5/2000 |
| WO | WO 01/05990 A1 | 1/2001 |
| WO | WO 01/05991 A1 | 1/2001 |
| WO | WO 01/68888 A2 | 9/2001 |
| WO | WO 01/83692 A2 | 11/2001 |
| WO | WO 2004/111248 A2 | 12/2004 |
| WO | WO 2005/005610 A2 | 1/2005 |
| WO | WO 2005/106046 A1 | 11/2005 |
| WO | WO 2006/066066 A2 | 6/2006 |
| WO | WO 2007/089632 A2 | 8/2007 |
| WO | WO 2008/145400 A1 * | 12/2008 |
| WO | WO 2009/108274 A2 | 9/2009 |
| WO | WO 2009/137006 A2 | 11/2009 |

OTHER PUBLICATIONS

Asokan, Aravind "Rational Engineering of Chimeric AAV Vectors with Altered Tissue Tropism" *Oral Presentation* Cold Spring Harbor, New York:18 pages (Nov. 27, 2007).

Asokan, Aravind "Engineering Synthetic Parvoviral Capsids with Atypical Tissue Tropisms" *Gordon Conference Presentation* 1 page (Feb. 15, 2009).

Asokan et al. "Reengineering a receptor footprint of adeno-associated virus enables selective and systemic gene transfer to muscle" *Nature Biotechnology* 28(1):79-83 (2010).

Ball-Goodrich et al. "Two Amino Acid Substitutions within the Capsid Are Coordinately Required for Acquisition of Fibrotropism by the Lymphotropic Strain of Minute Virus of Mice" *Journal of Virology* 66(6):3415-3423 (1992).

Bartlett et al. "Genetics and Biology of Adeno-Associated Virus" *Viral Vectors* Chapter 4:55-73 (1995).

Benedetti et al. "Repair or replace? Exploiting novel gene and cell therapy strategies for muscular dystrophies" *FEBS Journal* 280:4263-4280 (2013).

Bloom et al. "Characterization of Chimeric Full-Length Molecular Clones of Aleutian Mink Disease Parvovirus (ADV): Identification of a Determinant Governing Replication of ADV in Cell Culture" *Journal of Virology* 67(10):5976-5988 (1993).

Bowles et al. "Marker Rescue of Adeno-Associated Virus (AAV) Capsid Mutants: a Novel Approach for Chimeric AAV Production" *Journal of Virology* 77(1):423-432 (2003).

Brown et al. "Chimeric Parvovirus B19 Capsids for the Presentation of Foreign Epitopes" *Virology* 198:477-488 (1994).

Burger et al. "Recombinant AAV Viral Vectors Pseudotyped with Viral Capsids from Serotypes 1, 2, and 5 Display Differential Efficiency and Cell Tropism after Delivery to Different Regions of the Central Nervous System" *Molecular Therapy* 10(2):302-317 (2004).

Chang et al. "Multiple Amino Acids in the Capsid Structure of Canine Parvovirus Coordinately Determine the Canine Host Range and Specific Antigenic and Hemagglutination Properties" *Journal of Virology* 66(12):6858-6867 (1992).

Chapman et al. "Structure, Sequence, and Function Correlations among Parvoviruses" *Virology* 194(2):491-508 (1993).

Chen et al. "Molecular Characterization of Adeno-Associated Viruses Infecting Children" *Journal of Virology* 79(23):14781-14792 (2005).

Chiorini et al. "Cloning of Adeno-Associated Virus Type 4 (AAV4) and Generation of Recombinant AAV4 Particles" *Journal of Virology* 71(9):6823-6833 (1997).

Chiorini et al. "Adeno-Associated Virus (AAV) Type 5 Rep Protein Cleaves a Unique Terminal Resolution Site Compared with Other AAV Serotypes" *Journal of Virology* 73(5):4293-4298 (1999).

Chiorini et al. "Cloning and Characterization of Adeno-Associated Virus Type 5" *Journal of Virology* 73(2):1309-1319 (1999).

Conway et al. "Recombinant Adeno-Associated Virus Type 2 Replication and Packaging Is Entirely Supported by a Herpes Simplex Virus Type 1 Amplicon Expressing Rep and Cap" *Journal of Virology* 71(11):8780-8789 (1997).

Dang et al. "Gene Therapy and Translational Cancer Research" *Clinical Cancer Research* 5:471-474 (1999).

Diprimio et al. "Surface Loop Dynamics in Adeno-Associated Virus Capsid Assembly" *Journal of Virology* 82(11):5178-5189 (2008).

Douar et al. "Deleterious effect of peptide insertions in a permissive site of the AAV2 capsid" *Virology* 309:203-208 (2003).

Du et al. "Differential Myocardial Gene Delivery by Recombinant Serotype-Specific Adeno-associated Viral Vectors" *Molecular Therapy* 10(3):604-608 (2004).

Duan, Dongsheng "Duchenne muscular dystrophy gene therapy: Lost in translation?" *Research and Reports in Biology* 2:31-42 (2011).

Extended European Search Report corresponding to European Patent Application No. 10741720.6; 11 pages (May 17, 2013).

European Medicines Agency "European Medicines Agency recommends first gene therapy for approval" http://www.ema.europa.eu 2 pages (Jul. 20, 2012).

Fang et al. "Stable antibody expression at therapeutic levels using the 2A peptide" *Nature Biotechnology* 23(5):584-590 (2005).

Faust et al. "Universal Purification of AAV Serotypes 1-5 Modified to Contain a Heparin Binding Epitope" *Molecular Therapy* 9(Supplement 1):S36 (2004).

Fu et al. "Viral sequences enable efficient and tissue-specific expressions of transgenes in *Xenopus*" *Nature Biotechnology* 16:253-257 (1998).

Gao et al. "High-Titer Adeno-Associated Viral Vectors from a Rep/Cap Cell Line and Hybrid Shuttle Virus" *Human Gene Therapy* 9:2353-2362 (1998).

Gao et al. "Novel adeno-associated viruses from rhesus monkeys as vectors for human gene therapy" *Proceedings of the National Academy of Sciences* 99(18):11854-11859 (2002).

(56) References Cited

OTHER PUBLICATIONS

Gao et al. "Clades of Adeno-Associated Viruses Are Widely Disseminated in Human Tissues" *Journal of Virology* 78(12):6381-6388 (2004).
Gardiner et al. "Mapping of the Fibrotropic and Lymphotropic Host Range Determinants of the Parvovirus Minute Virus of Mice" *Journal of Virology* 62(8):2605-2613 (1988).
Girod et al. "Genetic capsid modifications allow efficient re-targeting of adeno-associated virus type 2" *Nature Medicine* 5(9):1052-1056 (1999).
Goldman et al. "Targeted Gene Delivery to Kaposi's Sarcoma Cells via the Fibroblast Growth Factor Receptor" *Cancer Research* 57:1447-1451 (1997).
Grifman et al. "Incorporation of Tumor-Targeting Peptides into Recombinant Adeno-associated Virus Capsids" *Molecular Therapy* 3(6):964-975 (2001).
Grimm et al. "Preclinical in vivo evaluation of pseudotyped adeno-associated virus vectors for liver gene therapy" *Blood* 102(7):2412-2419 (2003).
Halbert et al. "Adeno-Associated Virus Type 6 (AAV6) Vectors Mediate Efficient Transduction of Airway Epithelial Cells in Mouse Lungs Compared to That of AAV2 Vectors" *Journal of Virology* 75(14):6615-6624 (2001).
Hauck et al. "Characterization of Tissue Tropism Determinants of Adeno-Associated Virus Type 1" *Journal of Virology* 77(4):2768-2774 (2003).
Hermonat et al. "Genetics of Adeno-Associated Virus: Isolation and Preliminary Characterization of Adeno-Associated Virus Type 2 Mutants" *Journal of Virology* 51(2):329-339 (1984).
Hodgson, Clague "Advances in vector systems for gene therapy" *Expert Opinion on Therapeutic Patents* 5(5):459-468 (1995).
Horiuchi et al. "Mapping of determinants of the host range for canine cells in the genome of canine parvovirus using canine parvovirus/mink enteritis virus chimeric viruses" *Journal of General Virology* 75:1319-1328 (1994).
International Preliminary Report on Patentability corresponding to International Patent Application no. PCT/US2010/023885; 7 pages (Aug. 16, 2011).
International Search Report corresponding to International Patent Application No. PCT/US2010/023885; 10 pages (Oct. 15, 2010).
Jooss et al. "Transduction of Dendritic Cells by DNA Viral Vectors Directs the Immune Response to Transgene Products in Muscle Fibers" *Journal of Virology* 72(5):4212-4223 (1998).
Juengst, Eric "What next for human gene therapy?" *British Medical Journal* 326:1410-1411 (2003).
Kay et al. "Viral vectors for gene therapy: the art of turning infectious agents into vehicles of therapeutics" *Nature Medicine* 7(1):33-40 (2001).
Kern et al. "Identification of a Heparin-Binding Motif on Adeno-Associated Virus Type 2 Capsids" *Journal of Virology* 77(20):11072-11081 (2003).
Levy et al. "Heparin binding induces conformational changes in Adeno-associated virus serotype 2" *Journal of Structural Biology* 165:146-156 (2009).
Li et al. "Role for Highly Regulated *rep* Gene Expression in Adeno-Associated Virus Vector Production" *Journal of Virology* 71(7): 5236-5243 (1997).
Li et al. "Engineering and Selection of Shuffled AAV Genomes: A New Strategy for Producing Targeted Biological Nanoparticles" *Molecular Therapy* 16(7):1252-1260 (2008).
Lieber, André "AAV display—homing in on the target" *Nature Biotechnology* 21(9):1011-1013 (2003).
"Limb-girdle muscular dystrophy" *Genetics Home Reference* http://ghr.nlm.nih.gov/condition/limb-girdle-muscular-dystrophy/show/print pp. 1-17 (Jan. 29, 2014).
Llamas-Saiz et al. "Structure Determination of Minute Virus of Mice" *Acta Crystallographica* D53:93-102 (1997).
Lochrie et al. "Mutations on the External Surfaces of Adeno-Associated Virus Type 2 Capsids That Affect Transduction and Neutralization" *Journal of Virology* 80(2):821-834 (2006).

Maheshri et al. "Directed evolution of adeno-associated virus yields enhanced gene delivery vectors" *Nature Biotechnology* 24(2):198-204 (2006).
Marshall, Eliot "Gene Therapy's Growing Pains" *Science* 269:1050-1055 (1995).
Maxwell et al. "Targeting a Feline Parvovirus to Human Tumor Cells" *Abstracts of Papers Presented at the 1999 Meeting on Vector Targeting Strategies for Therapeutic Gene Delivery* p. 87 (1999) (Abstract Only).
McCarty et al. "Integration of Adeno-Associated Virus (AAV) and Recombinant AAV Vectors" *Annual Review of Genetics* 38:819-845 (2004).
Miyamura et al. "Parvovirus particles as platforms for protein presentation" *Proceedings of the National Academy of Sciences* 91:8507-8511 (1994).
Moskalenko et al. "Epitope Mapping of Human Anti-Adeno-Associated Virus Type 2 Neutralizing Antibodies: Implications for Gene Therapy and Virus Structure" *Journal of Virology* 74(4):1761-1766 (2000).
Muller et al. "Random peptide libraries displayed on adeno-associated virus to select for targeted gene therapy vectors" *Nature Biotechnology* 21(9):1040-1046 (2003).
Muller et al. "Improved cardiac gene transfer by transcriptional and transductional targeting of adeno-associated viral vectors" *Cardiovascular Research* 70:70-78 (2006).
Muralidhar et al. "Site-Directed Mutagenesis of Adeno-Associated Virus Type 2 Structural Protein Initiation Codons: Effects on Regulation of Synthesis and Biological Activity" *Journal of Virology* 68(1):170-176 (1994).
Muramatsu et al. "Nucleotide Sequencing and Generation of an Infectious Clone of Adeno-Associated Virus 3" *Virology* 221:208-217 (1996).
Nam et al. "Structure of Adeno-Associated Virus Serotype 8, a Gene Therapy Vector" *Journal of Virology* 81(22):12260-12271 (2007).
Nathwani et al. "Adenovirus-Associated Virus Vector-Mediated Gene Transfer in Hemophilia B" *The New England Journal of Medicine* 10.1056/NEJMoa1108046:1-9 (2011).
Opie et al. "Identification of Amino Acid Residues in the Capsid Proteins of Adeno-Associated Virus Type 2 That Contribute to Heparan Sulfate Proteoglycan Binding" *Journal of Virology* 77(12):6995-7006 (2003).
Padron et al. "Structure of Adeno-Associated Virus Type 4" *Journal of Virology* 79(8):5047-5058 (2005).
Parrish et al. "Canine Host Range and a Specific Epitope Map along with Variant Sequences is the Capsid Protein Gene of Canine Parvovirus and Related Feline, Mink, and Raccoon Parvoviruses" *Virology* 166:293-307 (1988).
Parrish et al. "Rapid Antigenic-Type Replacement and DNA Sequence Evolution of Canine Parvovirus" *Journal of Virology* 65(12):6544-6552 (1991).
Patil et al. "DNA-based Therapeutics and DNA Delivery Systems: A Comprehensive Review" *The AAPS Journal* 7(1):E61-E77 (2005).
Perabo et al. "Heparan Sulfate Proteoglycan Binding Properties of Adeno-Associated Virus Retargeting Mutants and Consequences for Their In Vivo Tropism" *Journal of Virology* 80(14):7265-7269 (2006).
Petrs-Silva et al. "High-efficiency Transduction of the Mouse Retina by Tyrosine-mutant AAV Serotype Vectors" *Molecular Therapy* 17(3):463-471 (2009).
Phillips et al. "Systemic Gene Transfer to Skeletal Muscle Using Reengineered AAV Vectors" *Methods in Molecular Biology* 709:141-151 (2011).
Ponnazhagan et al. "Recombinant Human Parvovirus B19 Vectors: Erythroid Cell-Specific Delivery and Expression of Transduced Genes" *Journal of Virology* 72(6):5224-5230 (1998).
Raake et al. "Cardio-specific long-term gene expression in a porcine model after selective pressure-regulated retroinfusion of adeno-associated viral (AAV) vectors" *Gene Therapy* 15:12-17 (2008).
Rabinowitz et al. "Adeno-associated virus expression systems for gene transfer" *Current Opinion in Biotechnology* 9:470-475 (1998).
Rabinowitz et al. "Insertional Mutagenesis of AAV2 Capsid and the Production of Recombinant Virus" *Virology* 265:274-285 (1999).

(56) References Cited

OTHER PUBLICATIONS

Rabinowitz et al. "Targeted Adeno-Associated Virus" *Abstracts of papers presented at the 1999 meeting on Vector Targeting Strategies for Therapeutic Gene Delivery* 2 pages (1999) (Abstract Only).
Rabinowitz et al. "Cross-Dressing the Virion: the Transcapsidation of Adeno-Associated Virus Serotypes Functionally Defines Subgroups" *Journal of Virology* 78(9):4421-4432 (2004).
Rodino-Klapac et al. "Gene Therapy for Duchenne Muscular Dystrophy" *Archives of Neurology* 64(9):1236-1241 (2007).
Romano et al. "Latest Developments in Gene Transfer Technology: Achievements, Perspectives, and Controversies over Therapeutic Applications" *Stem Cells* 18:19-39 (2000).
Rotundo et al. "Use of a Lower Dosage Liver-Detargeted AAV Vector to Prevent Hamster Muscular Dystrophy" *Human Gene Therapy* 24:1-7 (2013).
Ruffing et al. "Mutations in the carboxy terminus of adeno-associated virus 2 capsid proteins affect viral infectivity: lack of an RGD integrin-binding motif" *Journal of General Virology* 75:3385-3392 (1994).
Rutledge et al. "Infectious Clones and Vectors Derived from Adeno-Associated Virus (AAV) Serotypes Other Than AAV Type 2" *Journal of Virology* 72:309-319 (1998).
Schnepp et al. "Characterization of Adeno-Associated Virus Genomes Isolated from Human Tissues" *Journal of Virology* 79(23):14793-14803 (2005).
Schnepp et al. "Infectious Molecular Clones of Adeno-Associated Virus Isolated Directly from Human Tissues" *Journal of Virology* 83(3):1456-1464 (2009).
Sedlik et al. "Recombinant parvovirus-like particles as an antigen carrier: A novel nonreplicative exogenous antigen to elicit protective antiviral cytotoxic T cells" *Proceedings of the National Academy of Sciences* 94:7503-7508 (1997).
Shen et al. "Characterization of the Relationship of AAV Capsid Domain Swapping to Liver Transduction Efficiency" *Molecular Therapy* 15(11):1955-1962 (2007).
Shi et al. "Insertional Mutagenesis at Positions 520 and 584 of Adeno-Associated Virus Type 2 (AAV2) Capsid Gene and Generation of AAV2 Vectors with Eliminated Heparin-Binding Ability and Introduced Novel Tropism" *Human Gene Therapy* 17:353-361 (2006).
Simpson et al. "The structure of an insect parvovirus (*Galleria mellonella* densovirus) at 3.7 Å resolution" *Structure* 6(11):1355-1367, (1998).
Smuda et al. "Adeno-Associated Viruses Having Nonsense Mutations in the Capsid Genes: Growth in Mammalian Cells Containing an Inducible Amber Suppressor" *Virology* 184:310-318 (1991).
Spitzer et al. "Species specificity for transduction of cultured cells by a recombinant LuIII rodent parvovirus genome encapsidated by canine parvovirus or feline panleukopenia virus" *Journal of General Virology* 77:1787-1792 (1996).
Spitzer et al. "Tropic determinant for canine parvovirus and feline panleukopenia virus functions through the capsid protein VP2" *Journal of General Virology* 78:925-928 (1997).
Srivastava et al. "Construction of a recombinant human parvovirus B19: Adeno-associated virus 2 (AAV) DNA inverted terminal repeats are functional in an AAV-B19 hybrid virus" *Proceedings of the National Academy of Sciences* 86:8078-8082 (1989).
Trent et al. "Genetic and Cellular Therapies" *Molecular Med: An Introductory Text* Chapter 6:143-173 (2005).
Tsao et al. "The Three-Dimensional Structure of Canine Parvovirus and Its Functional Implications" *Science* 251(5000):1456-1464 (1991).
Urabe et al. "Insect Cells as a Factory to Produce Adeno-Associated Virus Type 2 Vectors" *Human Gene Therapy* 13:1935-1943 (2002).
Vandenberghe et al. "Heparin binding directs activation of T cells against adeno-associated virus serotype 2 capsid" *Nature Medicine* 12(8):967-971 (2006).
Verma et al. "Gene therapy—promises, problems and prospects" *Nature* 389:239-242 (1997).
Wang et al. "Rescue and Replication of Adeno-Associated Virus Type 2 as well as Vector DNA Sequences from Recombinant Plasmids Containing Deletions in the Viral Inverted Terminal Repeats: Selective Encapsidation of Viral Genomes in Progeny Virions" *Journal of Virology* 70(3):1668-1677 (1996).
Wang et al. "Recombinant AAV serotype 1 transduction efficiency and tropism in the murine brain" *Gene Therapy* 10:1528-1534 (2003).
Warrington et al. "Adeno-Associated Virus Type 2 VP2 Capsid Protein Is Nonessential and Can Tolerate Large Peptide Insertions at Its N Terminus" *Journal of Virology* 78(12):6595-6609 (2004).
Wu et al. "The Canine Parvovirus Empty Capsid Structure" *Journal of Molecular Biology* 233:231-244 (1993).
Wu et al. "Mutational Analysis of the Adeno-Associated Virus Type 2 (AAV2) Capsid Gene and Construction of AAV2 Vectors with Altered Tropism" *Journal of Virology* 74(18):8635-8647 (2000).
Wu et al. "Single Amino Acid Changes Can Influence Titer, Heparin Binding, and Tissue Tropism in Different Adeno-Associated Virus Serotypes" *Journal of Virology* 80(22):11393-11397 (2006).
Xiao et al. "Efficient Long-Term Gene Transfer into Muscle Tissue of Immunocompetent Mice by Adeno-Associated Virus Vector" *Journal of Virology* 70(11):8098-8108 (1996).
Xiao et al. "Production of High-Titer Recombinant Adeno-Associated Virus Vectors in the Absence of Helper Adenovirus" *Journal of Virology* 72(3):2224-2232 (1998).
Xiao et al. "Gene Therapy Vectors Based on Adeno-Associated Virus Type 1" *Journal of Virology* 73(5):3994-4003 (1999).
Xie et al. "The atomic structure of adeno-associated virus (AAV-2), a vector for human gene therapy" *Proceedings of the National Academy of Sciences* 99(16):10405-10410 (2002).
Yang et al. "Development of Novel Cell Surface CD34-Targeted Recombinant Adenoassociated Virus Vectors for Gene Therapy" *Human Gene Therapy* 9:1929-1937 (1998).
Yang et al. "Virus-Mediated Transduction of Murine Retina with Adeno-Associated Virus: Effects of Viral Capsid and Genome Size" *Journal of Virology* 76(15):7651-7660 (2002).
Yang et al. "A myocardium tropic adeno-associated virus (AAV) evolved by DNA shuffling and in vivo selection" *Proceedings of the National Academy of Sciences* 106(10):3946-3951 (2009).
Zhong et al. "Next generation of adeno-associated virus 2 vectors: Point mutations in tyrosines lead to high-efficiency transduction at lower doses" *Proceedings of the National Academy of Sciences* 105(22):7827-7832 (2008).
Zhong et al. "Tyrosine phosphorylation of AAV2 vectors and its consequences on viral intracellular trafficking and transgene expression" *Virology* 381(2):194-202 (2008).
Zhou et al. "Evaluation of Novel Gene Transfer Vectors Derived from Infectious Molecular Clones of Primate AAVs" *Molecular Therapy* 9(Supplement 1):S36 (2004).

\* cited by examiner

SEQUENCE LISTING

<160> NUMBER OF SEQ ID NOS: 164

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes Gln, Asn, Ser, Pro, Ala, or Gly
<220> FEATURE:
<221> NAME/KEY: MISC_FEATURE
<222> LOCATION: (2)..(3)
<223> OTHER INFORMATION: Xaa denotes any amino acid residue
<220> FEATURE:
<221> NAME/KEY: MISC_FEATURE
<222> LOCATION: (4)..(4)
<223> OTHER INFORMATION: Xaa denotes Thr, Ala, Gly or Asn
<220> FEATURE:
<221> NAME/KEY: MISC_FEATURE
<222> LOCATION: (5)..(5)
<223> OTHER INFORMATION: Xaa denotes any amino acid residue
<220> FEATURE:
<221> NAME/KEY: MISC_FEATURE
<222> LOCATION: (6)..(6)
<223> OTHER INFORMATION: Xaa denotes Pro or Ala

<400> SEQUENCE: 1

Xaa Xaa Xaa Xaa Xaa Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Ala Gly Asn Ala Gln Ala
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Arg Gly Asn Arg Gln Ala
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Ser Ser Ser Thr Asp Pro
1               5

<210> SEQ ID NO 5
<211> LENGTH: 6
<212> TYPE: PRT
<213> ORGANISM: Artificial Sequence

```
<220> FEATURE:
<223> OTHER INFORMATION: Synthetic peptide

<400> SEQUENCE: 5

Ser Ser Asn Thr Ala Pro
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Ser Asn Ser Asn Leu Pro
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Ser Ser Thr Thr Ala Pro
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Ala Ala Asn Thr Ala Ala
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Gln Gln Asn Thr Ala Pro
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Ser Ala Gln Ala Gln Ala
1               5

<210> SEQ ID NO 11
<211> LENGTH: 6
<212> TYPE: PRT
<213> ORGANISM: Artificial Sequence
<220> FEATURE:
```

<223> OTHER INFORMATION: Synthetic peptide

<400> SEQUENCE: 11

Gln Ala Asn Thr Gly Pro
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Asn Ala Thr Thr Ala Pro
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Ser Ser Thr Ala Gly Pro
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Gln Gln Asn Thr Ala Ala
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Pro Ser Thr Ala Gly Pro
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

Asn Gln Asn Thr Ala Pro
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

```
<400> SEQUENCE: 17

Gln Ala Ala Asn Ala Pro
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide

<400> SEQUENCE: 18

Ser Ile Val Gly Leu Pro
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Ala Ala Ser Thr Ala Ala
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide

<400> SEQUENCE: 20

Ser Ser Thr Ala Gly Pro
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Ser Gln Asn Thr Thr Ala
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

Gln Gln Asp Thr Ala Pro
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide
```

```
<400> SEQUENCE: 23

Gln Thr Asn Thr Gly Pro
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide

<400> SEQUENCE: 24

Gln Thr Asn Gly Ala Pro
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide

<400> SEQUENCE: 25

Gln Gln Asn Ala Ala Pro
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide

<400> SEQUENCE: 26

Ala Ala Asn Thr Gln Ala
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic peptide

<400> SEQUENCE: 27

Ala Ala Ser Thr Ala Ala
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide

<400> SEQUENCE: 28

Ala Gly Ala Ala Gln Ala
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide

<400> SEQUENCE: 29
```

```
Ser Gly Asn Thr Gln Ala
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide

<400> SEQUENCE: 30

Ser Ser Asn Thr Gln Ala
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic peptide

<400> SEQUENCE: 31

Asn Ser Asn Thr Ala Pro
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa denotes any amino acid residue
<220> FEATURE:
<221> NAME/KEY: MISC_FEATURE
<222> LOCATION: (5)..(5)
<223> OTHER INFORMATION: Xaa denotes any amino acid residue

<400> SEQUENCE: 32

Ala Xaa Xaa Ala Xaa Ala
1               5

<210> SEQ ID NO 33
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes a basic amino acid residue
<220> FEATURE:
<221> NAME/KEY: MISC_FEATURE
<222> LOCATION: (2)..(3)
<223> OTHER INFORMATION: Xaa denotes a neutral and/or hydrophobic amino
      acid residue
<220> FEATURE:
<221> NAME/KEY: MISC_FEATURE
<222> LOCATION: (4)..(4)
<223> OTHER INFORMATION: Xaa denotes a basic amino acid residue

<400> SEQUENCE: 33

Xaa Xaa Xaa Xaa
1

<210> SEQ ID NO 34
```

```
<211> LENGTH: 4
<212> TYPE: PRT
<213> ORGANISM: Artificial Sequence
<220> FEATURE:
<223> OTHER INFORMATION: Synthetic peptide

<400> SEQUENCE: 34

Arg Gly Asn Arg
1

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa denotes Gly or Ser

<400> SEQUENCE: 35

Asn Ser Val Arg Asp Leu Xaa
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide

<400> SEQUENCE: 36

Pro Arg Ser Val Thr Val Pro
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa denotes any amino acid residue
<220> FEATURE:
<221> NAME/KEY: MISC_FEATURE
<222> LOCATION: (7)..(7)
<223> OTHER INFORMATION: Xaa denotes Ser or Ala

<400> SEQUENCE: 37

Asn Ser Val Ser Ser Xaa Xaa
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide

<400> SEQUENCE: 38

Asn Gly Arg Ala His Ala
1               5

<210> SEQ ID NO 39
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 39

Gln Pro Glu His Ser Ser Thr
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40

Val Asn Thr Ala Asn Ser Thr
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic peptide

<400> SEQUENCE: 41

His Gly Pro Met Gln Lys Ser
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide

<400> SEQUENCE: 42

Pro His Lys Pro Pro Leu Ala
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide

<400> SEQUENCE: 43

Ile Lys Asn Asn Glu Met Trp
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide

<400> SEQUENCE: 44

Arg Asn Leu Asp Thr Pro Met
1               5

<210> SEQ ID NO 45
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 45

Val Asp Ser His Arg Gln Ser
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic peptide

<400> SEQUENCE: 46

Tyr Asp Ser Lys Thr Lys Thr
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide

<400> SEQUENCE: 47

Ser Gln Leu Pro His Gln Lys
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide

<400> SEQUENCE: 48

Ser Thr Met Gln Gln Asn Thr
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic peptide

<400> SEQUENCE: 49

Thr Glu Arg Tyr Met Thr Gln
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic peptide

<400> SEQUENCE: 50

Gln Pro Glu His Ser Ser Thr
1               5

<210> SEQ ID NO 51
<211> LENGTH: 7
<212> TYPE: PRT
<213> ORGANISM: Artificial Sequence
<220> FEATURE:
```

```
<223> OTHER INFORMATION: Synthetic peptide

<400> SEQUENCE: 51

Asp Ala Ser Leu Ser Thr Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide

<400> SEQUENCE: 52

Asp Leu Pro Asn Lys Lys Thr
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide

<400> SEQUENCE: 53

Asp Leu Thr Ala Ala Arg Leu
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic peptide

<400> SEQUENCE: 54

Glu Pro His Gln Phe Asn Tyr
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

Glu Pro Gln Ser Asn His Thr
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide

<400> SEQUENCE: 56

Met Ser Ser Trp Pro Ser Gln
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 57

Asn Pro Lys His Asn Ala Thr
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide

<400> SEQUENCE: 58

Pro Asp Gly Met Arg Thr Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Pro Asn Asn Asn Lys Thr Thr
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic peptide

<400> SEQUENCE: 60

Gln Ser Thr Thr His Asp Ser
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide

<400> SEQUENCE: 61

Thr Gly Ser Lys Gln Lys Gln
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic peptide

<400> SEQUENCE: 62

Ser Leu Lys His Gln Ala Leu
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 63

Ser Pro Ile Asp Gly Glu Gln
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic peptide

<400> SEQUENCE: 64

Trp Ile Phe Pro Trp Ile Gln Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic peptide

<400> SEQUENCE: 65

Cys Asp Cys Arg Gly Asp Cys Phe Cys
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic peptide

<400> SEQUENCE: 66

Cys Asn Gly Arg Cys
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide

<400> SEQUENCE: 67

Cys Pro Arg Glu Cys Glu Ser
1               5

<210> SEQ ID NO 68
<211> LENGTH: 10
<212> TYPE: PRT
<213> ORGANISM: Artificial Sequence
<220> FEATURE:
<223> OTHER INFORMATION: Synthetic peptide

<400> SEQUENCE: 68

Cys Thr Thr His Trp Gly Phe Thr Leu Cys
1               5                   10

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide

<400> SEQUENCE: 69
```

```
Cys Gly Arg Arg Ala Gly Gly Ser Cys
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic peptide

<400> SEQUENCE: 70

Cys Lys Gly Gly Arg Ala Lys Asp Cys
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic peptide

<400> SEQUENCE: 71

Cys Val Pro Glu Leu Gly His Glu Cys
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic peptide

<400> SEQUENCE: 72

Cys Arg Arg Glu Thr Ala Trp Ala Lys
1               5

<210> SEQ ID NO 73
<211> LENGTH: 14
<212> TYPE: PRT
<213> ORGANISM: Artificial Sequence
<220> FEATURE:
<223> OTHER INFORMATION: Synthetic peptide

<400> SEQUENCE: 73

Val Ser Trp Phe Ser His Arg Tyr Ser Pro Phe Ala Val Ser
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Synthetic peptide

<400> SEQUENCE: 74

Gly Tyr Arg Asp Gly Tyr Ala Gly Pro Ile Leu Tyr Asn
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(3)
```

<223> OTHER INFORMATION: Xaa denotes any amino acid residue
<220> FEATURE:
<221> NAME/KEY: MISC_FEATURE
<222> LOCATION: (5)..(7)
<223> OTHER INFORMATION: Xaa denotes any amino acid residue

<400> SEQUENCE: 75

Xaa Xaa Xaa Tyr Xaa Xaa Xaa
1               5

<210> SEQ ID NO 76
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa denotes Glu or Met

<400> SEQUENCE: 76

Tyr Xaa Asn Trp
1

<210> SEQ ID NO 77
<211> LENGTH: 7
<212> TYPE: PRT
<213> ORGANISM: Artificial Sequence
<220> FEATURE:
<223> OTHER INFORMATION: Synthetic peptide

<400> SEQUENCE: 77

Arg Pro Leu Pro Pro Leu Pro
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic peptide

<400> SEQUENCE: 78

Ala Pro Pro Leu Pro Pro Arg
1               5

<210> SEQ ID NO 79
<211> LENGTH: 12
<212> TYPE: PRT
<213> ORGANISM: Artificial Sequence
<220> FEATURE:
<223> OTHER INFORMATION: Synthetic peptide

<400> SEQUENCE: 79

Asp Val Phe Tyr Pro Tyr Pro Tyr Ala Ser Gly Ser
1               5                   10

<210> SEQ ID NO 80
<211> LENGTH: 6
<212> TYPE: PRT
<213> ORGANISM: Artificial Sequence
<220> FEATURE:
<223> OTHER INFORMATION: Synthetic peptide

<400> SEQUENCE: 80

Met Tyr Trp Tyr Pro Tyr
1               5

```
<210> SEQ ID NO 81
<211> LENGTH: 12
<212> TYPE: PRT
<213> ORGANISM: Artificial Sequence
<220> FEATURE:
<223> OTHER INFORMATION: Synthetic peptide

<400> SEQUENCE: 81

Asp Ile Thr Trp Asp Gln Leu Trp Asp Leu Met Lys
1               5                   10

<210> SEQ ID NO 82
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa denotes Gly or Leu

<400> SEQUENCE: 82

Cys Trp Asp Asp Xaa Trp Leu Cys
1               5

<210> SEQ ID NO 83
<211> LENGTH: 14
<212> TYPE: PRT
<213> ORGANISM: Artificial Sequence
<220> FEATURE:
<223> OTHER INFORMATION: Synthetic peptide

<400> SEQUENCE: 83

Glu Trp Cys Glu Tyr Leu Gly Gly Tyr Leu Arg Cys Tyr Ala
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa denotes any amno acid residue
<220> FEATURE:
<221> NAME/KEY: MISC_FEATURE
<222> LOCATION: (4)..(5)
<223> OTHER INFORMATION: Xaa denotes any amno acid residue
<220> FEATURE:
<221> NAME/KEY: MISC_FEATURE
<222> LOCATION: (8)..(8)
<223> OTHER INFORMATION: Xaa denotes any amno acid residue
<220> FEATURE:
<221> NAME/KEY: MISC_FEATURE
<222> LOCATION: (11)..(11)
<223> OTHER INFORMATION: Xaa denotes any amno acid residue
<220> FEATURE:
<221> NAME/KEY: MISC_FEATURE
<222> LOCATION: (13)..(13)
<223> OTHER INFORMATION: Xaa denotes any amno acid residue

<400> SEQUENCE: 84

Tyr Xaa Cys Xaa Xaa Gly Pro Xaa Thr Trp Xaa Cys Xaa Pro
1               5                   10

<210> SEQ ID NO 85
```

```
<211> LENGTH: 14
<212> TYPE: PRT
<213> ORGANISM: Artificial Sequence
<220> FEATURE:
<223> OTHER INFORMATION: Synthetic peptide

<400> SEQUENCE: 85

Ile Glu Gly Pro Thr Leu Arg Gln Trp Leu Ala Ala Arg Ala
1               5                   10

<210> SEQ ID NO 86
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(4)
<223> OTHER INFORMATION: Xaa denotes any amino acid residue
<220> FEATURE:
<221> NAME/KEY: MISC_FEATURE
<222> LOCATION: (5)..(5)
<223> OTHER INFORMATION: Xaa denotes Tyr, Trp, Phe, or His

<400> SEQUENCE: 86

Leu Trp Xaa Xaa Xaa
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes any amino acid residue
<220> FEATURE:
<221> NAME/KEY: MISC_FEATURE
<222> LOCATION: (3)..(4)
<223> OTHER INFORMATION: Xaa denotes any amino acid residue

<400> SEQUENCE: 87

Xaa Phe Xaa Xaa Tyr Leu Trp
1               5

<210> SEQ ID NO 88
<211> LENGTH: 13
<212> TYPE: PRT
<213> ORGANISM: Artificial Sequence
<220> FEATURE:
<223> OTHER INFORMATION: Synthetic peptide

<400> SEQUENCE: 88

Ser Ser Ile Ile Ser His Phe Arg Trp Gly Leu Cys Asp
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Synthetic peptide

<400> SEQUENCE: 89

Met Ser Arg Pro Ala Cys Pro Pro Asn Asp Lys Tyr Glu
1               5                   10
```

```
<210> SEQ ID NO 90
<211> LENGTH: 8
<212> TYPE: PRT
<213> ORGANISM: Artificial Sequence
<220> FEATURE:
<223> OTHER INFORMATION: Synthetic peptide

<400> SEQUENCE: 90

Cys Leu Arg Ser Gly Arg Gly Cys
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic peptide

<400> SEQUENCE: 91

Cys His Trp Met Phe Ser Pro Trp Cys
1               5

<210> SEQ ID NO 92
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa denotes any amino acid residue

<400> SEQUENCE: 92

Trp Xaa Xaa Phe
1

<210> SEQ ID NO 93
<211> LENGTH: 8
<212> TYPE: PRT
<213> ORGANISM: Artificial Sequence
<220> FEATURE:
<223> OTHER INFORMATION: Synthetic peptide

<400> SEQUENCE: 93

Cys Ser Ser Arg Leu Asp Ala Cys
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic peptide

<400> SEQUENCE: 94

Cys Leu Pro Val Ala Ser Cys
1               5

<210> SEQ ID NO 95
<211> LENGTH: 13
<212> TYPE: PRT
<213> ORGANISM: Artificial Sequence
<220> FEATURE:
<223> OTHER INFORMATION: Synthetic peptide

<400> SEQUENCE: 95
```

```
Cys Gly Phe Glu Cys Val Arg Gln Cys Pro Glu Arg Cys
1               5                   10
```

<210> SEQ ID NO 96
<211> LENGTH: 13
<212> TYPE: PRT
<213> ORGANISM: Artificial Sequence
<220> FEATURE:
<223> OTHER INFORMATION: Synthetic peptide

<400> SEQUENCE: 96

```
Cys Val Ala Leu Cys Arg Glu Ala Cys Gly Glu Gly Cys
1               5                   10
```

<210> SEQ ID NO 97
<211> LENGTH: 9
<212> TYPE: PRT
<213> ORGANISM: Artificial Sequence
<220> FEATURE:
<223> OTHER INFORMATION: Synthetic peptide

<400> SEQUENCE: 97

```
Ser Trp Cys Glu Pro Gly Trp Cys Arg
1               5
```

<210> SEQ ID NO 98
<211> LENGTH: 7
<212> TYPE: PRT
<213> ORGANISM: Artificial Sequence
<220> FEATURE:
<223> OTHER INFORMATION: Synthetic peptide

<400> SEQUENCE: 98

```
Tyr Ser Gly Lys Trp Gly Trp
1               5
```

<210> SEQ ID NO 99
<211> LENGTH: 7
<212> TYPE: PRT
<213> ORGANISM: Artificial Sequence
<220> FEATURE:
<223> OTHER INFORMATION: Synthetic peptide

<400> SEQUENCE: 99

```
Gly Leu Ser Gly Gly Arg Ser
1               5
```

<210> SEQ ID NO 100
<211> LENGTH: 7
<212> TYPE: PRT
<213> ORGANISM: Artificial Sequence
<220> FEATURE:
<223> OTHER INFORMATION: Synthetic peptide

<400> SEQUENCE: 100

```
Leu Met Leu Pro Arg Ala Asp
1               5
```

<210> SEQ ID NO 101
<211> LENGTH: 9
<212> TYPE: PRT
<213> ORGANISM: Artificial Sequence
<220> FEATURE:
<223> OTHER INFORMATION: Synthetic peptide

<400> SEQUENCE: 101

Cys Ser Cys Phe Arg Asp Val Cys Cys

```
<210> SEQ ID NO 102
<211> LENGTH: 9
<212> TYPE: PRT
<213> ORGANISM: Artificial Sequence
<220> FEATURE:
<223> OTHER INFORMATION: Synthetic peptide

<400> SEQUENCE: 102

Cys Arg Asp Val Val Ser Val Ile Cys
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic peptide

<400> SEQUENCE: 103

Met Ala Arg Ser Gly Leu
1               5

<210> SEQ ID NO 104
<211> LENGTH: 6
<212> TYPE: PRT
<213> ORGANISM: Artificial Sequence
<220> FEATURE:
<223> OTHER INFORMATION: Synthetic peptide

<400> SEQUENCE: 104

Met Ala Arg Ala Lys Glu
1               5

<210> SEQ ID NO 105
<211> LENGTH: 6
<212> TYPE: PRT
<213> ORGANISM: Artificial Sequence
<220> FEATURE:
<223> OTHER INFORMATION: Synthetic peptide

<400> SEQUENCE: 105

Met Ser Arg Thr Met Ser
1               5

<210> SEQ ID NO 106
<211> LENGTH: 6
<212> TYPE: PRT
<213> ORGANISM: Artificial Sequence
<220> FEATURE:
<223> OTHER INFORMATION: Synthetic peptide

<400> SEQUENCE: 106

Lys Cys Cys Tyr Ser Leu
1               5

<210> SEQ ID NO 107
<211> LENGTH: 14
<212> TYPE: PRT
<213> ORGANISM: Artificial Sequence
<220> FEATURE:
<223> OTHER INFORMATION: Synthetic peptide

<400> SEQUENCE: 107

Met Tyr Trp Gly Asp Ser His Trp Leu Gln Tyr Trp Tyr Glu
1               5                   10
```

```
<210> SEQ ID NO 108
<211> LENGTH: 7
<212> TYPE: PRT
<213> ORGANISM: Artificial Sequence
<220> FEATURE:
<223> OTHER INFORMATION: Synthetic peptide

<400> SEQUENCE: 108

Met Gln Leu Pro Leu Ala Thr
1               5

<210> SEQ ID NO 109
<211> LENGTH: 4
<212> TYPE: PRT
<213> ORGANISM: Artificial Sequence
<220> FEATURE:
<223> OTHER INFORMATION: Synthetic peptide

<400> SEQUENCE: 109

Glu Trp Leu Ser
1

<210> SEQ ID NO 110
<211> LENGTH: 4
<212> TYPE: PRT
<213> ORGANISM: Artificial Sequence
<220> FEATURE:
<223> OTHER INFORMATION: Synthetic peptide

<400> SEQUENCE: 110

Ser Asn Glu Trp
1

<210> SEQ ID NO 111
<211> LENGTH: 4
<212> TYPE: PRT
<213> ORGANISM: Artificial Sequence
<220> FEATURE:
<223> OTHER INFORMATION: Synthetic peptide

<400> SEQUENCE: 111

Thr Asn Tyr Leu
1

<210> SEQ ID NO 112
<211> LENGTH: 8
<212> TYPE: PRT
<213> ORGANISM: Artificial Sequence
<220> FEATURE:
<223> OTHER INFORMATION: Synthetic peptide

<400> SEQUENCE: 112

Trp Ile Phe Pro Trp Ile Gln Leu
1               5

<210> SEQ ID NO 113
<211> LENGTH: 12
<212> TYPE: PRT
<213> ORGANISM: Artificial Sequence
<220> FEATURE:
<223> OTHER INFORMATION: Synthetic peptide

<400> SEQUENCE: 113

Trp Asp Leu Ala Trp Met Phe Arg Leu Pro Val Gly
1               5                   10
```

```
<210> SEQ ID NO 114
<211> LENGTH: 13
<212> TYPE: PRT
<213> ORGANISM: Artificial Sequence
<220> FEATURE:
<223> OTHER INFORMATION: Synthetic peptide

<400> SEQUENCE: 114

Cys Thr Val Ala Leu Pro Gly Gly Tyr Val Arg Val Cys
1               5                   10

<210> SEQ ID NO 115
<211> LENGTH: 9
<212> TYPE: PRT
<213> ORGANISM: Artificial Sequence
<220> FEATURE:
<223> OTHER INFORMATION: Synthetic peptide

<400> SEQUENCE: 115

Cys Val Pro Glu Leu Gly His Glu Cys
1               5

<210> SEQ ID NO 116
<211> LENGTH: 13
<212> TYPE: PRT
<213> ORGANISM: Artificial Sequence
<220> FEATURE:
<223> OTHER INFORMATION: Synthetic peptide

<400> SEQUENCE: 116

Cys Val Ala Tyr Cys Ile Glu His His Cys Trp Thr Cys
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Synthetic peptide

<400> SEQUENCE: 117

Cys Val Phe Ala His Asn Tyr Asp Tyr Leu Val Cys
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Synthetic peptide

<400> SEQUENCE: 118

Cys Val Phe Thr Ser Asn Tyr Ala Phe Cys
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Synthetic peptide

<400> SEQUENCE: 119

Val His Ser Pro Asn Lys Lys
1               5
```

```
<210> SEQ ID NO 120
<211> LENGTH: 7
<212> TYPE: PRT
<213> ORGANISM: Artificial Sequence
<220> FEATURE:
<223> OTHER INFORMATION: Synthetic peptide

<400> SEQUENCE: 120

Cys Arg Gly Asp Gly Trp Cys
1               5

<210> SEQ ID NO 121
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes any amino acid residue
<220> FEATURE:
<221> NAME/KEY: MISC_FEATURE
<222> LOCATION: (6)..(6)
<223> OTHER INFORMATION: Xaa denotes any amino acid residue

<400> SEQUENCE: 121

Xaa Arg Gly Cys Asp Xaa
1               5

<210> SEQ ID NO 122
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa denotes any amino acid residue
<220> FEATURE:
<221> NAME/KEY: MISC_FEATURE
<222> LOCATION: (4)..(4)
<223> OTHER INFORMATION: Xaa denotes Ser or Thr

<400> SEQUENCE: 122

Pro Xaa Xaa Xaa
1

<210> SEQ ID NO 123
<211> LENGTH: 10
<212> TYPE: PRT
<213> ORGANISM: Artificial Sequence
<220> FEATURE:
<223> OTHER INFORMATION: Synthetic peptide

<400> SEQUENCE: 123

Cys Thr Thr His Trp Gly Phe Thr Leu Cys
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Synthetic peptide

<400> SEQUENCE: 124

Ser Gly Lys Gly Pro Arg Gln Ile Thr Ala Leu
1               5                   10
```

<210> SEQ ID NO 125
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Xaa denotes Arg or Lys
<220> FEATURE:
<221> NAME/KEY: MISC_FEATURE
<222> LOCATION: (10)..(10)
<223> OTHER INFORMATION: Xaa denotes Ala or Gln
<220> FEATURE:
<221> NAME/KEY: MISC_FEATURE
<222> LOCATION: (11)..(11)
<223> OTHER INFORMATION: Xaa denotes Asn or Ala
<220> FEATURE:
<221> NAME/KEY: MISC_FEATURE
<222> LOCATION: (12)..(12)
<223> OTHER INFORMATION: Xaa denotes Leu or Tyr
<220> FEATURE:
<221> NAME/KEY: MISC_FEATURE
<222> LOCATION: (13)..(13)
<223> OTHER INFORMATION: Xaa denotes Thr, Val, Met, or Arg

<400> SEQUENCE: 125

Ala Ala Ala Ala Ala Ala Ala Ala Ala Xaa Xaa Xaa Xaa Xaa
1               5                   10

<210> SEQ ID NO 126
<211> LENGTH: 6
<212> TYPE: PRT
<213> ORGANISM: Artificial Sequence
<220> FEATURE:
<223> OTHER INFORMATION: Synthetic peptide

<400> SEQUENCE: 126

Val Tyr Met Ser Pro Phe
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic peptide

<400> SEQUENCE: 127

Ala Thr Trp Leu Pro Pro Arg
1               5

<210> SEQ ID NO 128
<211> LENGTH: 12
<212> TYPE: PRT
<213> ORGANISM: Artificial Sequence
<220> FEATURE:
<223> OTHER INFORMATION: Synthetic peptide

<400> SEQUENCE: 128

His Thr Met Tyr Tyr His His Tyr Gln His His Leu
1               5                   10

<210> SEQ ID NO 129
<211> LENGTH: 19
<212> TYPE: PRT
<213> ORGANISM: Artificial Sequence
<220> FEATURE:

```
<223> OTHER INFORMATION: Synthetic peptide

<400> SEQUENCE: 129

Ser Glu Val Gly Cys Arg Ala Gly Pro Leu Gln Trp Leu Cys Glu Lys
1               5                   10                  15

Tyr Phe Gly

<210> SEQ ID NO 130
<211> LENGTH: 18
<212> TYPE: PRT
<213> ORGANISM: Artificial Sequence
<220> FEATURE:
<223> OTHER INFORMATION: Synthetic peptide

<400> SEQUENCE: 130

Cys Gly Leu Leu Pro Val Gly Arg Pro Asp Arg Asn Val Trp Arg Trp
1               5                   10                  15

Leu Cys

<210> SEQ ID NO 131
<211> LENGTH: 15
<212> TYPE: PRT
<213> ORGANISM: Artificial Sequence
<220> FEATURE:
<223> OTHER INFORMATION: Synthetic peptide

<400> SEQUENCE: 131

Cys Lys Gly Gln Cys Asp Arg Phe Lys Gly Leu Pro Trp Glu Cys
1               5                   10                  15

<210> SEQ ID NO 132
<211> LENGTH: 5
<212> TYPE: PRT
<213> ORGANISM: Artificial Sequence
<220> FEATURE:
<223> OTHER INFORMATION: Synthetic peptide

<400> SEQUENCE: 132

Ser Gly Arg Ser Ala
1               5

<210> SEQ ID NO 133
<211> LENGTH: 4
<212> TYPE: PRT
<213> ORGANISM: Artificial Sequence
<220> FEATURE:
<223> OTHER INFORMATION: Synthetic peptide

<400> SEQUENCE: 133

Trp Gly Phe Pro
1

<210> SEQ ID NO 134
<211> LENGTH: 17
<212> TYPE: PRT
<213> ORGANISM: Artificial Sequence
<220> FEATURE:
<223> OTHER INFORMATION: Synthetic peptide

<400> SEQUENCE: 134

Ala Glu Pro Met Pro His Ser Leu Asn Phe Ser Gln Tyr Leu Trp Tyr
1               5                   10                  15

Thr
```

```
<210> SEQ ID NO 135
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa denotes Trp or Phe

<400> SEQUENCE: 135

Trp Ala Tyr Xaa Ser Pro
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic peptide

<400> SEQUENCE: 136

Ile Glu Leu Leu Gln Ala Arg
1               5

<210> SEQ ID NO 137
<211> LENGTH: 16
<212> TYPE: PRT
<213> ORGANISM: Artificial Sequence
<220> FEATURE:
<223> OTHER INFORMATION: Synthetic peptide

<400> SEQUENCE: 137

Ala Tyr Thr Lys Cys Ser Arg Gln Trp Arg Thr Cys Met Thr Thr His
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Synthetic peptide

<400> SEQUENCE: 138

Pro Gln Asn Ser Lys Ile Pro Gly Pro Thr Phe Leu Asp Pro His
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Synthetic peptide

<400> SEQUENCE: 139

Ser Met Glu Pro Ala Leu Pro Asp Trp Trp Trp Lys Met Phe Lys
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Synthetic peptide

<400> SEQUENCE: 140

Ala Asn Thr Pro Cys Gly Pro Tyr Thr His Asp Cys Pro Val Lys Arg
```

```
1               5                   10                  15
```

<210> SEQ ID NO 141
<211> LENGTH: 12
<212> TYPE: PRT
<213> ORGANISM: Artificial Sequence
<220> FEATURE:
<223> OTHER INFORMATION: Synthetic peptide

<400> SEQUENCE: 141

```
Thr Ala Cys His Gln His Val Arg Met Val Arg Pro
1               5                   10
```

<210> SEQ ID NO 142
<211> LENGTH: 12
<212> TYPE: PRT
<213> ORGANISM: Artificial Sequence
<220> FEATURE:
<223> OTHER INFORMATION: Synthetic peptide

<400> SEQUENCE: 142

```
Val Pro Trp Met Glu Pro Ala Tyr Gln Arg Phe Leu
1               5                   10
```

<210> SEQ ID NO 143
<211> LENGTH: 8
<212> TYPE: PRT
<213> ORGANISM: Artificial Sequence
<220> FEATURE:
<223> OTHER INFORMATION: Synthetic peptide

<400> SEQUENCE: 143

```
Asp Pro Arg Ala Thr Pro Gly Ser
1               5
```

<210> SEQ ID NO 144
<211> LENGTH: 12
<212> TYPE: PRT
<213> ORGANISM: Artificial Sequence
<220> FEATURE:
<223> OTHER INFORMATION: Synthetic peptide

<400> SEQUENCE: 144

```
Phe Arg Pro Asn Arg Ala Gln Asp Tyr Asn Thr Asn
1               5                   10
```

<210> SEQ ID NO 145
<211> LENGTH: 9
<212> TYPE: PRT
<213> ORGANISM: Artificial Sequence
<220> FEATURE:
<223> OTHER INFORMATION: Synthetic peptide

<400> SEQUENCE: 145

```
Cys Thr Lys Asn Ser Tyr Leu Met Cys
1               5
```

<210> SEQ ID NO 146
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa denotes Gln or Arg
<220> FEATURE:

```
<221> NAME/KEY: MISC_FEATURE
<222> LOCATION: (3)..(3)
<223> OTHER INFORMATION: Xaa denotes Leu or Arg
<220> FEATURE:
<221> NAME/KEY: MISC_FEATURE
<222> LOCATION: (5)..(5)
<223> OTHER INFORMATION: Xaa denotes Gly or Asn
<220> FEATURE:
<221> NAME/KEY: MISC_FEATURE
<222> LOCATION: (6)..(7)
<223> OTHER INFORMATION: Xaa denotes any amino acid residue
<220> FEATURE:
<221> NAME/KEY: MISC_FEATURE
<222> LOCATION: (9)..(9)
<223> OTHER INFORMATION: Xaa denotes Ala or Val

<400> SEQUENCE: 146

Cys Xaa Xaa Thr Xaa Xaa Xaa Gly Xaa Gly Cys
1               5                   10

<210> SEQ ID NO 147
<211> LENGTH: 9
<212> TYPE: PRT
<213> ORGANISM: Artificial Sequence
<220> FEATURE:
<223> OTHER INFORMATION: Synthetic peptide

<400> SEQUENCE: 147

Cys Pro Ile Glu Asp Arg Pro Met Cys
1               5

<210> SEQ ID NO 148
<211> LENGTH: 12
<212> TYPE: PRT
<213> ORGANISM: Artificial Sequence
<220> FEATURE:
<223> OTHER INFORMATION: Synthetic peptide

<400> SEQUENCE: 148

His Glu Trp Ser Tyr Leu Ala Pro Tyr Pro Trp Phe
1               5                   10

<210> SEQ ID NO 149
<211> LENGTH: 9
<212> TYPE: PRT
<213> ORGANISM: Artificial Sequence
<220> FEATURE:
<223> OTHER INFORMATION: Synthetic peptide

<400> SEQUENCE: 149

Met Cys Pro Lys His Pro Leu Gly Cys
1               5

<210> SEQ ID NO 150
<211> LENGTH: 15
<212> TYPE: PRT
<213> ORGANISM: Artificial Sequence
<220> FEATURE:
<223> OTHER INFORMATION: Synthetic peptide

<400> SEQUENCE: 150

Arg Met Trp Pro Ser Ser Thr Val Asn Leu Ser Ala Gly Arg Arg
1               5                   10                  15

<210> SEQ ID NO 151
<211> LENGTH: 20
<212> TYPE: PRT
<213> ORGANISM: Artificial Sequence
<220> FEATURE:
```

<223> OTHER INFORMATION: Synthetic peptide

<400> SEQUENCE: 151

Ser Ala Lys Thr Ala Val Ser Gln Arg Val Trp Leu Pro Ser His Arg
1               5                   10                  15

Gly Gly Glu Pro
            20

<210> SEQ ID NO 152
<211> LENGTH: 20
<212> TYPE: PRT
<213> ORGANISM: Artificial Sequence
<220> FEATURE:
<223> OTHER INFORMATION: Synthetic peptide

<400> SEQUENCE: 152

Lys Ser Arg Glu His Val Asn Asn Ser Ala Cys Pro Ser Lys Arg Ile
1               5                   10                  15

Thr Ala Ala Leu
            20

<210> SEQ ID NO 153
<211> LENGTH: 4
<212> TYPE: PRT
<213> ORGANISM: Artificial Sequence
<220> FEATURE:
<223> OTHER INFORMATION: Synthetic peptide

<400> SEQUENCE: 153

Glu Gly Phe Arg
1

<210> SEQ ID NO 154
<211> LENGTH: 6
<212> TYPE: PRT
<213> ORGANISM: Artificial Sequence
<220> FEATURE:
<223> OTHER INFORMATION: Synthetic peptide

<400> SEQUENCE: 154

Ala Gly Leu Gly Val Arg
1               5

<210> SEQ ID NO 155
<211> LENGTH: 15
<212> TYPE: PRT
<213> ORGANISM: Artificial Sequence
<220> FEATURE:
<223> OTHER INFORMATION: Synthetic peptide

<400> SEQUENCE: 155

Gly Thr Arg Gln Gly His Thr Met Arg Leu Gly Val Ser Asp Gly
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Synthetic peptide

<400> SEQUENCE: 156

Ile Ala Gly Leu Ala Thr Pro Gly Trp Ser His Trp Leu Ala Leu
1               5                   10                  15

```
<210> SEQ ID NO 157
<211> LENGTH: 7
<212> TYPE: PRT
<213> ORGANISM: Artificial Sequence
<220> FEATURE:
<223> OTHER INFORMATION: Synthetic peptide

<400> SEQUENCE: 157

Ser Met Ser Ile Ala Arg Leu
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic peptide

<400> SEQUENCE: 158

His Thr Phe Glu Pro Gly Val
1               5

<210> SEQ ID NO 159
<211> LENGTH: 15
<212> TYPE: PRT
<213> ORGANISM: Artificial Sequence
<220> FEATURE:
<223> OTHER INFORMATION: Synthetic peptide

<400> SEQUENCE: 159

Asn Thr Ser Leu Lys Arg Ile Ser Asn Lys Arg Ile Arg Arg Lys
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Synthetic peptide

<400> SEQUENCE: 160

Leu Arg Ile Lys Arg Lys Arg Arg Lys Arg Lys Lys Thr Arg Lys
1               5                   10                  15

<210> SEQ ID NO 161
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa denotes any amino acid residue
<220> FEATURE:
<221> NAME/KEY: MISC_FEATURE
<222> LOCATION: (5)..(5)
<223> OTHER INFORMATION: Xaa denotes any amino acid residue

<400> SEQUENCE: 161

Gln Xaa Xaa Thr Xaa Pro
1               5

<210> SEQ ID NO 162
<211> LENGTH: 6
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (2)..(3)
<223> OTHER INFORMATION: Xaa denotes any amino acid residue
<220> FEATURE:
<221> NAME/KEY: MISC_FEATURE
<222> LOCATION: (5)..(5)
<223> OTHER INFORMATION: Xaa denotes any amino acid residue

<400> SEQUENCE: 162

Asn Xaa Xaa Thr Xaa Pro
1               5

<210> SEQ ID NO 163
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa denotes any amino acid residue
<220> FEATURE:
<221> NAME/KEY: MISC_FEATURE
<222> LOCATION: (5)..(5)
<223> OTHER INFORMATION: Xaa denotes any amino acid residue

<400> SEQUENCE: 163

Ser Xaa Xaa Ala Xaa Pro
1               5

<210> SEQ ID NO 164
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes Gln or Asn
<220> FEATURE:
<221> NAME/KEY: MISC_FEATURE
<222> LOCATION: (2)..(3)
<223> OTHER INFORMATION: Xaa denotes any amino acid residue
<220> FEATURE:
<221> NAME/KEY: MISC_FEATURE
<222> LOCATION: (5)..(5)
<223> OTHER INFORMATION: Xaa denotes any amino acid residue

<400> SEQUENCE: 164

Xaa Xaa Xaa Thr Xaa Pro
1               5
```

MODIFIED VIRUS VECTORS AND METHODS OF MAKING AND USING THE SAME

RELATED APPLICATION INFORMATION

This application is a continuation of U.S. application Ser. No. 13/201,154, filed Sep. 29, 2011, now U.S. Pat. No. 8,889,641, issued Nov. 18, 2014, which is a 35 U.S.C. §371 national phase application of PCT Application No. PCT/US2010/023885, filed Feb. 11, 2010, which claims the benefit of U.S. Provisional Application No. 61/151,736, filed Feb. 11, 2009, the disclosure of each of which is incorporated by reference herein in its entirety.

STATEMENT OF GOVERNMENT SUPPORT

This invention was made with government support under Grant No. AR055712 awarded by the National Institutes of Health. The government has certain rights in the invention.

FIELD OF THE INVENTION

The present invention relates to modified capsid proteins from adeno-associated virus (AAV) and virus capsids and virus vectors comprising the same. In particular, the invention relates to modified AAV capsid proteins and capsids comprising the same that can be incorporated into virus vectors to confer a desirable transduction profile with respect to a target tissue(s) of interest.

STATEMENT REGARDING ELECTRONIC FILING OF A SEQUENCE LISTING

A Sequence Listing in ASCII text format, submitted under 37 C.F.R. §1.821, entitled 5470-490WO_ST25.txt, 35,665 bytes in size, generated on Mar. 31, 2010 and filed via EFS-Web, is provided in lieu of a paper copy. The Sequence Listing is incorporated herein by reference into the specification for its disclosures.

BACKGROUND OF THE INVENTION

New adeno-associated virus (AAV) strains isolated from animal tissues and adenoviral stocks have expanded the panel of AAV vectors available for therapeutic gene transfer applications. Comprehensive efforts to map tissue tropisms of these AAV isolates in animal models are currently underway. For instance, recent studies with AAV serotypes 1-9 indicate a broad tissue tropism in mice following intravenous administration. The AAV serotypes 8 and 9 are particularly notable for their ability to transduce multiple organs including heart, liver and skeletal muscle following intravenous administration. While the latter serotypes are well-suited for systemic gene transfer modalities, the ability to direct homing of AAV vectors to selective organs is useful for gene therapy. The development of tissue-specific promoters and miRNA-based gene regulation strategies to sharply segregate gene expression patterns among different tissue types is noteworthy in this regard. However, such regulatory components do not preclude sequestration of AAV vector genomes in off-target organs following systemic administration.

A particularly striking aspect of tissue tropisms displayed by AAV serotypes and variants is their propensity to ubiquitously accumulate within and transduce the liver, albeit with varying efficiency. The molecular basis of this preferential liver tropism has been mapped, in the case of AAV2 and AAV6, to a continuous basic footprint that appears to be involved in the interaction of either serotype with heparin. Specifically, it has previously been demonstrated that a single lysine residue on AAV6 (K531) dictates heparin binding ability and consequently, liver tropism. In corollary, substitutional mutagenesis of the corresponding glutamate/aspartate residue on other serotypes with a lysine residue confers heparin binding, possibly by forming a minimum continuous basic footprint on the capsid surface.

The present inventor addresses a need in the art for nucleic acid delivery vectors with desirable features.

SUMMARY OF THE INVENTION

A comprehensive mutagenesis approach yielded three groups of modified AAV capsid proteins conferring overlapping phenotypes: (a) AAV capsid protein mutants that confer systemic spread; (b) AAV capsid protein mutants that confer detargeting from the liver; (c) AAV capsid protein mutants that confer low efficiency transduction in one or more tissues (e.g., brain). Thus, the invention provides an array of synthetic viral vectors displaying a range of transduction profiles that are suitable for different in vitro and in vivo applications.

Accordingly, as one aspect the invention provides an adeno-associated virus (AAV) capsid protein, wherein the capsid protein comprises a modification resulting in the amino acid sequence $$X^1\text{-}X^2\text{-}X^3\text{-}X^4\text{-}X^5\text{-}X^6 \quad \text{(SEQ ID NO: 1)}$$

at the amino acids corresponding to amino acid positions 585 to 590 (VP1 numbering) of the native AAV2 capsid protein,
wherein $X^1$ is Q, N, S, P, A or G;
wherein $X^2$ is any amino acid;
wherein $X^3$ is any amino acid;
wherein $X^4$ is T, A, G or N;
wherein $X^5$ is any amino acid; and
wherein $X^6$ is P or A.
In particular embodiments, $X^1\text{-}X^2\text{-}X^3\text{-}X^4\text{-}X^5\text{-}X^6$ (SEQ ID NO:1) is not AGNAQA (SEQ IQ NO:2).

As a further aspect, the invention also provides an AAV capsid comprising an AAV capsid protein of the invention.

As yet another aspect, the invention provides a virus vector comprising:

(a) an AAV capsid of the invention; and (b) a nucleic acid comprising at least one terminal repeat sequence, wherein the nucleic acid is encapsidated by the AAV capsid.

Further provided are pharmaceutical formulations comprising a virus capsid and/or virus vector of the invention in a pharmaceutically acceptable carrier.

As still a further aspect, the invention provides a method of administering a nucleic acid to a cell, the method comprising contacting the cell with a virus vector or pharmaceutical formulation of the invention.

As another aspect, the invention provides a method of delivering a nucleic acid to a subject, the method comprising administering to the subject a virus vector or pharmaceutical formulation of the invention.

Figure 1:
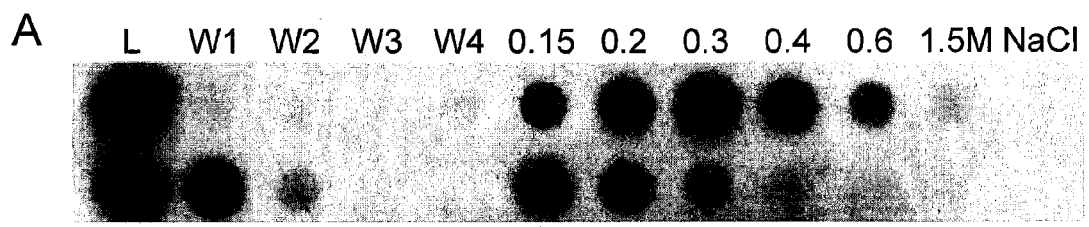
FIG. 1.
Figure 1:
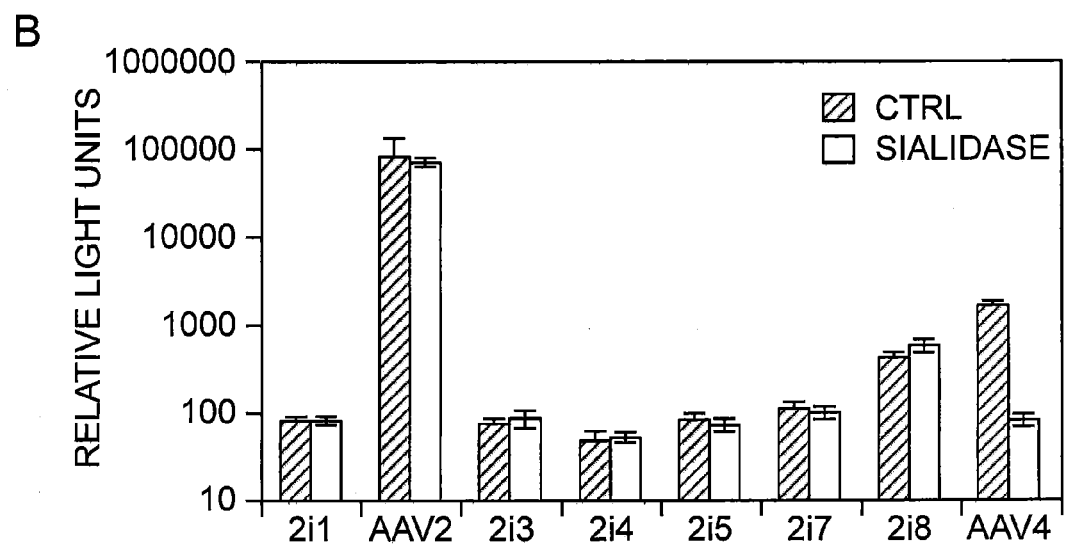
Figure 1:
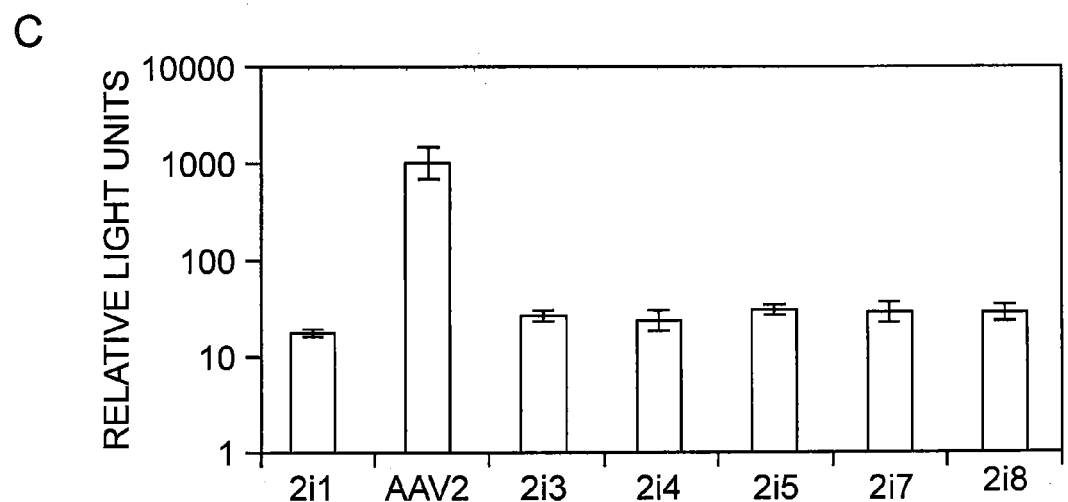

(A) Elution profile of parental AAV2 capsids (top) and AAV2i8 (bottom) from a heparin affinity column. Samples were loaded (L) onto heparin-agarose affinity columns in 1×PBS, washed multiple times with 0.1×PBS (W1-4) and eluted at different salt concentrations (0.15M to 1.5M NaCl). Collected fractions were loaded onto a nitrocellulose membrane using a dot blot manifold and detected using the A20 monoclonal antibody, specific for intact AAV2 capsids. AAV2 peak fractions elute at ~300 mM NaCl, while AAV2i8 capsids elute under physiological conditions (pH 7.4; 0.15M NaCl).

(B) Analysis of in vitro transduction of AAV2i mutants in HEK 293 cells untreated (filled bars) or treated with 50 mU/mL sialidase (white bars). Luciferase transgene expression levels were determined in cell lysates harvested 24 hours post-infection with AAV2 or an AAV2i mutant (MOI 1000 vg/cell). AAV4 was included as a positive control. All experiments were performed in triplicate and standard deviation is shown.

(C) Analysis of in vitro transduction of AAV2i mutants in heparin sulfate-negative CHOpgsD cells. Luciferase transgene expression levels were determined in cell lysates harvested 24 hours post-infection with AAV2 or an AAV2i mutant (MOI 1000). All experiments were performed in triplicate and standard deviation is shown.

FIG. 2.

(A) Analysis of in vivo transduction of AAV2i mutants via intramuscular administration. BALB/c mice (n=3) were injected intramuscularly with AAV2i CMV-Luc vectors (dose 1×10$^{10}$ vg in 200 µl PBS). Representative photographs and live animal bioluminescent images of luciferase transgene expression were obtained at 1 week after injection. Bioluminescence scale ranges from 0-4×10$^6$ relative light units (photons/sec/cm$^2$).

(B) Analysis of in vivo transduction of AAV2i mutants via intravenous administration. BALB/c mice (n=3) were injected intravenously (tail vein) with AAV2i CMV-Luc vectors (dose 1×10$^{10}$ vg in 200 µl PBS). Representative photographs and live animal bioluminescent images of luciferase transgene expression were obtained at 1 week after injection. Bioluminescence scale ranges from 0-4×10$^5$ relative light units (photons/sec/cm$^2$).

FIG. 3.

Comparison of the in vivo transduction profiles of AAV2 and AAV2i8 administered via different intravenous injection routes. BALB/c mice were injected with AAV2 or AAV2i8 CMV-Luc vector (dose 4×10$^{10}$ vg in 200 µl PBS) through either the tail or portal vein. Representative photographs and live animal bioluminescent images of luciferase transgene expression were obtained at 1 week after injection. Bioluminescence scale ranges from 0-2×10$^5$ relative light units (photons/sec/cm$^2$).

FIG. 4.

Comparison of in vivo transduction via intravenous administration of AAV2i vectors with AAV2 and AAV8 vectors. BALB/c mice (n=3) were injected intravenously (tail vein) with AAV2, AAV8, AAV2i8 and structurally related AAV2i mutants (dose 1×10$^{11}$ vg in 200 µl PBS) packaging the chicken beta actin (CBA)-Luc cassette. Representative photographs and live animal bioluminescent images of luciferase transgene expression were obtained. Bioluminescence scale ranges from 0-3×10$^6$ relative light units (photons/sec/cm$^2$).

FIG. 5.

Comparison of the in vivo transduction profiles of AAV1 i8 and AAV3i8. BALB/c mice were injected intravenously via the tail vein with AAV1, AAV3, AAV1 i8 or AAV3i8 vectors (dose 1×10$^{11}$ vg in 200 µl PBS) packaging the CBA-Luc cassette. Representative photographs and live animal bioluminescent images of luciferase transgene expression were obtained at 1 week after injection. Bioluminescence scale ranges from 1-3×10$^6$ relative light units (photons/sec/cm$^2$).

FIG. 6A.

Quantitation of transduction efficiency of AAV2i8 vectors compared to AAV2 and AAV8 in cardiac, skeletal muscle (pooled hind limb and abdominal muscles) and liver tissues as measured by luciferase expression. Tissue lysates were obtained from BALB/c mice (n=3) at 2 weeks after administration of AAV2, AAV2i8 and AAV8 (dose 1×10$^{11}$ vg, tail vein) and subjected to luminometric analysis. Luciferase levels are shown as relative light units normalized to protein levels determined using a Bradford assay. Error bars indicate standard deviation.

FIG. 6B.

Quantitation of transduction efficiency of AAV2i8 vectors compared to AAV2 and AAV8 in cardiac, skeletal muscle (pooled hind limb and abdominal muscles) and liver tissues as measured by luciferase genome copy number via Q-PCR. Host genomic as well vector DNA was extracted from tissue lysates obtained from BALB/c mice (n=3) at 2 weeks after administration of AAV2, AAV2i8 and AAV8 (dose 1×10$^{11}$ vg, tail vein). Host and vector genome copy number were determined by Q-PCR with specific primer sets against the lamin gene and luciferase transgene, respectively.

FIG. 7.

In vivo transduction efficiency of AAV2i8 of various muscle groups following intravenous administration. Luciferase transgene expression in major muscle sub-groups obtained from BALB/c mice (n=3) at 2 weeks after intravenous administration of AAV2i8 (dose 1×10$^{11}$ vg, tail vein) packaging the CBA-Luc cassette. Tissue lysates from five different muscle groups from the hind limb skeletal muscle (alternating filled and white bars), three groups from the forelimb (alternating filled and white bars), intercostals, cardiac, facial, diaphragm, tongue, abdominal and vertebral muscle types (filled bars) were subjected to luminometric analysis. Luciferase levels are shown as relative light units normalized to protein levels determined by a Bradford assay. Error bars indicate standard deviation.

FIG. 8.

Comparison of the biodistribution of AAV2i8 and related vectors. BALB/c mice were injected with AAV2i8 or related vectors having a Q/NxxTxP (SEQ ID NO:164) motif (dose 1×10$^{11}$ vg in 200 µl PBS) packaging the CBA-Luc cassette. Host and vector genome copy numbers were determined by Q-PCR with specific primer sets against the lamin gene and luciferase transgene, respectively.

FIG. 9.

(A) Luciferase transgene expression in pooled skeletal muscle subgroups from right and left hind limb of BALB/c mice (n=4) after isolated perfusion of AAV2i8 (filled bars) or AAV8 (white bars) into each saphenous vein. Tissue lysates prepared after administration of three different doses (1×10$^9$, 1×101$^0$, 1×10$^{11}$ vg) in low (200 µl), medium (500 µl) or high (1 ml) volume of injection were subjected to luminometric analysis. Luciferase levels are shown as relative light units normalized to protein levels determined using a Bradford assay.

(B) Vector genome copy numbers recovered from blood at different time intervals after administration through the tail vein (n=3). Whole blood DNA was extracted and analyzed by Q-PCR with primers against the luciferase transgene. AAV2i8 shows prolonged circulation compared with AAV8. Error bars indicate standard deviation.

FIG. 10.

Kinetics of luciferase transgene expression in mice following intravenous injection of AAV2i8 vector (dose $1\times10^{11}$ vg in 200 μl PBS) packaging the (CBA)-Luc cassette. Representative photographs and live animal bioluminescent images of luciferase transgene expression were obtained at different time intervals after injection (3 days, 1 week, 4 weeks or 12 weeks).

FIG. 11.

Comparison of the in vivo transduction profiles of 2i8D and 2i8E. BALB/c mice were injected intravenously via the tail vein with AAV2, AAV8, AAV9, 2i8D or 2i8E vectors (dose $1\times10^{11}$ vg in 200 μl PBS) packaging the CBA-Luc cassette. Representative photographs and live animal bioluminescent images of luciferase transgene expression were obtained at 4 days after injection.

DETAILED DESCRIPTION OF THE INVENTION

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

The designation of all amino acid positions in the AAV capsid proteins in the description of the invention and the appended claims is with respect to VP1 capsid subunit numbering (native AAV2 VP1 capsid protein: GenBank Accession No. AACO3780 or YP680426). It will be understood by those skilled in the art that the modifications described herein if inserted into the AAV cap gene may result in modifications in the VP1, VP2 and/or VP3 capsid subunits. Alternatively, the capsid subunits can be expressed independently to achieve modification in only one or two of the capsid subunits (VP1, VP2, VP3, VP1 +VP2, VP1+VP3, or VP2 +VP3).

Definitions

The following terms are used in the description herein and the appended claims:

The singular forms "a," "an" and "the" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or"). Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

As used herein, the terms "reduce," "reduces," "reduction" and similar terms mean a decrease of at least about 25%, 35%, 50%, 75%, 80%, 85%, 90%, 95%, 97% or more.

As used herein, the terms "enhance," "enhances," "enhancement" and similar terms indicate an increase of at least about 25%, 50%, 75%, 100%, 150%, 200%, 300%, 400%, 500% or more.

The term "parvovirus" as used herein encompasses the family Parvoviridae, including autonomously replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, BI 9 virus, and any other autonomous parvovirus now known or later discovered. Other autonomous parvoviruses are known to those skilled in the art. See, e.g., BERNARD N. FIELDS et al., VIROLOGY, volume 2, chapter 69 (4th ed., Lippincott-Raven Publishers).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine MV, canine AAV, equine MV, ovine AAV, and any other AAV now known or later discovered. See, e.g., BERNARD N. FIELDS et al., VIROLOGY, volume 2, chapter 69 (4th ed., Lippincott-Raven Publishers). A number of relatively new AAV serotypes and clades have been identified (see, e.g., Gao et al., (2004) J. Virology 78:6381-6388; Moris et al., (2004) Virology 33-:375-383; and Table 1).

TABLE 1

| | GenBank Accession Number |
|---|---|
| Complete Genomes | |
| Adeno-associated virus 1 | NC_002077, AF063497 |
| Adeno-associated virus 2 | NC_001401 |

TABLE 1-continued

| | GenBank Accession Number |
|---|---|
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as GenBank. See, e.g., GenBank Accession Numbers NC-_002077, NC_001401, NC_Q01729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al., (1983) *J. Virology* 45:555; Chiorini et al., (1998) *J. Virology* 71:6823; Chiorini et al., (1999) *J. Virology*

73:1309; Bantel-Schaal et al., (1999) *J. Virology* 73:939; Xiao et al., (1999) *J. Virology* 73:3994; Muramatsu et al., (1996) *Virology* 221:208; Shade et al., (1986) *J. Virol.* 58:921; Gao et al., (2002) *Proc. Nat. Acad. Sci. USA* 99:11854; Moris et al., (2004) *Virology* 33-:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1.

The capsid structures of autonomous parvoviruses and AAV are described in more detail in BERNARD N. FIELDS et al., VIROLOGY, volume 2, chapters 69 & 70 (4th ed., Lippincott-Raven Publishers). See also, description of the crystal structure of AAV2 (Xie et al., (2002) *Proc. Nat. Acad. Sci.* 99:10405-10), AAV4 (Padron et al., (2005) *J. Virol.* 79: 5047-58), AAV5 (Walters et al., (2004) *J. Virol.* 78: 3361-71) and CPV (Xie et al., (1996) *J. Mol. Biol.* 6:497-520 and Tsao et al., (1991) *Science* 251: 1456-64).

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of a heterologous nucleic acid(s) of interest. Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus, from a non-integrated episome, as well as any other form in which the virus may take within the cell.

As used here, "systemic tropism" and "systemic transduction" (and equivalent terms) indicate that the virus capsid or virus vector of the invention exhibits tropism for or transduces, respectively, tissues throughout the body (e.g., brain, lung, skeletal muscle, heart, liver, kidney and/or pancreas). In embodiments of the invention, systemic transduction of muscle tissues (e.g., skeletal muscle, diaphragm and cardiac muscle) is observed. In other embodiments, systemic transduction of skeletal muscle tissues achieved. For example, in particular embodiments, essentially all skeletal muscles throughout the body are transduced (although the efficiency of transduction may vary by muscle type). In particular embodiments, systemic transduction of limb muscles, cardiac muscle and diaphragm muscle is achieved. Optionally, the virus capsid or virus vector is administered via a systemic route (e.g., systemic route such as intravenously, intra-articularly or intra-lymphatically). Alternatively, in other embodiments, the capsid or virus vector is delivered locally (e.g., to the footpad, intramuscularly, intradermally, subcutaneously, topically). Examples of modified virus vectors according to the present invention are provided in Table 5 (see also, FIG. 4).

Unless indicated otherwise, "efficient transduction" or "efficient tropism," or similar terms, can be determined by reference to a suitable control (e.g., at least about 50%, 60%, 70%, 80%, 85%, 90%, 95% or more of the transduction or tropism, respectively, of the control). In particular embodiments, the virus vector efficiently transduces or has efficient tropism for skeletal muscle, cardiac muscle, diaphragm muscle, pancreas (including β-islet cells), spleen, the gastrointestinal tract (e.g., epithelium and/or smooth muscle), cells of the central nervous system, lung, joint cells, and/or kidney. Suitable controls will depend on a variety of factors including the desired tropism profile. For example, AAV8 and AAV9 are highly efficient in transducing skeletal muscle, cardiac muscle and diaphragm muscle, but have the disadvantage of also transducing liver with high efficiency. Thus, the invention can be practiced to identify viral vectors of the invention that demonstrate the efficient transduction of skeletal, cardiac and/or diaphragm muscle of AAV8 or AAV9, but with a much lower transduction efficiency for liver. Further, because the tropism profile of interest may reflect tropism toward multiple target tissues, it will be appreciated that a suitable vector may represent some tradeoffs. To illustrate, a virus vector of the invention may be less efficient than AAV8 or AAV9 in transducing skeletal muscle, cardiac muscle and/or diaphragm muscle, but because of low level transduction of liver, may nonetheless be very desirable.

Similarly, it can be determined if a virus "does not efficiently transduce" or "does not have efficient tropism" for a target tissue, or similar terms, by reference to a suitable control. In particular embodiments, the virus vector does not efficiently transduce (i.e., has does not have efficient tropism) for liver, kidney, gonads and/or germ cells. In particular embodiments, undesirable transduction of tissue(s) (e.g., liver) is 20% or less, 10% or less, 5% or less, 1% or less, 0.1% or less of the level of transduction of the desired target tissue(s) (e.g., skeletal muscle, diaphragm muscle, cardiac muscle and/or cells of the central nervous system).

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In representative embodiments an "isolated" nucleotide is enriched by at least about 10-fold, 100-fold, 1000-fold, 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In representative embodiments an "isolated" polypeptide is enriched by at least about 10-fold, 100-fold, 1000-fold, 10,000-fold or more as compared with the starting material.

As used herein, by "isolate" or "purify" (or grammatical equivalents) a virus vector, it is meant that the virus vector is at least partially separated from at least some of the other components in the starting material. In representative embodiments an "isolated" or "purified" virus vector is enriched by at least about 10-fold, 100-fold, 1000-fold, 10,000-fold or more as compared with the starting material.

A "therapeutic polypeptide" is a polypeptide that can alleviate, reduce, prevent, delay and/or stabilize symptoms that result from an absence or defect in a protein in a cell or subject and/or is a polypeptide that otherwise confers a benefit to a subject, e.g., anti-cancer effects or improvement in transplant survivability.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject. A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. Generally, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

A "rAAV vector genome" or "rAAV genome" is an MV genome (i.e., vDNA) that comprises one or more heterologous nucleic acid sequences. rAAV vectors generally require only the terminal repeat(s) (TR(s)) in cis to generate virus. All other viral sequences are dispensable and may be supplied in trans (Muzyczka, (1992) Curr. Topics Microbiol. Immunol. 158:97). Typically, the rAAV vector genome will only retain the one or more TR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one TR sequence (e.g., MV TR sequence), optionally two TRs (e.g., two MV TRs), which typically will be at the 5' and 3' ends of the vector genome and flank the heterologous nucleic acid, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-MV TR. For example, a non-AAV TR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 1). An MV terminal repeat need not have the native terminal 1Q repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The virus vectors of the invention can further be "targeted" virus vectors (e.g., having a directed tropism) and/or a "hybrid" parvovirus (i.e., in which the viral TRs and viral capsid are from different parvoviruses) as described in international patent publication WO 00/28004 and Chao et al., (2000) Molecular Therapy 2:619.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

Further, the viral capsid or genomic elements can contain other modifications, including insertions, deletions and/or substitutions.

As used herein, the term "amino acid" encompasses any naturally occurring amino acid, modified forms thereof, and synthetic amino acids.

Naturally occurring, levorotatory (L-) amino acids are shown in Table 2).

Alternatively, the amino acid can be a modified amino acid residue (nonlimiting examples are shown in Table 3) and/or can be an amino acid that is modified by post-translation modification (e.g., acetylation, amidation, formylation, hydroxylation, methylation, phosphorylation or sulfatation).

TABLE 2

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |

TABLE 2-continued

| Amino Acid Residue | Abbreviation | |
|---|---|---|
| | Three-Letter Code | One-Letter Code |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 3

| Modified Amino Acid Residue | Abbreviation |
|---|---|
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methyivaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenyiglycine | Phg |
| Beta-2-thienylalanine | Thi |

Further, the non-naturally occurring amino acid can be an "unnatural" amino acid as described by Wang et al., *Annu Rev Biophys Biomol Struct.* 35:225-49 (2006)). These unnatural amino acids can advantageously be used to chemically link molecules of interest to the AAV capsid protein.
Modified AAV Capsid Proteins and Virus Capsids and Virus Vectors Comprising the Same.

The present invention provides AAV capsid proteins (VP1, VP2 and/or VP3) comprising a modification in the amino acid sequence in the three-fold axis loop 4 (Opie et al., *J. Virol.* 77: 6995-7006 (2003)) and virus capsids and virus vectors comprising the modified AAV capsid protein.

The inventors have discovered that modifications in this loop can confer one or more desirable properties to virus vectors comprising the modified AAV capsid protein including without limitation (i) reduced transduction of liver, (ii) enhanced movement across endothelial cells, (iii) systemic transduction; (iv) enhanced transduction of muscle tissue (e.g., skeletal muscle, cardiac muscle and/or diaphragm muscle), and/or (v) reduced transduction of brain tissues (e.g., neurons). Thus, the present invention addresses some of the limitations associated with conventional AAV vectors. For example, vectors based on AAV8 and rAAV9 vectors are attractive for systemic nucleic acid delivery because they readily cross the endothelial cell barrier; however, systemic administration of rAAV8 or rAAV9 results in most of the vector being delivered to the liver, thereby reducing transduction of other important target tissues such as skeletal muscle.

In embodiments of the invention, transduction of cardiac muscle and/or skeletal muscle (determined on the basis of an individual skeletal muscle, multiple skeletal muscles, or the whole range of skeletal muscles) is at least about five-fold, ten-fold, 50-fold, 100-fold, 1000-fold or higher than transduction levels in liver.

In particular embodiments, the modified AAV capsid protein of the invention comprises one or more modifications in the amino acid sequence of the three-fold axis loop 4 (e.g., amino acid positions 575 to 600 [inclusive] of the native AAV2 VP1 capsid protein or the corresponding region of a capsid protein from another AAV). As used herein, a "modification" in an amino acid sequence includes substitutions, insertions and/or deletions, each of which can involve one, two, three, four, five, six, seven, eight, nine, ten or more amino acids. In particular embodiments, the modification is a substitution. For example, in particular embodiments, 1, 2, 3, 4, 5, 6, 7, 8, 9, 10, 11, 12, 13, 14, 15, 16, 17, 18, 19, 20, 21, 22, 23, 24, 25 or more amino acids from the three-fold axis loop 4 from one AAV can be substituted into amino acid positions 575-60Q of the native AAV2 capsid protein or the corresponding positions of the capsid protein from another AAV. However, the modified virus capsids of the invention are not limited to AAV capsids in which amino acids from one AAV capsid are substituted into another AAV capsid, and the substituted and/or inserted amino acids can be from any source, and can further be naturally occurring or partially or completely synthetic.

As described herein, the nucleic acid and amino acid sequences of the capsid proteins from a number of AAV are known in the art. Thus, the amino acids "corresponding" to amino acid positions 575 to 600 (inclusive) or amino acid positions 585 to 590 (inclusive) of the native AAV2 capsid protein can be readily determined for any other AAV (e.g., by using sequence alignments).

The invention contemplates that the modified capsid proteins of the invention can be produced by modifying the capsid protein of any AAV now known or later discovered. Further, the AAV capsid protein that is to be modified can be a naturally occurring AAV capsid protein (e.g., an AAV2, AAV3a or 3b, AAV4, AAV5, AAV8, AAV9, AAV10 or AAV11 capsid protein or any of the AAV shown in Table 1) but is not so limited. Those skilled in the art will understand that a variety of manipulations to the AAV capsid proteins are known in the art and the invention is not limited to modifications of naturally occurring AAV capsid proteins. For example, the capsid protein to be modified may already have alterations as compared with naturally occurring MV (e.g., is derived from a naturally occurring AAV capsid protein, e.g., AAV2, AAV3a, AAV3b, AAV4, AAV5, AAV6, AAV7, AAV8, AAV9, AAV10 and/or AAV11 or any other AAV now known or later discovered). Such AAV capsid proteins are also within the scope of the present invention.

For example, the AAV capsid protein to be modified can comprise an amino acid insertion directly following amino acid 264 of the native AAV2 capsid protein sequence (see, e.g., WO 2006/066066) and/or can be an AAV with an altered HI loop as described in WO 2009/108274 and/or can be an AAV that is modified to contain a poly-His sequence to facilitate purification. As another illustrative example, the AAV capsid protein can have a peptide targeting sequence incorporated therein as an insertion or substitution. Further, the AAV capsid protein can comprise a large domain from another AAV that has been substituted and/or inserted into the capsid protein.

Thus, in particular embodiments, the AAV capsid protein to be modified can be derived from a naturally occurring AAV but further comprise one or more foreign sequences (e.g., that are exogenous to the native virus) that are inserted and/or substituted into the capsid protein and/or has been altered by deletion of one or more amino acids.

Accordingly, when referring herein to a specific AAV capsid protein (e.g., an AAV2, AAV3, AAV4, AAV5, AAV6, AAV7, AAV8, AAV9, AAV10 or AAV11 capsid protein or a capsid protein from any of the AAV shown in Table 1, etc.), it is intended to encompass the native capsid protein as well as capsid proteins that have alterations other than the modifications of the invention. Such alterations include substitutions, insertions and/or deletions. In particular embodiments, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids inserted therein (other than the insertions of the present invention) as compared with the native AAV capsid protein sequence. In embodiments of the invention, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acid substitutions (other than the amino acid substitutions according to the present invention) as compared with the native AAV capsid protein sequence. In embodiments of the invention, the capsid protein comprises a deletion of 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids (other than the amino acid deletions of the invention) as compared with the native AAV capsid protein sequence.

Thus, for example, the term "AAV2 capsid protein" includes AAV capsid proteins having the native AAV2 capsid protein sequence (see GenBank Accession No. AACO3780) as well as those comprising substitutions, insertions and/or deletions (as described in the preceding paragraph) in the native AAV2 capsid protein sequence.

In particular embodiments, the AAV capsid protein has the native AAV capsid protein sequence or has an amino acid sequence that is at least about 90%, 95%, 97%, 98% or 99% similar or identical to a native AAV capsid protein sequence. For example, in particular embodiments, an "AAV2" capsid protein encompasses the native AAV2 capsid protein sequence as well as sequences that are at least about 90%, 95%, 97%, 98% or 99% similar or identical to the native AAV2 capsid protein sequence.

Methods of determining sequence similarity or identity between two or more amino acid sequences are known in the art. Sequence similarity or identity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48,443 (1970), by the search for similarity method of Pearson & Lipman, *Proc. Natl. Acad. Sci. USA* 85,2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), or by inspection.

Another suitable algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology,* 266, 460-480 (1996); http://blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al., (1997) *Nucleic Acids Res.* 25, 3389-3402.

In embodiments of the invention, the AAV capsid protein sequence is not an AAV1, AAV3a and/or AAV3b capsid protein sequence.

In embodiments of the invention, the AAV capsid protein sequence is not the native AAV1, AAV3a and/or AAV3b capsid protein sequence.

Figure 7:
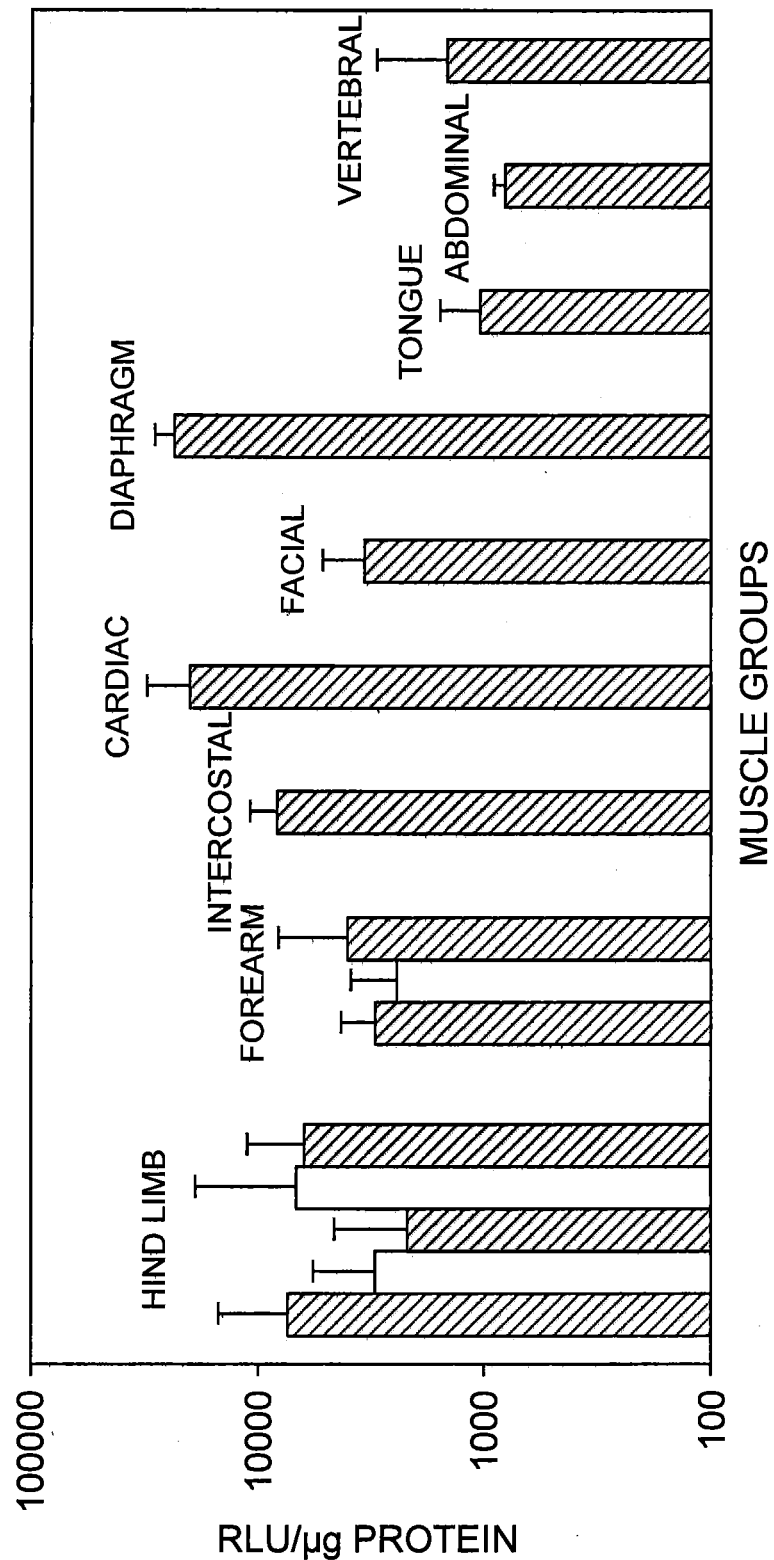

In representative embodiments of the invention, a modification is made in the region of amino acid positions 585 to 590 (inclusive) of the native AAV2 capsid protein (using VP1 numbering) or the corresponding positions of other AAV (native AAV2 VP1 capsid protein: GenBank Accession No. AACO3780 or YP680426), i.e., at the amino acids corresponding to amino acid positions 585 to 590 (VP1 numbering) of the native AAV2 capsid protein. The amino acid positions in other AAV serotypes or modified AAV capsids that "correspond to" positions 585 to 590 of the native AAV2 capsid protein will be apparent to those skilled in the art and can be readily determined using sequence alignment techniques (see, e.g., FIG. 7 of WO 2006/066066) and/or crystal structure analysis (Padron et al., (2005) *J. Virol.* 79:5047-58).

To illustrate, the modification can be introduced into an AAV capsid protein that already contains insertions and/or deletions such that the position of all downstream sequences is shifted. In this situation, the amino acid positions corresponding to amino acid positions 585 to 590 in the AAV2 capsid protein would still be readily identifiable to those skilled in the art. To illustrate, the capsid protein can be an AAV2 capsid protein that contains an insertion following amino acid position 264 (see, e.g., WO 2006/066066). The amino acids found at positions 585 through 590 (e.g., RGNRQA (SEQ ID NO:3) in the native AAV2 capsid protein) would now be at positions 586 through 591 but would still be identifiable to those skilled in the art.

In representative embodiments, the one or more modifications of the invention are incorporated into the AAV capsid at or directly adjacent to one or more amino acids in the following sequences:

(a) SSSTDP; (SEQ ID NO: 4)
(b) RGNRQA; (SEQ ID NO: 3)
(c) SSNTAP; (SEQ ID NO: 5)
(d) SNSNLP; (SEQ ID NO: 6)
(e) SSTTAP; (SEQ ID NO: 7)
(f) AANTAA; (SEQ ID NO: 8)
(g) QQNTAP; (SEQ ID NO: 9)
(h) SAQAQA; (SEQ ID NO: 10)
(i) QANTGP; or (SEQ ID NO: 11)
(j) NATTAP. (SEQ ID NO: 12)

In other representative embodiments of the invention, one or more amino acid substitutions (e.g., 1, 2, 3, 4, 5 or 6) are incorporated in the region of amino acid 585 to 590 (inclusive) of the amino acid sequence of the AAV2 capsid protein or the corresponding positions of other AAV.

The invention also contemplates a modified AAV capsid protein (e.g., VP1, VP2 and/or VP3) comprising the sequence $X^1$-$X^2$-$X^3$-$X^4$-$X^5$-$X^6$ (SEQ ID NO:1) at the amino acid positions corresponding to 585 to 590 (inclusive) of the native AAV2 capsid protein or the corresponding positions of other AAV.

In embodiments of the invention, the amino acid sequence $X^1$-$X^2$-$X^3$-$X^4$-$X^5$-$X^6$ (SEQ ID NO:1) is substituted for the amino acid sequence:

(a) SSSTDP; (SEQ ID NO: 4)
(b) RGNRQA; (SEQ ID NO: 3)
(c) SSNTAP; (SEQ ID NO: 5)
(d) SNSNLP; (SEQ ID NO: 6)
(e) SSTTAP; (SEQ ID NO: 7)
(f) AANTAA; (SEQ ID NO: 8)
(g) QQNTAP; (SEQ ID NO: 9)
(h) SAQAQA; (SEQ ID NO: 10)
(i) QANTGP; or (SEQ ID NO: 11)
(j) NATTAP (SEQ ID NO: 12)

in the native amino acid sequence of the capsid protein.

A library of sequences can be generated for $X^1$-$X^2$-$X^3$-$X^4$-$X^5$-$X^6$ (SEQ ID NO:1) using methods well-known to those skilled in the art. The library sequences can be incorporated into AAV capsid subunits and screened for desirable characteristics using known techniques.

In embodiments of the invention, $X^1$ can be any naturally occurring and/or non-naturally occurring amino acid. In embodiments of the invention, $X^1$ is an amino acid selected from: A, N, D, C, E, Q, G, H, I, L, K, M, F, P, S, T, W, Y and/or V.

In embodiments of the invention, $X^1$ is not a basic amino acid.

In embodiments of the invention, $X^1$ is not selected from R, K and/or H.

In embodiments of the invention, $X^1$ is not an amino acid comprising a cyclic side chain (for example, is not selected from H, F, P, W and/or Y).

In embodiments of the invention, $X^1$ is not selected from C, E, A and/or M.

In embodiments of the invention, $X^1$ is not P.

In embodiments of the invention, $X^1$ is not S and/or N.

In embodiments of the invention, $X^1$ is a neutral amino acid (for example, is selected from A, N, C, Q, G, I, L, M, F, P, S, T, W, Y and/or V).

In embodiments of the invention, $X^1$ is a hydrophilic amino acid (for example, is selected from R, N, D, E, Q, H, K, S, T and/or Y).

In embodiments of the invention, $X^1$ is a hydrophilic and neutral amino acid (for example, is selected from Q, N, S and T).

In embodiments of the invention, $X^1$ is selected from Q, N, S, P, A and/or G.

In embodiments of the invention, $X^1$ is selected from Q, N, S, A, D and/or E.

In embodiments of the invention, $X^1$ is selected from Q, S, N and/or A.

In embodiments of the invention, $X^1$ is selected from Q and/or N.

In embodiments of the invention, $X^1$ is Q.

In embodiments of the invention, $X^1$ is N.

In embodiments of the invention, $X^1$ is A.

In embodiments of the invention, $X^1$ is S.

$X^2$ can be any naturally occurring and/or non-naturally occurring amino acid. In representative embodiments, $X^2$ is an amino acid selected from: A, R, N, D, C, E, Q, G, H, I, L, K, M, F, P, S, T, W, Y and/or V.

In embodiments of the invention, $X^2$ is not a basic amino acid.

In embodiments of the invention, $X^2$ is not selected from R, K and/or H.

In embodiments of the invention, $X^2$ is not an amino acid comprising a cyclic side chain (for example, is not selected from H, F, P, W and/or Y).

In embodiments of the invention, $X^2$ is not selected from C and/or M.

In embodiments of the invention, $X^2$ is not P.

In embodiments of the invention, $X^2$ is not S.

In embodiments of the invention, $X^2$ is a neutral amino acid (for example, is selected from A, N, C, Q, G, I, L, M, F, P, S, T, W, Y and/or V).

In embodiments of the invention, $X^2$ is a hydrophilic amino acid (for example, is selected from R, N, D, E, Q, H, K, S, T and/or Y).

In embodiments of the invention, $X^2$ is selected from G, A, I, L, V, Q, N, D and/or E.

In embodiments of the invention, $X^2$ is selected from Q, S, N, G and/or A.

In embodiments of the invention, $X^2$ is not selected from G and/or A.

In embodiments of the invention, $X^2$ is Q.
In embodiments of the invention, $X^2$ is A.

$X^3$ can be any naturally occurring or non-naturally occurring amino acid. In embodiments of the invention $X^3$ is an amino acid selected from: A, R, N, D, C, E, Q, G, H, I, L, K, M, F, P, S, T, W, Y and/or V.

In embodiments of the invention, $X^3$ is not a basic amino acid.

In embodiments of the invention, $X^3$ is not selected from R, K and/or H.

In embodiments of the invention, $X^3$ is not an amino acid comprising a cyclic side chain (for example, is not selected from H, F, P, W and/or Y).

In embodiments of the invention, $X^3$ is not selected from C and/or M.

In embodiments of the invention, $X^3$ is not N.
In embodiments of the invention, $X^3$ is not I.
In embodiments of the invention, $X^3$ is not A.
In embodiments of the invention, $X^3$ is not P.

In embodiments of the invention, $X^3$ is a neutral amino acid (for example, is selected from A, N, C, Q, G, I, L, M, F, P, S, T, W, Y and/or V).

In embodiments of the invention, $X^3$ is a hydrophilic amino acid (for example, is selected from R, N, D, E, Q, H, K, S, T and/or Y).

In embodiments of the invention, $X^3$ is selected from Q, N, D and/or E.

In embodiments of the invention, $X^3$ is selected from Q, N, T and/or S.

In embodiments of the invention, $X^3$ is N.
In embodiments of the invention, $X^3$ is Q.

$X^4$ can be any naturally occurring and/or non-naturally occurring amino acid. In embodiments of the invention, $X^4$ is an amino acid selected from: A, R, N, D, C, E, Q, G, H, I, L, K, M, F, P, S, T, W, Y and/or V.

In embodiments of the invention, $X^4$ is not a basic amino acid.

In embodiments of the invention, $X^4$ is not selected from R, K and/or H.

In embodiments of the invention, $X^4$ is not an amino acid comprising a cyclic side chain (for example, is not selected from H, F, P, W and/or Y).

In embodiments of the invention, $X^4$ is not selected from C, A, E and/or M.

In embodiments of the invention, $X^4$ is not P.

In embodiments of the invention, $X^4$ is a neutral amino acid (for example, is selected from A, N, C, Q, G, I, L, M, F, P, S, T, W, Y and/or V).

In embodiments of the invention, $X^4$ is a hydrophilic amino acid (for example, is selected from R, N, D, E, Q, H, K, S, T and/or Y).

In embodiments of the invention, $X^4$ is a hydrophilic and neutral amino acid (for example, is selected from Q, N, S and T).

In embodiments of the invention, $X^4$ is selected from T, S, A, G, I, L and/or V.

In embodiments of the invention, $X^4$ is selected from T, A, G and/or N.

In embodiments of the invention, $X^4$ is T.
In embodiments of the invention, $X^4$ is A.

$X^5$ can be any naturally occurring and/or non-naturally occurring amino acid. In embodiments of the invention $X^5$ is an amino acid selected from: A, R, N, D, C, E, Q, G, H, I, L, K, M, F, P, S, T, W, Y and/or V. 2Q In embodiments of the invention, $X^5$ is not a basic amino acid.

In embodiments of the invention, $X^5$ is not selected from R, K and/or H.

In embodiments of the invention, $X^5$ is not an amino acid comprising a cyclic side chain (for example, is not selected from H, F, P, W and/or Y).

In embodiments of the invention, $X^5$ is not selected from C and/or M.

In embodiments of the invention, $X^5$ is not P.

In embodiments of the invention, $X^5$ is a neutral amino acid (for example, is selected from A, N, C, Q, G, I, L, M, F, P, S, T, W, Y and/or V).

In embodiments of the invention, $X^5$ is a hydrophilic amino acid (for example, is selected from R, N, D, E, Q, H, K, S, T and/or Y).

In embodiments of the invention, $X^5$ is selected from Q, N, T, S, A, G, I, L and/or V.

In embodiments of the invention, $X^5$ is selected from Q, N, T, S, A, G, L and/or D.

In embodiments of the invention, $X^5$ is Q.
In embodiments of the invention, $X^5$ is A.
In embodiments of the invention, $X^5$ is not Q.

$X^6$ can be any naturally occurring and/or non-naturally occurring amino acid. In embodiments of the invention, $X^6$ is an amino acid selected from: A, R, N, D, C, E, Q, G, H, I, L, K, M, F, P, S, T, W, Y and/or V.

In embodiments of the invention, $X^6$ is not a basic amino acid.

In embodiments of the invention, $X^6$ is not selected from R, K and/or H.

In embodiments of the invention, $X^6$ is not selected from C and/or M.

In embodiments of the invention, $X^6$ is a neutral amino acid (for example, is selected from A, N, C, Q, G, I, L, M, F, P, S, T, W, Y and/or V).

In embodiments of the invention, $X^6$ is a hydrophilic amino acid (for example, is selected from R, N, D, E, Q, H, K, S, T and/or Y).

In embodiments of the invention, $X^6$ is selected from P, A, G, I, L and/or V.

In embodiments of the invention, $X^6$ is P.
In embodiments of the invention, $X^6$ is A.
In embodiments of the invention, $X^6$ is not A.

In the modified AAV capsid proteins of the invention, the amino acid sequence $X^1$-$X^2$-$X^3$-$X^4$-$X^5$-$X^6$ (SEQ ID NO:1) can comprise any combination of the features described individually for each of $X^1$, $X^2$, $X^3$, $X^4$, $X^5$ and $X^6$.

In representative embodiments, the modified AAV capsid protein comprises the amino acid sequence $X^1$-$X^2$-$X^3$-$X^4$-$X^5$-$X^6$ (SEQ ID NO:1) at the amino acids corresponding to amino acids positions 585 to 590 (inclusive; VP1 numbering) of the native AAV2 capsid protein or the corresponding amino acid positions of other AAV capsid proteins,
wherein $X^1$ is selected from Q, N, S, P, A and/or G;
wherein $X^2$ is selected from any amino acid;
wherein $X^3$ is selected from any amino acid;
wherein $X^4$ is selected from T, A, G and/or N;
wherein $X^5$ is selected from any amino acid; and
wherein $X^6$ is selected from P and/or A.

In embodiments of the invention, $X^1$ is selected from Q, S, N and/or A.

In embodiments of the invention, $X^2$ is selected from Q, S, N, A and/or G.

In embodiments of the invention, $X^3$ is selected from S, N, T and/or Q.

In embodiments of the invention, $X^5$ is selected from S, N, T and/or Q.

In embodiments of the invention, $X^6$ is P.
In embodiments of the invention:
$X^1$ is selected from Q and/or N;
$X^4$ is T; and/or
$X^6$ is P.
In embodiments of the invention:
$X^2$ is Q;
$X^3$ is N; and/or
$X^5$ is A.
In other exemplary embodiments of the invention, $X^1$-$X^2$-$X^3$-$X^4$-$X^5$-$X^6$ (SEQ ID NO:1) has the sequence:

(a) QQNTAP (SEQ ID NO: 9)
(b) AANTAA (SEQ ID NO: 8)
(c) SSTAGP (SEQ ID NO: 13)
(d) QQNTAA (SEQ ID NO: 14)
(e) PSTAGP (SEQ ID NO: 15)
(f) SSSTDP (SEQ ID NO: 4)
(g) SNSNLP (SEQ ID NO: 6)
(h) SSTTAP (SEQ ID NO: 7)
(i) SAQAQA (SEQ ID NO: 10)
(j) QANTGP (SEQ ID NO: 11)
(k) NATTAP (SEQ ID NO: 12)
(l) NQNTAP (SEQ ID NO: 16)
(m) QAANAP (SEQ ID NO: 17)
(n) SIVGLP (SEQ ID NO: 18)
(o) AASTAA (SEQ ID NO: 19)
(p) SSNTAP (SEQ ID NO: 5)
(q) SSTAGP (SEQ ID NO: 20)
(r) SQNTTA (SEQ ID NO: 21)
(s) QQDTAP (SEQ ID NO: 22)
(t) QTNTGP (SEQ ID NO: 23)
(u) QTNGAP (SEQ ID NO: 24)
(v) QQNAAP (SEQ ID NO: 25)
(w) AANTQA; or (SEQ ID NO: 26)
(x) AASTAA. (SEQ ID NO: 27)

In some embodiments of the invention $X^1$-$X^2$-$X^3$-$X^4$-$X^5$-$X^6$ (SEQ ID NO:1) is not selected from AGNAQA (SEQ ID NO:2) and/or AGAAQA (SEQ ID NO:28).

In embodiments of the invention, $X^1$-$X^2$-$X^3$-$X^4$-$X^5$-$X^6$ (SEQ ID NO:1) is not SGNTQA (SEQ ID NO:29), SSNTQA (SEQ ID NO:30) and/or NSNTAP (SEQ ID NO:31).

In embodiments of the invention, $X^1$-$X^2$-$X^3$-$X^4$-$X^5$-$X^6$ (SEQ ID NO:1) is not AXXAXA (SEQ ID NO:32).

In embodiments of the invention, $X^1$-$X^2$-$X^3$-$X^4$-$X^5$-$X^6$ (SEQ ID NO:1) does not comprise RGD.

In embodiments of the invention, $X^5$ is not G when $X^6$ is D.

In embodiments of the invention, $X^1$-$X^2$-$X^3$-$X^4$-$X^5$-$X^6$ (SEQ ID NO:1) is RGNRQA (SEQ ID NO:3, e.g., when the AAV capsid subunit is not an AAV2 capsid subunit or an AAV capsid subunit derived from AAV2).

The invention also provides a virus capsid comprising, consisting essentially of, or consisting of the modified AAV capsid protein of the invention. In particular embodiments, the virus capsid is a parvovirus capsid, which may further be an autonomous parvovirus capsid or a dependovirus capsid. Optionally, the virus capsid is an AAV capsid. In particular embodiments, the AAV capsid is an AAV1, AAV2, AAV3a, AAV3b, AAV4, AAV5, AAV6, AAV7, AAV8, AAV9, AAV10, AAV11 or any other AAV shown in Table 1 or is derived from any of the foregoing by one or more insertions, substitutions and/or deletions.

The modified virus capsids can be used as "capsid vehicles," as has been described, for example, in U.S. Pat. No. 5,863,541. Molecules that can be packaged by the modified virus capsid and transferred into a cell include heterologous DNA, RNA, polypeptides, small organic molecules, metals, or combinations of the same.

Heterologous molecules are defined as those that are not naturally found in an AAV infection, e.g., those not encoded by a wild-type AAV genome. Further, therapeutically useful molecules can be associated with the outside of the chimeric virus capsid for transfer of the molecules into host target cells. Such associated molecules can include DNA, RNA, small organic molecules, metals, carbohydrates, lipids and/or polypeptides. In one embodiment of the invention the therapeutically useful molecule is covalently linked (i.e., conjugated or chemically coupled) to the capsid proteins. Methods of covalently linking molecules are known by those skilled in the art.

The modified virus capsids of the invention also find use in raising antibodies against the novel capsid structures. As a further alternative, an exogenous amino acid sequence may be inserted into the modified virus capsid for antigen presentation to a cell, e.g., for administration to a subject to produce an immune response to the exogenous amino acid sequence.

In other embodiments, the virus capsids can be administered to block certain cellular sites prior to and/or concurrently with (e.g., within minutes or hours of each other) administration of a virus vector delivering a nucleic acid encoding a polypeptide or functional RNA of interest. For example, the inventive capsids can be delivered to block cellular receptors on liver cells and a delivery vector can be administered subsequently or concurrently, which may reduce transduction of liver cells, and enhance transduction of other targets (e.g., skeletal, cardiac and/or diaphragm muscle).

According to representative embodiments, modified virus capsids can be administered to a subject prior to and/or concurrently with a modified virus vector according to the present invention. Further, the invention provides compositions and pharmaceutical formulations comprising the inventive modified virus capsids; optionally, the composition also comprises a modified virus vector of the invention.

The invention also provides nucleic acids (optionally, isolated nucleic acids) encoding the modified virus capsids and capsid proteins of the invention. Further provided are vectors comprising the nucleic acids, and cells (in vivo or in culture) comprising the nucleic acids and/or vectors of the invention. Suitable vectors include without limitation viral vectors (e.g., adenovirus, AAV, herpesvirus, vaccinia, poxviruses, baculoviruses, and the like), plasmids, phage, YACs, BACs, and the like. Such nucleic acids, vectors and cells can be used, for example, as reagents (e.g., helper packaging constructs or packaging cells) for the production of modified virus capsids or virus vectors as described herein.

Virus capsids according to the invention can be produced using any method known in the art, e.g., by expression from a baculovirus (Brown et al., (1994) *Virology* 198:477-488).

The modifications to the AAV capsid protein according to the present invention are "selective" modifications. This approach is in contrast to previous work with whole subunit or large domain swaps between AAV serotypes (see, e.g., international patent publication WO 00/28004 and Hauck et al., (2003) *J. Virology* 77:2768-2774). In particular embodiments, a "selective" modification results in the insertion and/or substitution and/or deletion of less than about 20, 18, 15, 12, 10, 9, 8, 7, 6, 5, 4 or 3 contiguous amino acids.

The modified capsid proteins and capsids of the invention can further comprise any other modification, now known or later identified.

For example, the AAV capsid proteins and virus capsids of the invention can be chimeric in that they can comprise all or a portion of a capsid subunit from another virus, optionally another parvovirus or AAV, e.g., as described in international patent publication WO 00/28004.

The virus capsid can be a targeted virus capsid comprising a targeting sequence (e.g., substituted or inserted in the viral capsid) that directs the virus capsid to interact with cell-surface molecules present on a desired target tissue(s) (see, e.g., international patent publication WO 00/28004 and Hauck et al., (2003) *J. Virology* 77:2768-2774); Shi et al., *Human Gene Therapy* 17:353-361 (2006) [describing insertion of the integrin receptor binding motif RGD at positions 520 and/or 584 of the AAV capsid subunit]; and U.S. Pat. No. 7,314,912 [describing insertion of the P1 peptide containing an RGD motif following amino acid positions 447, 534, 573 and 587 of the AAV2 capsid subunit]). Other positions within the AAV capsid subunit that tolerate insertions are known in the art (e.g., positions 449 and 588 described by Grifman et al., *Molecular Therapy* 3:964-975 (2001)).

For example, some of the virus capsids of the invention have relatively inefficient tropism toward most target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in international patent publication WO 00/28004. As another possibility one or more non-naturally occurring amino acids as described by Wang et al., *Annu Rev Biophys Biomol Struct.* 35:225-49 (2006)) can be incorporated into the AAV capsid subunit at an orthogonal site as a means of redirecting a low-transduction vector to a desired target tissue(s). These unnatural amino acids can advantageously be used to chemically link molecules of interest to the AAV capsid protein including without limitation: glycans (mannose—dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like. Methods of chemically modifying amino acids are known in the art (see, e.g., Greg T. Hermanson, Bioconjugate Techniques, $1^{st}$ edition, Academic Press, 1996).

In representative embodiments, the targeting sequence may be a virus capsid sequence (e.g., an autonomous parvovirus capsid sequence, AAV capsid sequence, or any other viral capsid sequence) that directs infection to a particular cell type(s).

As another nonlimiting example, a heparin binding domain (e.g., the respiratory syncytial virus heparin binding domain) may be inserted or substituted into a capsid subunit that does not typically bind HS receptors (e.g., AAV 4, AAV5) to confer heparin binding to the resulting mutant.

B19 infects primary erythroid progenitor cells using globoside as its receptor (Brown et aL, (1993) *Science* 262: 114). The structure of B19 has been determined to 8 Å resolution (Agbandje-McKenna et al., (1994) *Virology* 203: 106). The region of the B19 capsid that binds to globoside has been mapped between amino acids 399-406 (Chapman et al., (1993) *Virology* 194:419), a looped out region between 13-barrel structures E and F (Chipman et al., (1996) *Proc. Nat. Acad. Sci. USA* 93:7502). Accordingly, the globoside receptor binding domain of the B19 capsid may be substituted into the AAV capsid protein to target a virus capsid or virus vector comprising the same to erythroid cells.

In representative embodiments, the exogenous targeting sequence may be any amino acid sequence encoding a peptide that alters the tropism of a virus capsid or virus vector comprising the modified AAV capsid protein. In particular embodiments, the targeting peptide or protein may be naturally occurring or, alternately, completely or partially synthetic. Exemplary targeting sequences include ligands and other peptides that bind to cell surface receptors and glycoproteins, such as RGD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., α, β or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, β-endorphin, leu-enkephalin, rimorphin, α-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as α-bungarotoxin, and the like) can be substituted into the capsid protein as a targeting sequence. In a yet further representative embodiment, the AAV capsid protein can be modified by substitution of a "nonclassical" import/export signal peptide (e.g., fibroblast growth factor-1 and -2, interleukin 1, HIV-1 Tat protein, herpes virus VP22 protein, and the like) as described by Cleves (*Current Biology* 7:R318 (1997)) into the AAV capsid protein. Also encompassed are peptide motifs that direct uptake by specific cells, e.g., a FVFLP peptide motif triggers uptake by liver cells.

Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties found on mucins, glycoproteins, and gangliosides, MHC I glycoproteins, carbohydrate components found on membrane glycoproteins, including, mannose, N-acetyl-galactosamine, N-acetyl-glucosamine, fucose, galactose, and the like.

In particular embodiments, a heparan sulfate (HS) or heparin binding domain is substituted into the virus capsid (for example, in an AAV that otherwise does not bind to HS or heparin). It is known in the art that HS/heparin binding is mediated by a "basic patch" that is rich in arginines and/or lysines. In exemplary embodiments, a sequence following the motif BXXB (SEQ ID NO:33) where "B" is a basic residue and X is neutral and/or hydrophobic. As one non-limiting example, BXXB (SEQ ID NO:33) is RGNR (SEQ ID NO:34). In particular embodiments, BXXB (SEQ ID NO:33) is substituted for amino acid positions 262 through 265 in the native AAV2 capsid protein or the corresponding position in the capsid protein of another AAV.

Other nonlimiting examples of suitable targeting sequences include the peptides targeting coronary artery endothelial cells identified by Wier et al., Nature Biotechnology 21:1040-1046 (2003) (consensus sequences NSVRDLG/S (SEQ ID NO:35), PRSVTVP (SEQ ID NO:36), NSVSSXS/A (SEQ ID NO:37); see also Table 2); tumor-targeting peptides as described by Grifman et al., *Molecular Therapy* 3:964-975 (2001) (e.g., NGR, NGRAHA (SEQ ID NO:38)); lung or brain targeting sequences as described by Work et al., *Molecular Therapy* 13:683-693 (2006) (QPEHSST (SEQ ID NO:39), VNTANST (SEQ ID NO:40), HGPMQKS (SEQ ID NO:41), PHKPPLA (SEQ ID NO:42), IKNNEMW (SEQ ID NO:43), RNLDTPM (SEQ ID NO:44), VDSHRQS (SEQ ID NO:45), YDSKTKT (SEQ ID NO:46), SQLPHQK (SEQ ID NO:47), STMQQNT (SEQ ID NO:48), TERYMTQ (SEQ ID NO:49), QPEHSST (SEQ ID NO:50), DASLSTS (SEQ ID NO:51), DLPNKKT (SEQ ID NO:52), DLTAARL (SEQ ID NO:53), EPHQFNY (SEQ ID NO:54), EPQSNHT (SEQ ID NO:55), MSSWPSQ (SEQ ID NO:56), NPKHNAT (SEQ ID NO:57), PDGMRTT (SEQ ID NO:58), PNNNKTT (SEQ ID NO:59), QSTTHDS (SEQ ID NO:60), TGSKQKQ (SEQ ID NO:61), SLKHQAL (SEQ ID NO:62) and SPIDGEQ (SEQ ID NO:63), ; see also Table 1)); vascular targeting sequences described by Hajitou et al., TCM 16:80-88 (2006) (WIFPWIQL (SEQ ID NO:64), CDCRGDCFC (SEQ ID NO:65), CNGRC (SEQ ID NO:66), CPRECES (SEQ ID NO:67), GSL, CTTHWGFTLC (SEQ ID NO:68), CGRRAGGSC (SEQ ID NO:69), CKGGRAKDC (SEQ ID NO:70), and CVPELGHEC (SEQ ID NO:71)); targeting peptides as described by Koivunen et al., *J. Nucl. Med.* 40:883-888 (1999) (CRRETAWAK (SEQ ID NO:72), KGD, VSWFSHRYSPFAVS (SEQ ID NO:73), GYRDGYAGPILYN (SEQ ID NO:74), XXXY*XXX (SEQ ID NO:75) [where Y* is phospho-Tyr], Y*E/MNW (SEQ ID NO:76), RPLPPLP (SEQ ID NO:77), APPLPPR (SEQ ID NO:78), DVFYPYPYASGS (SEQ ID 2Q NO:79), MYWYPY (SEQ ID NO:80), DITWDQLWDLMK (SEQ ID NO:81), CWDDG/LWLC (SEQ ID NO:82), EWCEYLGGYLRCYA (SEQ ID NO:83), YXCXXGPXTWXCXP (SEQ ID NO:84), IEGPTLRQWLAARA (SEQ ID NO:85), LWXXY/W/F/H (SEQ ID NO:86), XFXXYLW (SEQ ID NO:87), SSIISHFRWGLCD (SEQ ID NO:88), MSRPACPPNDKYE (SEQ ID NO:89), CLRSGRGC (SEQ ID NO:90), CHWMFSPWC (SEQ ID NO:91), WXXF (SEQ ID NO:92), CSSRLDAC (SEQ ID NO:93), CLPVASC (SEQ ID NO:94), CGFECVRQCPERC (SEQ ID NO:95), CVALCREACGEGC (SEQ ID NO:96), SWCEPGWCR (SEQ ID NO:97), YSGKWGW (SEQ ID NO:98), GLSGGRS (SEQ ID NO:99), LMLPRAD (SEQ ID NO:100), CSCFRDVCC (SEQ ID NO:101), CRDWSVIC (SEQ ID NO:102), CNGRC (SEQ ID NO:66), and GSL; see also, Tables 1, 2 and 3); and tumor targeting peptides as described by Newton & Deutscher, Phage Peptide Display in Handbook of Experimental Pharmacology, pages 145-163, Springer-Verlag, Berlin (2008) (MARSGL (SEQ ID NO:103), MARAKE (SEQ ID NO:104), MSRTMS (SEQ ID NO:105), KCCYSL (SEQ ID NO:106), WRR, WKR, WVR, WVK, WIK, WTR, WVL, WLL, WRT, WRG, WVS, WVA, MYWGDSHWLQYWYE (SEQ ID NO:107), MQLPLAT (SEQ ID NO:108), EWLS (SEQ ID NO:109), SNEW (SEQ ID NO:110), TNYL (SEQ ID NO:111), WIFPWIQL (SEQ ID NO:112), WDLAWMFRLPVG (SEQ ID NO:113), CTVALPGGYVRVC (SEQ ID NO:114), CVPELGHEC (SEQ ID NO:115), CGRRAGGSC (SEQ ID NO:69), CVAYCIEHHCWTC (SEQ ID NO:116), CVFAHNYDYLVC (SEQ ID NO:117), and CVFTSNYAFC (SEQ ID NO:118), VHSPNKK (SEQ ID NO:119), CDCRGDCFC (SEQ ID NO:65), CRGDGWC (SEQ ID NO:120), XRGCDX (SEQ ID NO:121), PXXS/T (SEQ ID NO:122), CTTHWGFTLC (SEQ ID NO:123), SGKGPRQITAL (SEQ ID NO:124), A9A/Q)(N/A)(L/Y)(TN/M/R)(R/K) (SEQ ID NO:125), VYMSPF (SEQ ID NO:126), MQLPLAT (SEQ ID NO:108), ATWLPPR (SEQ ID NO:127), HTMYYHHYQHHL (SEQ ID NO:128), SEVGCRAGPLQWLCEKYFG (SEQ ID NO:129), CGLLPVGRPDRNVWRWLC (SEQ ID NO:130), CKGQCDRFKGLPWEC (SEQ ID NO:131), SGRSA (SEQ ID NO:132), WGFP (SEQ ID NO:133), LWXXAr (SEQ ID NQ:86) [Ar=Y, W, F, H), XFXXYLW (SEQ ID NO:87), AEPMPHSLNFSQYLWYT (SEQ ID NO:134), WAY(W/F)SP (SEQ ID NO:135), IELLQAR (SEQ ID NO:136), DITWDQLWDLMK (SEQ ID NO:81), AYTKCSRQWRTCMTTH (SEQ ID NO:137), PQNSKIPGPTFLDPH (SEQ ID NO:138), SMEPALPDWWWKMFK (SEQ ID NO:139), ANTPCGPYTHDCPVKR (SEQ ID NO:140), TACHQHVRMVRP (SEQ ID NO:141), VPWMEPAYQRFL (SEQ ID NO:142), DPRATPGS (SEQ ID NO:143), FRPNRAQDYNTN (SEQ ID NO:144), CTKNSYLMC (SEQ ID NO:145), C(R/Q)L/RT(G/N)XXG(A/V)GC (SEQ ID NO:146), CPIEDRPMC (SEQ ID NO:147), HEWSYLAPYPWF (SEQ ID NO:148), MCPKHPLGC (SEQ ID NO:149), RMWPSSTVNLSAGRR (SEQ ID NO:150), SAKTAVSQRVWLPSHRGGEP (SEQ ID NO:151), KSREHVNNSACPSKRITAAL (SEQ ID NO:152), EGFR (SEQ ID NO:153), RVS, AGS, AGLGVR (SEQ ID NO:154), GGR, GGL, GSV, GVS, GTRQGHTMRLGVSDG (SEQ ID NO:155), IAGLATPGWSHWLAL (SEQ ID NO:156), SMSIARL (SEQ ID NO:157), HTFEPGV (SEQ ID NO:158), NTSLKRISNKRIRRK (SEQ ID NO:159), LRIKRKRRKRKKTRK (SEQ ID NO:160), GGG, GFS, LWS, EGG, LLV, LSP, LBS, AGG, GRR, GGH and GTV; see also Table 1).

As yet a further alternative, the targeting sequence may be a peptide that can be used for chemical coupling (e.g., can comprise arginine and/or lysine residues that can be chemically coupled through their R groups) to another molecule that targets entry into a cell.

As another option, the AAV capsid protein or virus capsid of the invention can comprise a mutation as described in WO 2006/066066. For example, the capsid protein can comprise a selective amino acid substitution at amino acid position 263, 705, 708 and/or 716 of the native AAV2 capsid protein or a corresponding change(s) in a capsid protein from another AAV. Additionally, or alternatively, in representative embodiments, the capsid protein, virus capsid or vector comprises a selective amino acid insertion directly following amino acid position 264 of the AAV2 capsid protein or a corresponding change in the capsid protein from other AAV. By "directly following amino acid position X" it is intended that the insertion immediately follows the indicated amino acid position (for example, "following amino acid position 264" indicates a point insertion at position 265 or a larger insertion, e.g., from positions 265 to 268, etc.). The foregoing embodiments of the invention can be used to deliver a heterologous nucleic acid to a cell or subject as described herein. For example, the modified vector can be used to treat a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase) as described herein.

Those skilled in the art will appreciate that for some AAV capsid proteins the corresponding modification will be an insertion and/or a substitution, depending on whether the corresponding amino acid positions are partially or completely present in the virus or, alternatively, are completely absent. Likewise, when modifying AAV other than AAV2, the specific amino acid position(s) may be different than the position in AAV2 (see, e.g., Table 4). As discussed elsewhere herein, the corresponding amino acid position(s) will be readily apparent to those skilled in the art using well-known techniques.

In representative embodiments, the insertion and/or substitution and/or deletion in the capsid protein(s) results in the insertion, substitution and/or repositioning of an amino acid that (i) maintains the hydrophilic loop structure in that region; (ii) an amino acid that alters the configuration of the loop structure; (iii) a charged amino acid; and/or (iv) an amino acid that can be phosphorylated or sulfated or otherwise acquire a charge by post-translational modification (e.g., glycosylation) following 264 in an AAV2 capsid protein or a corresponding change in a capsid protein of another AAV. Suitable amino acids for insertion/substitution include aspartic acid, glutamic acid, valine, leucine, lysine, arginine, threonine, serine, tyrosine, glycine, alanine, proline, asparagine, phenylalanine, tyrosine or glutamine. In particular embodiments, a threonine is inserted or substituted into the capsid subunit. Nonlimiting examples of corresponding positions in a number of other AAV are shown in Table 4 (Position 2). In particular embodiments, the amino acid insertion or substitution is a threonine, aspartic acid, glutamic acid or phenylalanine (excepting AAV that have a threonine, glutamic acid or phenylalanine, respectively, at this position).

TABLE 4

| Serotype | Position 1 | Position 2 |
|---|---|---|
| AAV1 | A263X | T265X |
| AAV2 | Q263X | -265X |
| AAV3a | Q263X | -265X |
| AAV3b | Q263X | -265X |
| AAV4 | S257X | -259X |
| AAV5 | G253X | V255X |
| AAV6 | A263X | T265X |
| AAV7 | E264X | A266X |
| AAV8 | G264X | S266X |
| AAV9 | S263X | S265X |

Where,
X→ mutation to any amino acid
-→ insertion of any amino acid
Note:
Position 2 inserts are indicated by the site of insertion According to this aspect of the invention, in particular embodiments the AAV capsid protein comprises an amino acid insertion following amino acid position 264 in an AAV2, AAV3a or AAV3b capsid protein(s) or in the corresponding position in an AAV2, AAV3a or AAV3b capsid protein that has been modified to comprise non-AAV2, AAV3a or AAV3b sequences, respectively, and/or has been modified by deletion of one or more amino acids (i.e., is derived from AAV2, AAV3a or AAV3b). The amino acid corresponding to position 264 in an AAV (or AAV3a or AAV3b) capsid subunit(s) will be readily identifiable in the starting virus that has been derived from AAV2 (or AAV3a or AAV3b), which can then be further modified according to the present invention. Suitable amino acids for insertion include aspartic acid, glutamic acid, valine, leucine, lysine, arginine, threonine, serine, tyrosine, glycine, alanine, proline, asparagine, phenylalanine, tyrosine or glutamine.

In other embodiments, the AAV capsid protein comprises an amino acid substitution at amino acid position 265 in an AAV1 capsid protein(s), at amino acid position 266 in an AAV8 capsid protein, or an amino acid substitution at amino acid position 265 in an AAV9 capsid protein or in the corresponding position in an AAV1, AAV8 or AAV9 capsid protein that has been modified to comprise non-AAV1, non-AAV8 or non-AAV9 sequences, respectively, and/or has been modified by deletion of one or more amino acids (i.e., is derived from AAV1, AAV8 or AAV9). The amino acid corresponding to position 265 in an AAV1 and AAV9 capsid subunit(s) and position 266 in the AAV8 capsid subunit(s) will be readily identifiable in the starting virus that has been derived from AAV1, AAV8 or AAV9, which can then be further modified according to the present invention. Suitable amino acids for insertion include aspartic acid, glutamic acid, valine, leucine, lysine, arginine, threonine, serine, tyrosine, glycine, alanine, proline, asparagine, phenylalanine, tyrosine or glutamine.

In representative embodiments of the invention, the capsid protein comprises a threonine, aspartic acid, glutamic acid, or phenylalanine following amino acid position 264 of the AAV2 capsid protein (i.e., an insertion) or the corresponding position of another capsid protein.

In other representative embodiments, the modified capsid proteins or virus capsids of the invention further comprise one or more mutations as described in WO 2007/089632 (e.g., an E→K mutation at amino acid position 531 of the AAV2 capsid protein or the corresponding position of the capsid protein from another AAV).

In further embodiments, the modified capsid protein or capsid can comprise a mutation as described in WO 2009/108274.

As another, possibility, the AAV capsid protein can comprise a mutation as described by Zhong et al. (*Virology* 381: 194-202 (2008); *Proc. Nat. Acad. Sci.* 105: 7827-32 (2008)). For example, the AAV capsid protein can comprise a Y→F mutation at amino acid position 730.

The modifications described above can be incorporated into the capsid proteins or capsids of the invention in combination with each other and/or with any other modification 2Q now known or later discovered.

The invention also encompasses virus vectors comprising the modified capsid proteins and capsids of the invention. In particular embodiments, the virus vector is a parvovirus vector (e.g., comprising a parvovirus capsid and/or vector genome), for example, an AAV vector (e.g., comprising an AAV capsid and/or vector genome). In representative embodiments, the virus vector comprises a modified AAV capsid comprising a modified capsid subunit of the invention and a vector genome.

For example, in representative embodiments, the virus vector comprises: (a) a modified virus capsid (e.g., a modified AAV capsid) comprising a modified capsid protein of the invention; and (b) a nucleic acid comprising a terminal repeat sequence (e.g., an AAV TR), wherein the nucleic acid comprising the terminal repeat sequence is encapsidated by the modified virus capsid. The nucleic acid can optionally comprise two terminal repeats (e.g., two AAV TRs).

In representative embodiments, the virus vector is a recombinant virus vector comprising a heterologous nucleic acid encoding a polypeptide or functional RNA of interest. Recombinant virus vectors are described in more detail below.

In particular embodiments, the virus vectors of the invention (i) have reduced transduction of liver as compared with the level of transduction by a virus vector without the modified capsid protein; (ii) exhibit enhanced systemic transduction by the virus vector in an animal subject as compared with the level observed by a virus vector without the modified capsid protein; (iii) demonstrate enhanced movement across endothelial cells as compared with the level of movement by a virus vector without the modified capsid protein, and/or (iv) exhibit a selective enhancement in transduction of muscle tissue (e.g., skeletal muscle, cardiac muscle and/or diaphragm muscle), and/or (v) reduced transduction of brain tissues (e.g., neurons) as compared with the level of transduction by a virus vector without the modified capsid protein. In particular embodiments, the virus vector has systemic transduction toward muscle, e.g., transduces multiple skeletal muscle groups throughout the body and optionally transduces cardiac muscle and/or diaphragm muscle.

Further, in embodiments of the invention, the modified virus vectors demonstrate efficient transduction of target tissues. In general, when $X^1$-$X^2$-$X^3$-$X^4$-$X^5$-$X^6$ (SEQ ID NO:1) is introduced into an AAV capsid protein, the order of transduction efficiency (e.g., for muscle tissue including skeletal muscle, cardiac muscle and/or diaphragm muscle) appears to be:

| | |
|---|---|
| QXXTXP | (SEQ ID NO: 161) |
| >NXXTXP | (SEQ ID NO: 162) |
| >SXXAXP | (SEQ ID NO: 163) |
| >AXXAXA | (SEQ ID NO: 32) | when the modified capsid protein is incorporated into a virus vector (e.g., an AAV vector comprising a modified AAV capsid comprising the modified AAV capsid protein of the invention).

Those skilled in the art will appreciate that some particular modifications may deviate from this general rule without departing from the scope of the present invention. For example, certain amino acids in the "X" positions may affect transduction efficiency. As one illustration, a proline (P) in one of the "X" positions may reduce transduction efficiency.

In particular embodiments, efficient muscle transduction (skeletal, cardiac and/or diaphragm) is achieved (e.g., by an AAV vector comprising a modified AAV capsid comprising the modified AAV capsid protein of the invention) when $X^1$-$X^2$-$X^3$-$X^4$-$X^5$-$X^6$ (SEQ ID NO:1) is QXXTXP (SEQ ID NQ:161) or NXXTXP (SEQ ID NO:162). In particular embodiments, X is not selected from P, C and/or W.

It will be understood by those skilled in the art that the modified capsid proteins, virus capsids and virus vectors of the invention exclude those capsid proteins, capsids and virus vectors that have the indicated amino acids at the specified positions in their native state (i.e., are not mutants).

Methods of Producing Virus Vectors.

The present invention further provides methods of producing the inventive virus vectors. In one representative embodiment, the present invention provides a method of producing a virus vector, the method comprising providing to a cell: (a) a nucleic acid template comprising at least one TR sequence (e.g., AAV TR sequence), and (b) AAV sequences sufficient for replication of the nucleic acid template and encapsidation into AAV capsids (e.g., AAV rep sequences and AAV cap sequences encoding the AAV capsids of the invention). Optionally, the nucleic acid template further comprises at least one heterologous nucleic acid sequence. In particular embodiments, the nucleic acid template comprises two AAV ITR sequences, which are located 5' and 3' to the heterologous nucleic acid sequence (if present), although they need not be directly contiguous thereto.

The nucleic acid template and AAV rep and cap sequences are provided under conditions such that virus vector comprising the nucleic acid template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell. As another option, the cell can be a trans-complementing packaging cell line that provides functions deleted from a replication-defective helper virus, e.g., 293 cells or other E1 a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so.

The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) Curr. Top. Microbiol. Immun. 158: 67).

As a further alternative, the rep/cap sequences may be stably incorporated into a cell.

Typically the AAV rep/cap sequences will not be flanked by the TRs, to prevent rescue and/or packaging of these sequences.

The nucleic acid template can be provided to the cell using any method known in the art. For example, the template can be supplied by a non-viral (e.g., plasmid) or viral vector. In particular embodiments, the nucleic acid template is supplied by a herpesvirus or adenovirus vector (e.g., inserted into the E1a or E3 regions of a deleted adenovirus). As another illustration, Palombo et al., (1998) J. Virology 72:5025, describes a baculovirus vector carrying a reporter gene flanked by the AAV TRs. EBV vectors may also be employed to deliver the template, as described above with respect to the rep/cap genes.

In another representative embodiment, the nucleic acid template is provided by a replicating rAAV virus. In still other embodiments, an AAV provirus comprising the nucleic acid template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., (1997) Nature Med. 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further can further comprise the nucleic acid template. The AAV rep/cap sequences and/or the rAAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the rAAV template can be provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template can be provided as a separate replicating viral vector. For example, the rAAV template can be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by TRs so that these sequences are not packaged into the AAV virions.

Zhang et al., ((2001) Gene Ther. 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) Gene Therapy 6:986 and WO 00/17377.

As a further alternative, the virus vectors of the invention can be produced in insect cells using baculovirus vectors to deliver the rep/cap genes and rAAV template as described, for example, by Urabe et al., (2002) Human Gene Therapy 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) Gene Therapy 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Recombinant Virus Vectors.

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells. Any heterologous nucleic acid sequence(s) of interest may be delivered in the virus vectors of the present invention. Nucleic acids of interest include nucleic acids encoding polypeptides, including therapeutic (e.g., for medical or veterinary uses) or immunogenic (e.g., for vaccines) polypeptides.

Therapeutic polypeptides include, but are not limited to, cystic fibrosis transmembrane regulator protein (CFTR), dystrophin (including mini- and micro-dystrophins, see, e.g., Vincent et al., (1993) *Nature Genetics* 5:13Q; U.S. Patent Publication No. 2003/017131; International publication WO/2008/088895, Wang et al., *Proc. Natl. Acad. Sci. USA* 97:13714-13719 (2000); and Gregorevic et al., *Mol. Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al., (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $α_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, μlatelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor -α and -β, and the like), lysosomal acid α-glucosidase, α-galactosidase A, receptors (e.g., the tumor necrosis growth factorα soluble receptor), S100A1, parvalbumin, adenylyl cyclase type 6, a molecule that modulates calcium handling (e.g., $SERCA_{2A}$, Inhibitor 1 of PP1 and fragments thereof [e.g., WO 2006/029319 and WO 2007/100465]), a molecule that effects G-protein coupled receptor kinase type 2 knockdown such as a truncated constitutively active bARKct, anti-inflammatory factors such as RAP, anti-myostatin proteins, aspartoacylase, monoclonal antibodies (including single chain monoclonal antibodies; an exemplary Mab is the Herceptin® Mab), neuropeptides and fragments thereof (e.g., galanin, Neuropeptide Y (see, U.S. Pat. No. 7,071,172), angiogenesis inhibitors such as Vasohibins and other VEGF inhibitors (e.g., Vasohibin 2 [see, WO JP2006/073052]). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al., *Nature Biotechnology* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Optionally, the heterologous nucleic acid encodes a secreted polypeptide (e.g., a polypeptide that is a secreted polypeptide in its native state or that has been engineered to be secreted, for example, by operable association with a secretory signal sequence as is known in the art).

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) including siRNA, shRNA or miRNA that mediate gene silencing (see, Sharp et al., (2000) *Science* 287:2431), and other non-translated RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., *J. Gene Med.* 10:132-142 (2008) and Li et al., *Acta Pharmacol Sin.* 26:51-55 (2005)); phospholamban inhibitory or dominant-negative molecules such as phospholamban S16E (e.g., to treat cardiovascular disease, see, e.g., Hoshijima et al. *Nat. Med.* 8:864-871 (2002)), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a modified capsid of the invention.

The virus vector may also comprise a heterologous nucleic acid that shares homology with and recombines with a locus on a host chromosome. This approach can be utilized, for example, to correct a genetic defect in the host cell.

The present invention also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al., (1994) *Proc. Nat. Acad. Sci USA* 91:8507; U.S. Pat. No. 5,916,563 to Young et al., U.S. Pat. No. 5,905,040 to Mazzara et al., U.S. Pat. Nos. 5,882,652, 5,863,541 to Samulski et al.). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present invention.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.*, 180:347; Kawakami et al., (1994) *Cancer Res.* 54:3124), MART-1, gp100 MAGE-1, MAGE-2, MAGE-3, CEA, TRP-1, TRP-2, P-15, tyrosinase (Brichard et al., (1993) *J. Exp. Med.* 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic disorders, congenital emphysema (α1-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1) and fragments thereof (e.g., I1C), serca2a, zinc finger proteins that regulate the phospholamban gene, Barkct, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as RAP and TNFa soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

The invention can also be used to produce induced pluripotent stem cells (iPS). For example, a virus vector of the invention can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like. Nucleic acids encoding factors associated with stem cells are known in the art. Nonlimiting examples of such factors associated with stem cells and pluripotency include Oct-3/4, the SOX family (e.g., SOX1, SOX2, SOX3 and/or SOX15), the Klf family (e.g., Klf1, Klf2, Klf4 and/or Klf5), the Myc family (e.g., C-myc, L-myc and/or N-myc), NANOG and/or LIN28.

The invention can also be practiced to treat and/or prevent a metabolic disorder such as diabetes (e.g., insulin), hemophilia (e.g., Factor IX or Factor VIII), a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase).

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present invention permit the treatment and/or prevention of genetic diseases.

The virus vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

In addition, virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces. the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described below.

The virus vectors of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid (e.g., as described above).

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector expressing a cancer cell antigen according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration.

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles, adults and geriatric subjects.

In representative embodiments, the subject is "in need of" the methods of the invention.

In particular embodiments, the present invention provides a pharmaceutical composition comprising a virus vector and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, optionally at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendricytes), lung cells, cells of the eye (including retinal cells, retinal pigment epithelium, and corneal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (I.e., a "recipient" subject).

Suitable cells for ex vivo nucleic acid delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vector and/or virus capsid to subjects. Administration of the virus vectors and/or capsids according to the present invention to a human subject or an animal in need thereof can be by any means known in the art.

Optionally, the virus vector and/or capsid is delivered in a treatment effective or prevention effective dose in a pharmaceutically acceptable carrier.

The virus vectors and/or capsids of the invention can further be administered to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^3$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector and/or capsid can be delivered to skeletal muscle by intravenous administration, intra-arterial administration, intraperitoneal administration, limb perfusion, (optionally, isolated limb perfusion of a leg and/or arm; see, e.g., Arruda et al., (2005) *Blood* 105: 3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration). In embodiments of the invention, the virus vectors and/or capsids of the invention can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Delivery to a target tissue can also be achieved by delivering a depot comprising the virus vector and/or capsid. In representative embodiments, a depot comprising the virus vector and/or capsid is implanted into skeletal, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector and/or virus capsid according to the present invention is administered to skeletal muscle, diaphragm muscle and/or cardiac muscle (e.g., to treat and/or prevent muscular dystrophy, heart disease [for example, PAD or congestive heart failure]).

In representative embodiments, the invention is used to treat and/or prevent disorders of skeletal, cardiac and/or diaphragm muscle.

In a representative embodiment, the invention provides a method of treating and/or preventing muscular dystrophy in a subject in need thereof, the method comprising: administering a treatment or prevention effective amount of a virus vector of the invention to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-α2, α-sarcoglycan, β-sarcoglycan, γ-sarcoglycan, δ-sarcoglycan, IGF-1, an antibody or antibody fragment against myostatin or myostatin propeptide, and/or RNAi against myostatin. In particular embodiments, the virus vector can be administered to skeletal, diaphragm and/or cardiac muscle as described elsewhere herein.

Alternatively, the invention can be practiced to deliver a nucleic acid to skeletal, cardiac or diaphragm muscle, which is used as a platform for production of a polypeptide (e.g., an enzyme) or functional RNA (e.g., RNAi, microRNA, antisense RNA) that normally circulates in the blood or for systemic delivery to other tissues to treat and/or prevent a disorder (e.g., a metabolic disorder, such as diabetes [e.g., insulin], hemophilia [e.g., Factor IX or Factor VIII], a mucopolysaccharide disorder [e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.] or a lysosomal storage disorder such as Gaucher's disease [glucocerebrosidase] or Fabry disease [α-galactosidase A] or a glycogen storage disorder such as Pompe disease [lysosomal acid α glucosidase]). Other suitable proteins for treating and/or preventing metabolic disorders are described herein. The use of muscle as a platform to express a nucleic acid of interest is described in U.S. Patent publication US 2002/0192189.

Thus, as one aspect, the invention further encompasses a method of treating and/or preventing a metabolic disorder in a subject in need thereof, the method comprising:

administering a treatment or prevention effective amount of a virus vector of the invention to skeletal muscle of a subject, wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory of the invention, according to this embodiment, administration to the skeletal muscle can result in secretion of the polypeptide into the systemic circulation and delivery to target tissue(s). Methods of delivering virus vectors to skeletal muscle is described in more detail herein.

The invention can also be practiced to produce antisense RNA, RNAi or other functional RNA (e.g., a ribozyme) for systemic delivery.

The invention also provides a method of treating and/or preventing congenital heart failure or PAD in a subject in need thereof, the method comprising administering a treatment or prevention effective amount of a virus vector of the invention to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1) and fragments thereof (e.g., I1C), RNAi against phospholamban; a phospholamban inhibitory or dominant-negative molecule such as phospholamban S16E, a zinc finger protein that regulates the phospholamban gene, β2-adrenergic receptor, β2-adrenergic receptor kinase (BARK), PI3 kinase, calsarcan, a β-adrenergic receptor kinase inhibitor (βARKct), inhibitor 1 of protein phosphatase 1 and fragments thereof (e.g., I1C), S100A1, parvalbumin, adenylyl cyclase type 6, a molecule that effects G-protein coupled receptor kinase type 2 knockdown such as a truncated constitutively active bARKct, Pim-1, PGC-1α, SOD-1, SOD-2, EC-SOD, kallikrein, HIF, thymosin-β4, mir-1, mir-133, mir-206, mir-208 and/or mir-26a.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. US-2004-0013645-A1).

The virus vectors and/or virus capsids disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors and virus capsids can be administered to tissues of the CNS (e.g., brain, eye) and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive deliver vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are known in the art.

In particular embodiments, the vector can comprise a secretory signal as described in U.S. Pat. No. 7,071,172.

In representative embodiments of the invention, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201,898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Having described the present invention, the same will be explained in greater detail in the following examples, which are included herein for illustration purposes only, and which are not intended to be limiting to the invention.

EXAMPLES

The inventors have exploited the plasticity of the heparin binding domain on AAV2 to generate synthetic AAV strains with unique systemic tissue tropisms. Using a domain swapping approach, the inventors substituted a linear heparin sulfate-binding motif on the AAV serotype 2 capsid with corresponding amino acid residues from various other AAV serotypes and variants as well as synthetic strains (see Table 5). Attenuation of heparin sulfate binding through this comprehensive mutagenesis approach yielded three groups of chimeric AAV capsids with overlapping phenotypes: (a) AAV mutants capable of systemic spread; (b) AAV mutants detargeted from the liver and (c) AAV mutants with low level transduction.

TABLE 5

| Hexapeptide motif (585-590) | SEQ ID NO: | AAV strain(s) | Tropism** | Transduction Efficiency | |
|---|---|---|---|---|---|
| | | | | Muscle | Liver |
| RGNRQA | 3 | AAV2 | Liver | – | ++ |
| SSSTDP | 4 | 2i1; 2i6 | N/A | – | – |
| SSNTAP | 5 | 2i3a/3b | N/A | – | – |
| SNSNLP | 6 | 2i4 | N/A | – | – |
| SSTTAP | 7 | 2i5 | N/A | – | – |
| SAQAQA | 10 | 2i9 | N/A | – | – |
| QQNTAP | 9 | 2i8; 2irh43; 2irh49-53; 2irh57; 2irh58; 2irh64 | Systemic Muscle | ++++ | + |
| QANTGP | 11 | 2i10; 2irh40 | Systemic Muscle | ++ | – |
| QTNTGP | 23 | 2irh38 | Systemic Muscle | ++ | – |
| QTNGAP | 24 | 2irh2 | Systemic Muscle | + | – |
| NATTAP | 12 | 2i11; 2i12; 2irh32-34 | Systemic Muscle | + | – |
| QQNTAP | 9 | AAV8 | Systemic (Multi-organ) | ++++ | ++++ |

*(–) No transduction observed, (+) one relative log unit;

**Based on image analysis, genome copy number and/or luciferase expression levels.

The inventors generated a panel of chimeric AAV2-derived capsids, deficient in heparin binding, by swapping the 585-RGNRQA-590 heparin binding domain with amino acid residues derived from the corresponding capsid domain on various AAV isolates. In vivo screening of the AAV vector panel following intravenous administration in mice was carried out through live animal bioluminescent imaging. This approach resulted in the discovery of several chimeric AAV capsids displaying distinct systemic transduction profiles as well as mutants with only low-level transduction for any tissue type.

Figure 4:
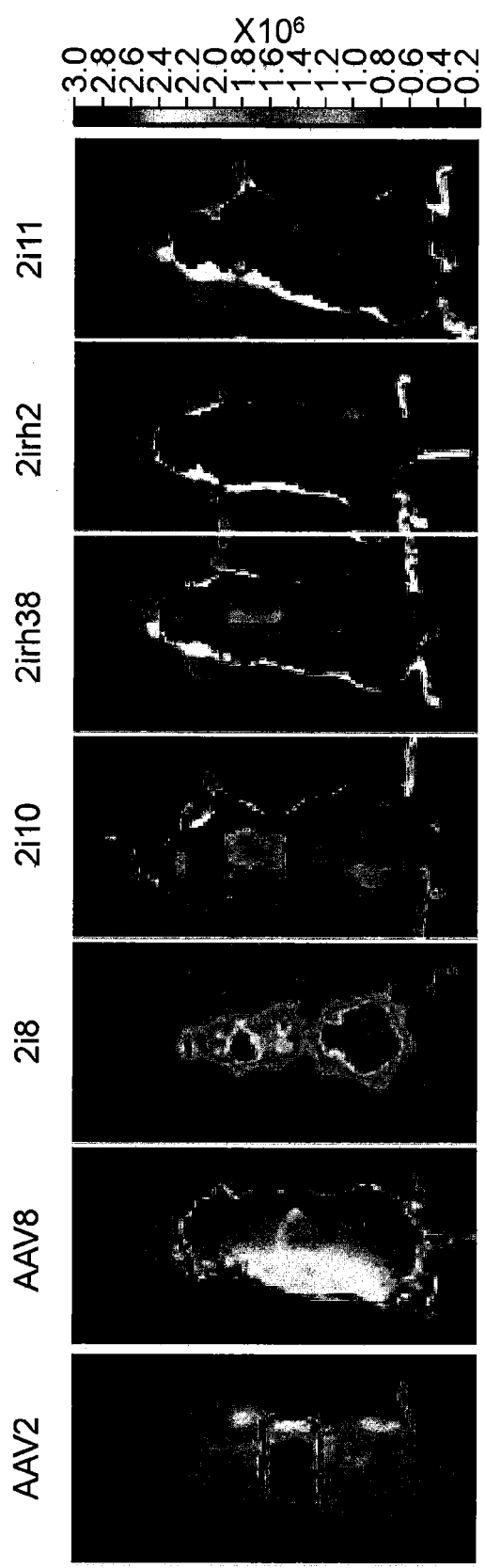

One chimeric vector, AAV2i8, selectively transduces cardiac as well as skeletal muscle tissue with high efficiency. The AAV2i8 capsid, which is detargeted from the liver, appears to traverse the blood vasculature to efficiently transduce a wide variety of muscle groups. Comparative analysis of capsid surface topologies reveals a chimeric footprint at the three-fold axis of symmetry on the AAV2i8 capsid (data not shown) that may contribute to the observed atypical transduction profile. The chimeric nature of AAV2i8 is corroborated by the observation that AAV2i8 capsids are only modestly neutralized when exposed to anti-AAV2 serum or human serum (see Tables 6 and 7). In addition to being de-targeted from the liver, AAV2i8 demonstrates an ability to traverse the blood vasculature and transduce cardiac and skeletal muscle with high efficiency comparable to AAV8 vectors.

TABLE 6

| Vector | Sera | AAV2 |
|---|---|---|
| AAV2 | | 1:2500 |
| AAV8 | | <1:10 |
| AAV2i8 | | 1:40 |

TABLE 7

| | NA titer to AAV | | |
|---|---|---|---|
| Subject ID | AAV2 | AAV8 | AAV2i8 |
| CHI 2-17 | 256 | <20 (8) | <20 (16) |
| DEN 4-8 | 256 | <20 (8) | <20 (8) |
| DEN 20-7 | 64 | <20 (<2) | <20 (<2) |
| IND 1-5 | 512 | <20(16) | <20(16) |

Example 1

Generation of AAV2 Inner Loop Mutants (AAV2i series)

The heparin binding motif, 585-RGNRQA-590 (SEQ ID NO:3), is located within loop IV at the three-fold axis of symmetry on the AAV2 capsid surface. Through site-directed mutagenesis, the hexapeptide motif was substituted with corresponding amino acids (located adjacent to a conserved glutamine residue) from different AAV serotypes and non-human primate isolates to generate a series of AAV2i mutants (see Table 5). Titers of all AAV2i mutants were comparable to that of parental AAV2 vectors.

Example 2

AAV2i Mutants are Deficient in Heparin Binding and Transduction In Vitro

In the current study, AAV2i mutants containing amino acid residues Q, A, S or N in position 585 and T, N, A or G in position 588 were unable to bind heparin as demonstrated by affinity column binding assays. Representative elution profiles of parental AAV2 capsids and one such mutant, AAV2i8, are shown in FIG. 1, panel A. While the AAV2 peak fraction elutes at ~300 mM NaCl, the AAV2i8 capsid is unable to bind heparin under physiological conditions (pH 7.4, 150 mM NaCl).

In general, AAV2i mutants were deficient by several orders of magnitude at transducing HEK293 cells in comparison with the parental AAV2 vector. Several representative examples are shown in FIG. 1, panel B. This observation can be attributed to the inability of AAV2i mutants to bind cell surface heparin sulfate proteoglycans. Based on the rationale that certain AAV serotypes (1, 4, 5 and 6) utilize N- or O-linked sialic acid as a primary receptor, we also determined whether modest transduction efficiencies displayed by AAV2i mutants can be explained by sialic acid binding. However, as shown in FIG. 1, panel B, treatment of HEK293 cells with sialidase to remove surface-exposed sialic acid groups did not affect transduction efficiency of AAV2i1, 2i4 or 2i5. Transduction efficiencies of parental AAV2, AAV2i7 and 2i8 vectors also remain unaffected. In contrast, transduction by AAV4, which utilizes O-linked sialic acid as a primary receptor decreased by an order of magnitude. Lastly, no significant advantage was noted in the ability of AAV2i mutants to infect heparin sulfate-negative CHOpgsD cells, which are relatively non-permissive to parental AAV2 vectors (FIG. 1, panel C). Modest transduction levels by AAV2 can possibly be attributed to non-specific interaction with chondroitin sulfate, over-expressed on the surface of CHOpgsD cells.

Example 3

AAV2i8 Displays a Distinct Phenotype In Vivo

Despite the low levels of transduction observed in vitro, we determined the tissue tropism profiles of AAV2i mutants in normal Balb/C mice using live animal bioluminescence imaging. AAV2i mutants 1, 3, 4, 5, 7, 8 and parental AAV2 vectors packaging the firefly luciferase transgene driven by the cytomegalovirus (CMV) promoter were injected at a dose of $1\times10^{10}$ vector genomes per mouse, through intramuscular route into the right hind limb or through intravenous route through the tail vein.

In general, most AAV2i mutants appeared to exhibit low-level transduction based on bioluminescent images obtained 1 week post-administration (FIG. 2, panels A and B). One notable exception was AAV2i8.

Unlike AAV2, which displays preferential tropism for the murine liver, AAV2i8 demonstrates a systemic transduction profile. AAV2i8 transduces murine hind limb skeletal muscle with moderate efficiency following intramuscular administration (FIG. 2, panel A). Following intravenous administration, AAV2i8 displayed a systemic transduction profile (FIG. 2, panel B) regardless of the duration of gene expression or whether the vector was administered via the tail vein or the portal vein (FIG. 3).

Example 4

AAV2i Mutants with a 585-Q/NXXTXP-590 (SEQ ID NO:164) Motif Display a Systemic Transduction Profile Following preliminary observations with AAV2i8 vectors in vivo, we administered several AAV2i mutants with 585-

QXXTXP-590 SEQ ID NO:161) or 585-NXXTXP-590 (SEQ ID NO:162) motifs as well as parental AAV2 and AAV8 vectors as controls in mice. All vectors packaging the luciferase transgene driven by the chicken beta-actin (CBA) promoter were administered at a dose of 5×10$^{10}$ vector genomes per mouse and live animal images obtained 10 days post-administration. As shown in FIG. 4, AAV2i mutants with residues Q/N585, T588 and P590 appear to display systemic transduction profiles similar to AAV8 vectors. The significantly higher transduction efficiency exhibited by AAV2i8 in comparison to AAV2i10, AAV2i11, AAV2irh.2 and AAV2irh.38 vectors highlights the subtle synergy between residues located within the hexapeptide motif in conferring systemic tissue tropism. In contrast, AAV2 vectors display a preferential tropism for liver as established earlier.

Figure 5:
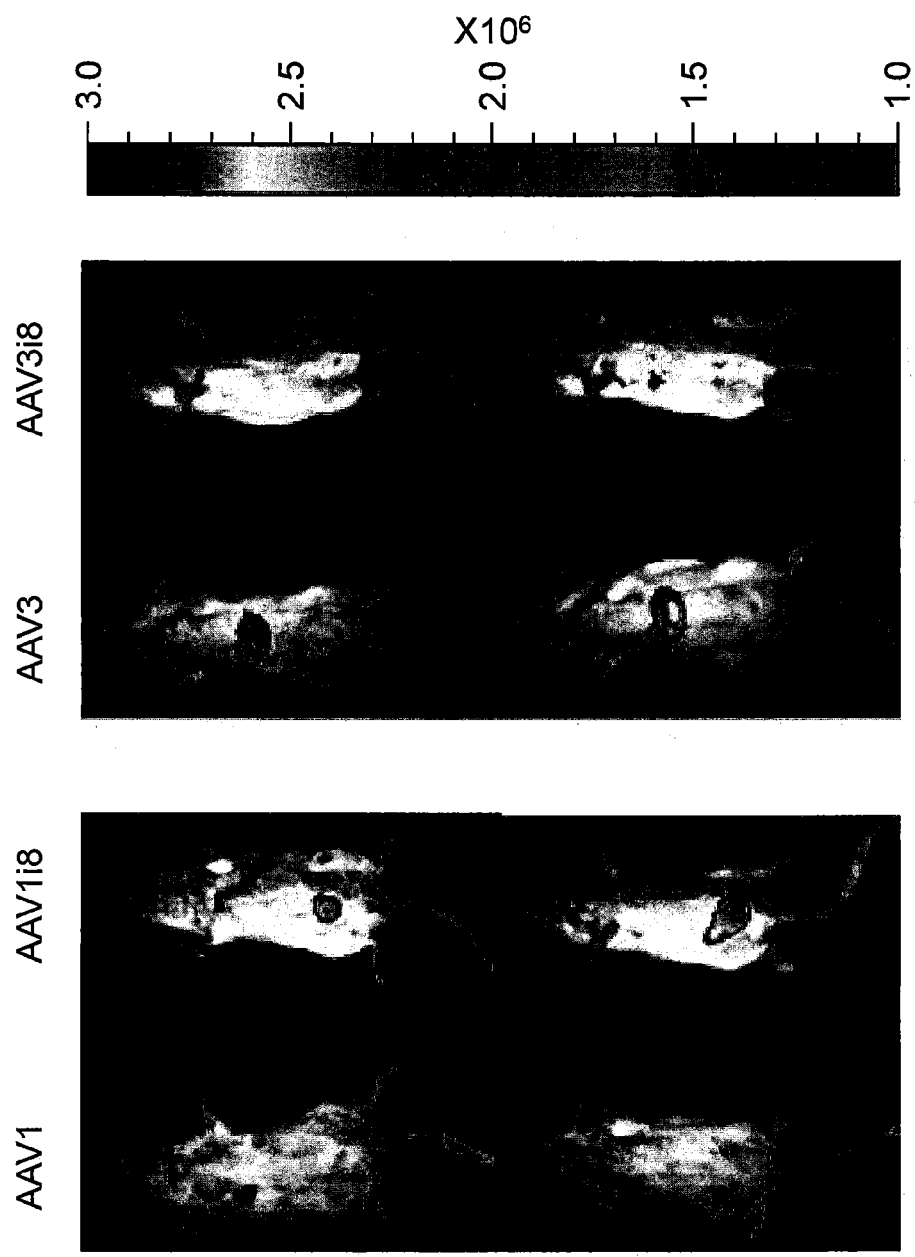

It is noteworthy to mention that the 585-QQNTAP-590 (SEQ ID NO:9) motif was unable to confer systemic tropism when incorporated into the corresponding domain on AAV1 or AAV3 capsids (FIG. 5).

Example 5

AAV2i8 is Detargeted from the Liver and Displays Selective Muscle Tropism

Figure 11:
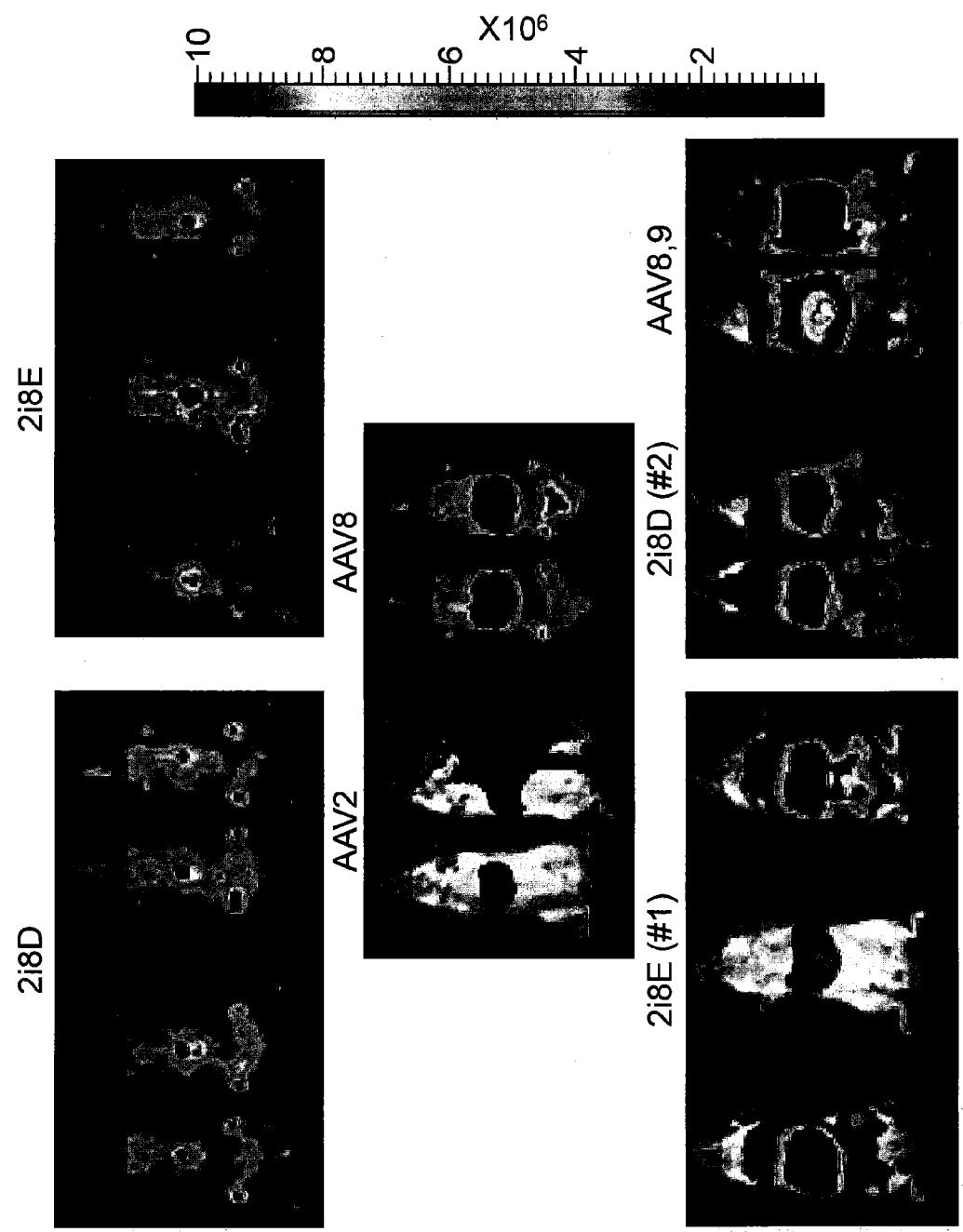

Based on relatively similar systemic transduction patterns displayed by the aforementioned mutants following intravenous administration in mice, the lab-derived AAV2i8 strain was chosen as a lead candidate for further characterization. In order to determine the transduction efficiency of AAV2i8 in comparison with parental AAV2 and AAV8 vectors, we quantified luciferase transgene expression and genome copy numbers in cardiac, skeletal muscle and liver tissue lysates at 2 weeks post-administration. As shown in FIG. 6A, AAV8 vectors ubiquitously transduced muscle and liver tissue with high efficiency corroborating the systemic transduction profile observed earlier in FIG. 4. Although less efficient than AAV8, AAV2 vectors preferentially transduced liver and only displayed modest transduction levels in muscle tissue. In contrast, AAV2i8 appears to preferentially transduce muscle tissue with high efficiency similar to AAV8 and is simultaneously detargeted from the liver.

The aforementioned luciferase transgene expression profiles are corroborated by biodistribution of vector genome copies in muscle and liver tissues as determined by Q-PCR (FIG. 6B). In the case of AAV2 and AAV8 vectors, a disproportionately high amount of vector genome copies were recovered from liver tissue in comparison to cardiac or skeletal muscle tissue. The latter observation attests to the preferential liver tropism of AAV2 and AAV8 vectors, although AAV8 also appears to transduce muscle tissue with similar efficiency. In the case of AAV2i8, the lack of sequestration of vector genomes in liver tissue and redirection to muscle tissue is particularly striking. Low levels of AAV2i8 vector genome copies were recovered from other major organs such as brain, lung and spleen (data not shown).

Notable exceptions to AAV2i mutants containing the 585-Q/NXXTXP-590 (SEQ ID NO:164) motif, include AAV2i7 (585-AANTAA-590, SEQ ID NO:8) and AAV2irh.36 (585-SSTAGP-590, SEQ ID NO:13) that also displayed a systemic transduction profile. Despite efficient liver detargeting, AAV2i7 transduces muscle tissue with significantly lower efficiency in comparison to AAV2i8 and AAV8 vectors (data not shown). Interestingly, mutation of 585-AANTAA-590 (SEQ ID NO:8) to 585-QQNTAA-590 (SEQ ID NO:14, lacking the P590 residue in AAV2i8) restores liver tropism and decreases overall transduction efficiency. On the other hand, while AAV2irh.36 displays moderate systemic transduction efficiency, this vector appears to have retained significant liver tropism (data not shown). Mutation of 585-SSTAGP-590 (SEQ ID NO:13) to 585-PSTAGP-590 (SEQ ID NO:15) in AAV2irh.36 resulted in very poor transduction in vivo. The latter observations suggest that in general, attenuation of heparin binding can result in liver detargeting and systemic dissemination of AAV2-derived vectors. However, specific domains such as the 585-Q/NXXTXP-590 (SEQ ID NO:164) motif might confer highly efficient systemic transduction.

Example 6

AAV2i8 Transduces a Wide Range of Muscle Groups

In order to determine the extent of the global spread of AAV2i8 following intravenous administration, we harvested different muscle groups from Balb/C mice at 4 weeks post-administration. As shown in FIG. 7, AAV2i8 transduces a wide range of muscle groups in the murine forearms and hind legs as well as intercostal, facial and abdominal muscles. Notably, cardiac and diaphragm muscle are transduced by AAV2i8 with high efficiency, whereas other major organs, such as the brain, lung and spleen, are transduced with low efficiency. These results distinguish the tissue tropism of the AAV2i8 capsid from that of any naturally occurring AAV serotype or isolate that has thus far been characterized (FIG. 8).

Example 7

AAV2i8 Traverses Blood Vessels with High Efficiency

An isolated hind limb perfusion technique was used to examine the efficiency with which AAV2i8 traverses the blood vessel barrier. AAV2i8 transduced hind limb skeletal muscle as efficiently as AAV8 at low volume of injection, at moderate and high vector dosage (FIG. 9, panel A). At low vector dose, AAV8 displayed three- to tenfold increases in transduction efficiency at higher volumes of injection. However, AAV2i8 traversed blood vessels and transduced underlying skeletal muscle with high efficiency regardless of the volume of injection.

The atypical tropism of AAV2i8 distinguishes it from natural AAV serotypes 8 and 9 and suggests that engineered AAV vectors can be tailored for specific clinical applications. AAV2i8 showed markedly reduced blood clearance and appears to persist well over 48 hours in blood (FIG. 9, panel B). Moreover, muscle-specific luciferase transgene expression levels increased gradually over the course of several weeks (FIG. 10). In contrast, AAV8 vector genome copy number rapidly decreased, approaching background levels within the same time period. These results and previous observations that other AAV serotypes with systemic tissue tropism have long circulation half-lives suggest that strategies to manipulate blood circulation time of AAV capsids might afford control over vector tropism.

Example 8

Insertion/Substitution at Position 265 of the Capsid Protein Restores Liver Tropism to AAV2i8

New vectors were generated in which an aspartic acid or glutamic acid was inserted following amino acid position 264 (numbering with respect to the AAV2 VP1 capsid subunit) of the AAV2i8 vector (2i8D and 2i8E, respectively). Female (FIG. 11; top) and male (FIG. 11; bottom) BALB/c mice were injected intravenously via the tail vein with AAV2, AAV8, AAV9, 2i8D or 2i8E vectors (dose $1 \times 10^{11}$ vg in 200 µl PBS) packaging the CBA-Luc cassette. Live animal bioluminescent imaging was used to evaluate vector tropism and luciferase expression 4 days after injection. The levels of systemic transduction for the 2i8D and 2i8E vectors were similar to those observed for the recombinant AAV8 and AAV9 vectors (FIG. 11). Further, although there were some gender-dependent expression patterns, liver transduction efficiency was, in general, similar between the 2i8D and 2i8E vectors as compared with the AAV8 and AAV9 vectors (FIG. 11). Thus, although substitution of the QQNTAP (SEQ ID NO:9) motif at positions 585 through 590 (inclusive) of the AAV2 capsid protein results in detargeting from the liver as compared with AAV2 or AAV8 vectors, the additional insertion of a aspartic acid (D) or glutamic acid (E) following amino acid 264 was able to restore liver tropism to levels similar to those seen with AAV8 or AAV9. Moreover, the 2i8D and 2i8E vectors were also able to maintain wide-spread muscle tropism as seen with vector AAV2i8.

In further experiments, other amino acids are inserted following position 264 in the AAV2i8 vector (e.g., valine, leucine, lysine, arginine, threonine, serine, tyrosine, glycine, alanine, proline, asparagine, phenylalanine, tyrosine or glutamine), and transduction patterns and gene expression are evaluated as described above.

In other studies, the QQNTAP (SEQ ID NO:9) motif is substituted at the positions corresponding to amino acids 585 through 590 (inclusive) of the AAV capsid subunit from other AAV with and without the addition of an amino acid insertion/substitution at position 265 (e.g., aspartic acid, glutamic acid, alanine, leucine, lysine, arginine, threonine, serine, tyrosine, glycine, alanine, proline, asparagine, phenylalanine, tyrosine or glutamine), and transduction patterns and gene expression are evaluated as described above.

Example 9

Studies in Brain

In a further study, an AAV2 vector having an aspartic acid inserted following position 264 of the capsid protein was generated (AAV2-265D). Rats received AAV2, 2i8, AAV2-265D or 2i8D vector (described in Example 8) expressing a GFP transgene by stereotactic injection into the brain. AAV2-265D demonstrated higher levels of GFP expression as compared with AAV2; however, neither vector exhibited much spread beyond the site of injection (data not shown). In contrast, injection of the 2i8 vector into brain resulted in only low levels of transduction as assessed by GFP expression. Incorporation of the aspartic acid at position 265 in vector 2i8D restored transduction in the brain and also resulted in much more extensive spread from the injection site throughout the brain (e.g., hippocampus and striatum) as compared with equivalent amounts of the AAV2 and AAV2-265D vectors (data not shown). For all vectors, neurons were the primary cell type transduced (data not shown).

In further experiments, other amino acids are inserted following position 264 in the AAV2i8 vector (e.g., glutamic acid, valine, leucine, lysine, arginine, threonine, serine, tyrosine, glycine, alanine, proline, asparagine, phenylala-nine, tyrosine or glutamine), and transduction patterns, vector spread, and gene expression in the brain are evaluated as described above.

In other studies, the QQNTAP (SEQ ID NO:9) motif is substituted at the positions corresponding to amino acids 585 through 590 (inclusive) of the AAV capsid subunit from other AAV with and without the addition of an amino acid insertion/substitution at position 265 (e.g., aspartic acid, glutamic acid, alanine, leucine, lysine, arginine, threonine, serine, tyrosine, glycine, alanine, proline, asparagine, phenylalanine, tyrosine or glutamine), and transduction patterns, vector spread, and gene expression in the brain are evaluated as described above.

Example 10

Summary of Characteristics of AAV2i Mutants

AAV2i mutants from this study were unable to bind heparin (FIG. 1, panel A). The inability to bind heparin results in significant decrease in transduction efficiency in vitro as well as in vivo following intramuscular as well as intravenous administration in mice (FIG. 2, panels A and B).

Figure 2:
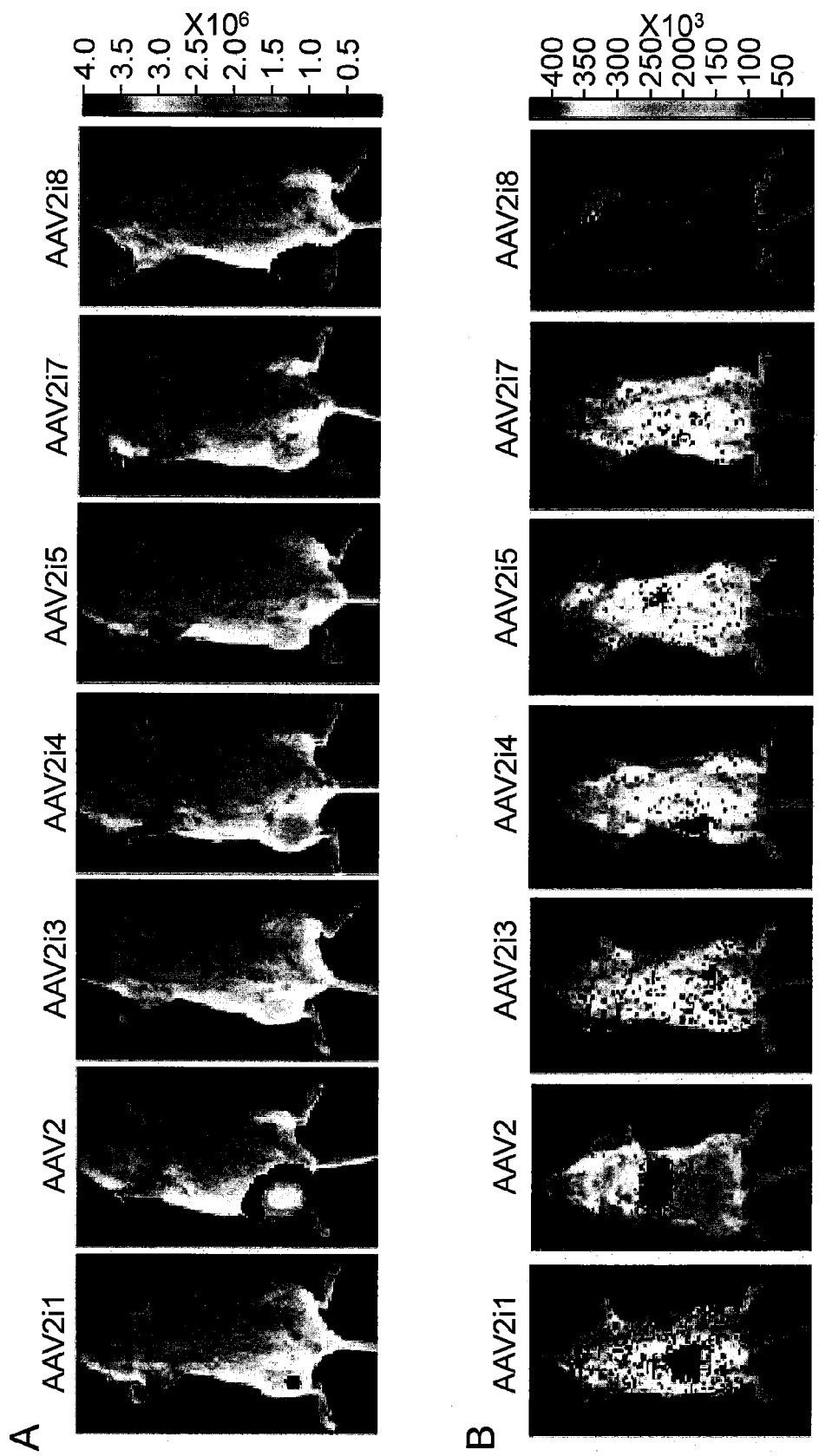
Figure 3:
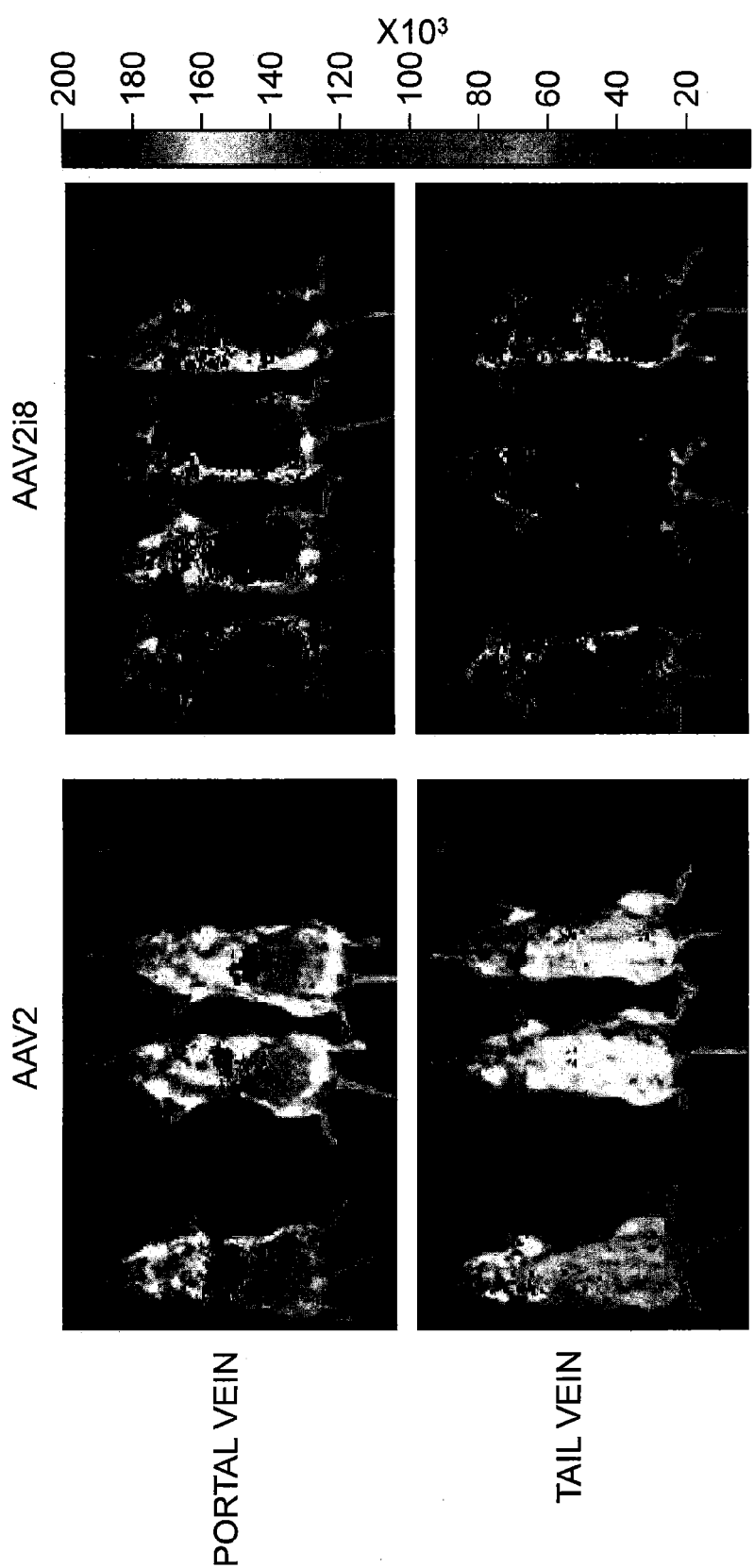
Figure 6A:
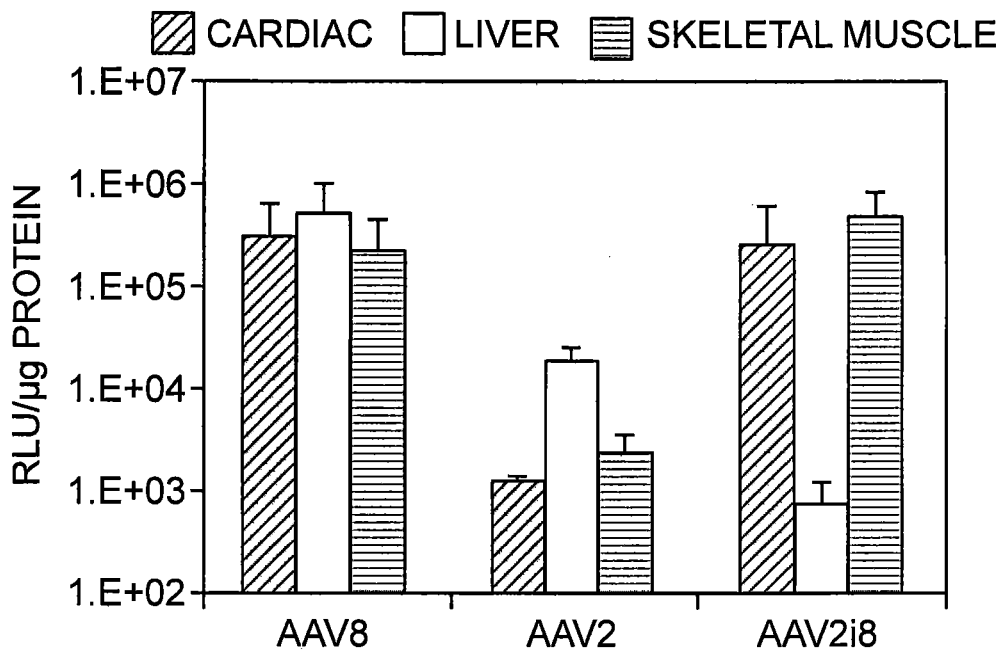
Figure 6B:
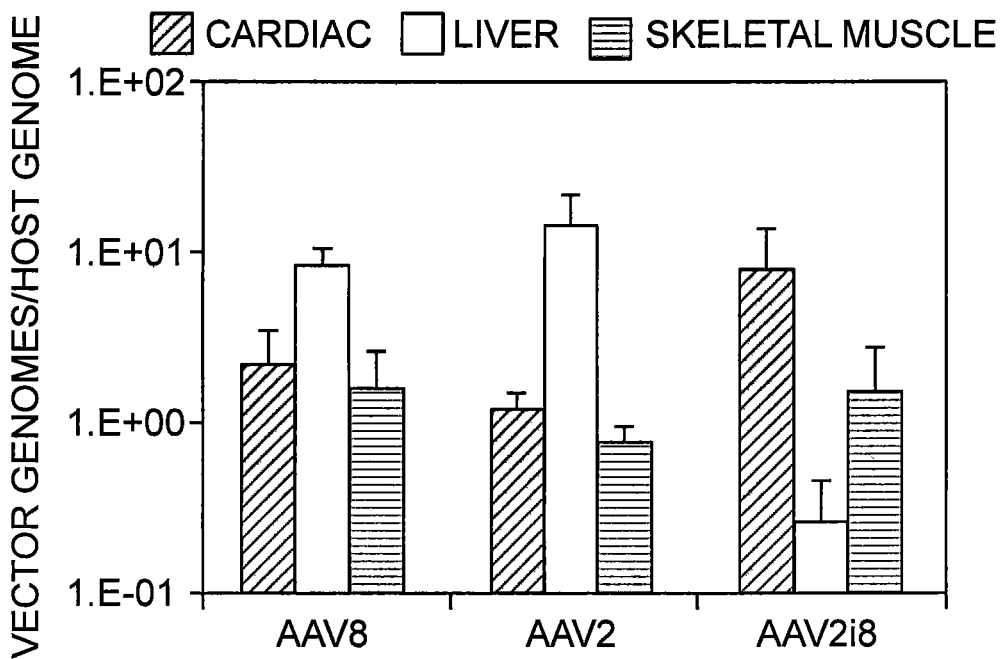
Figure 8:
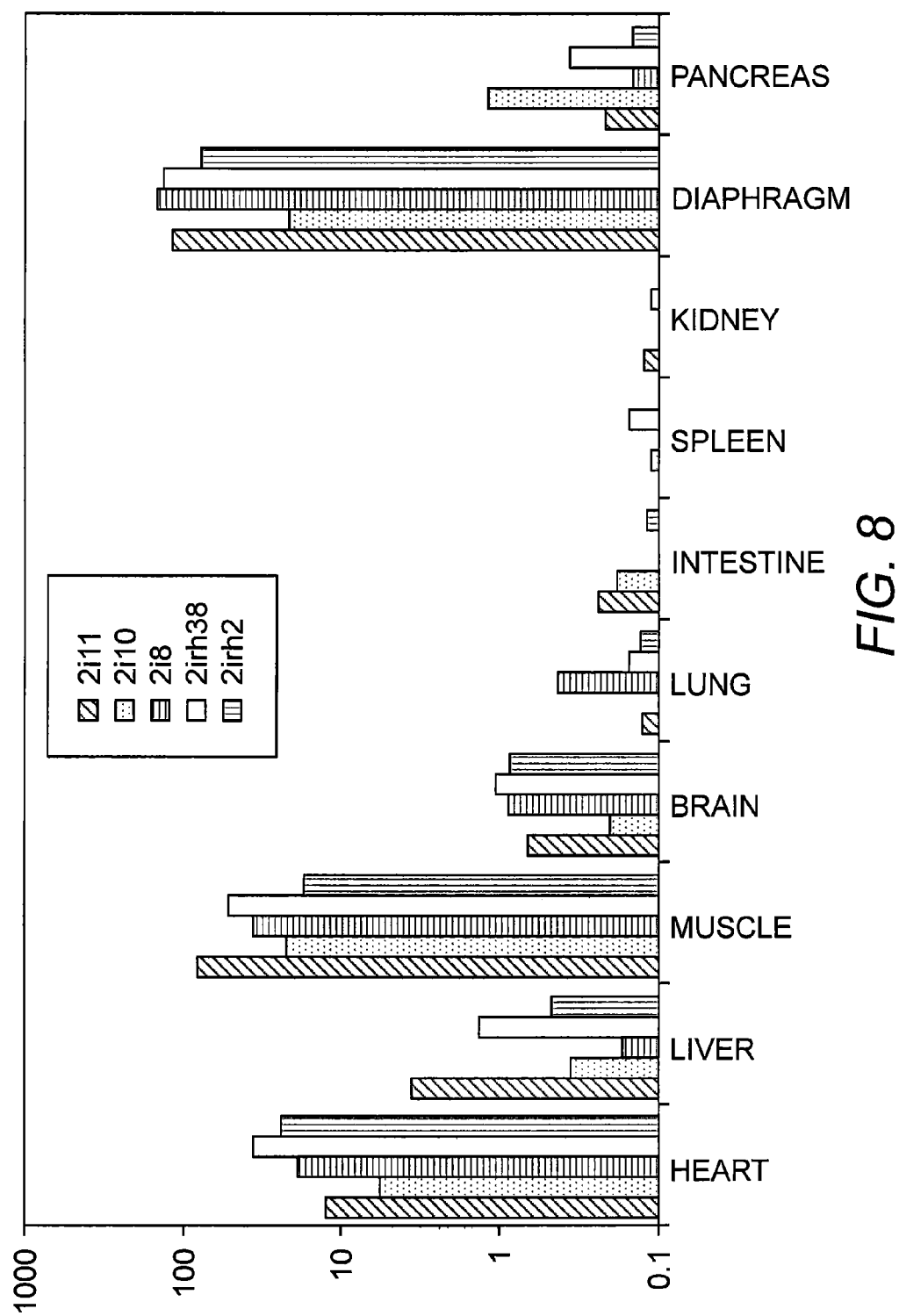
Figure 9:
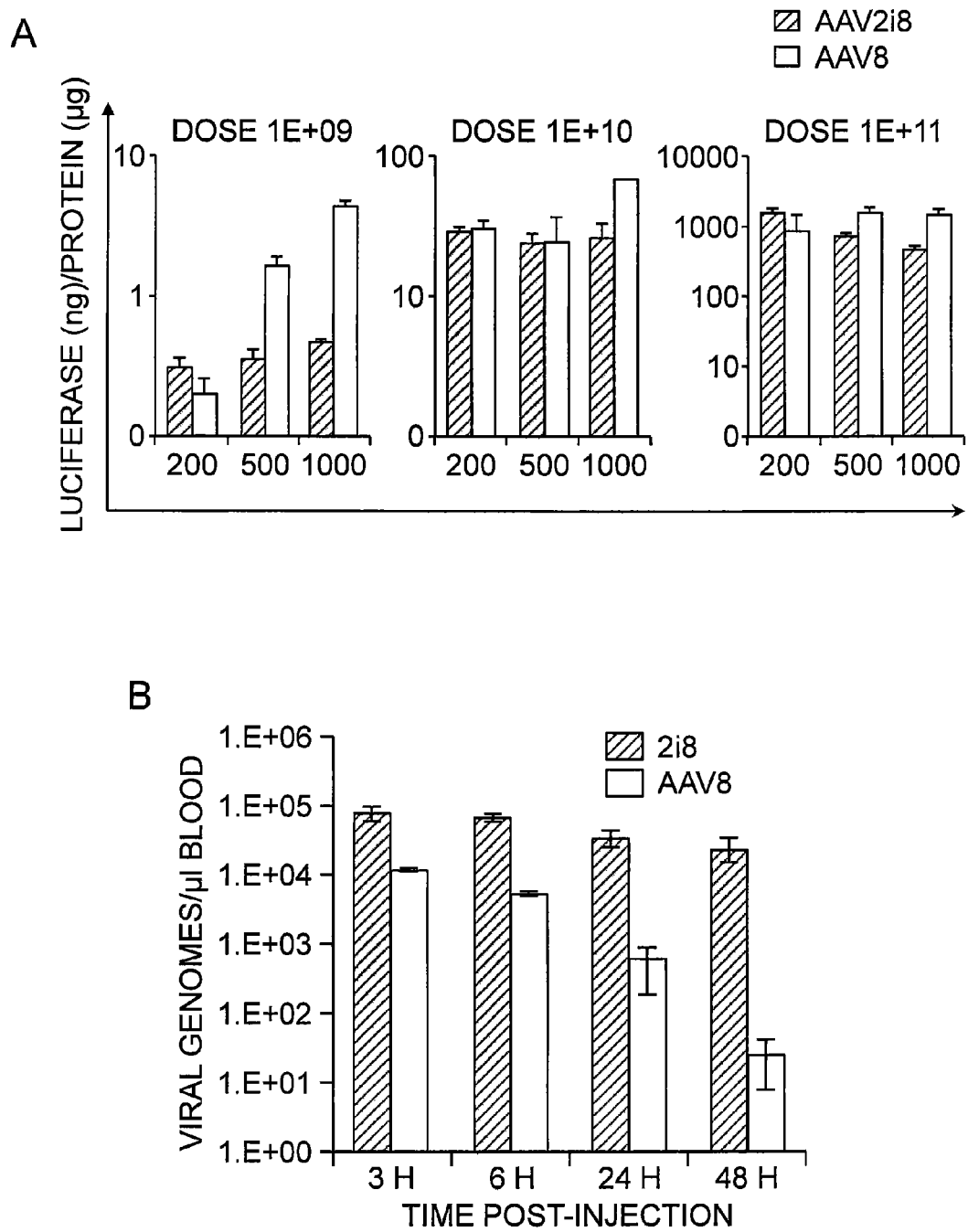
Figure 10:
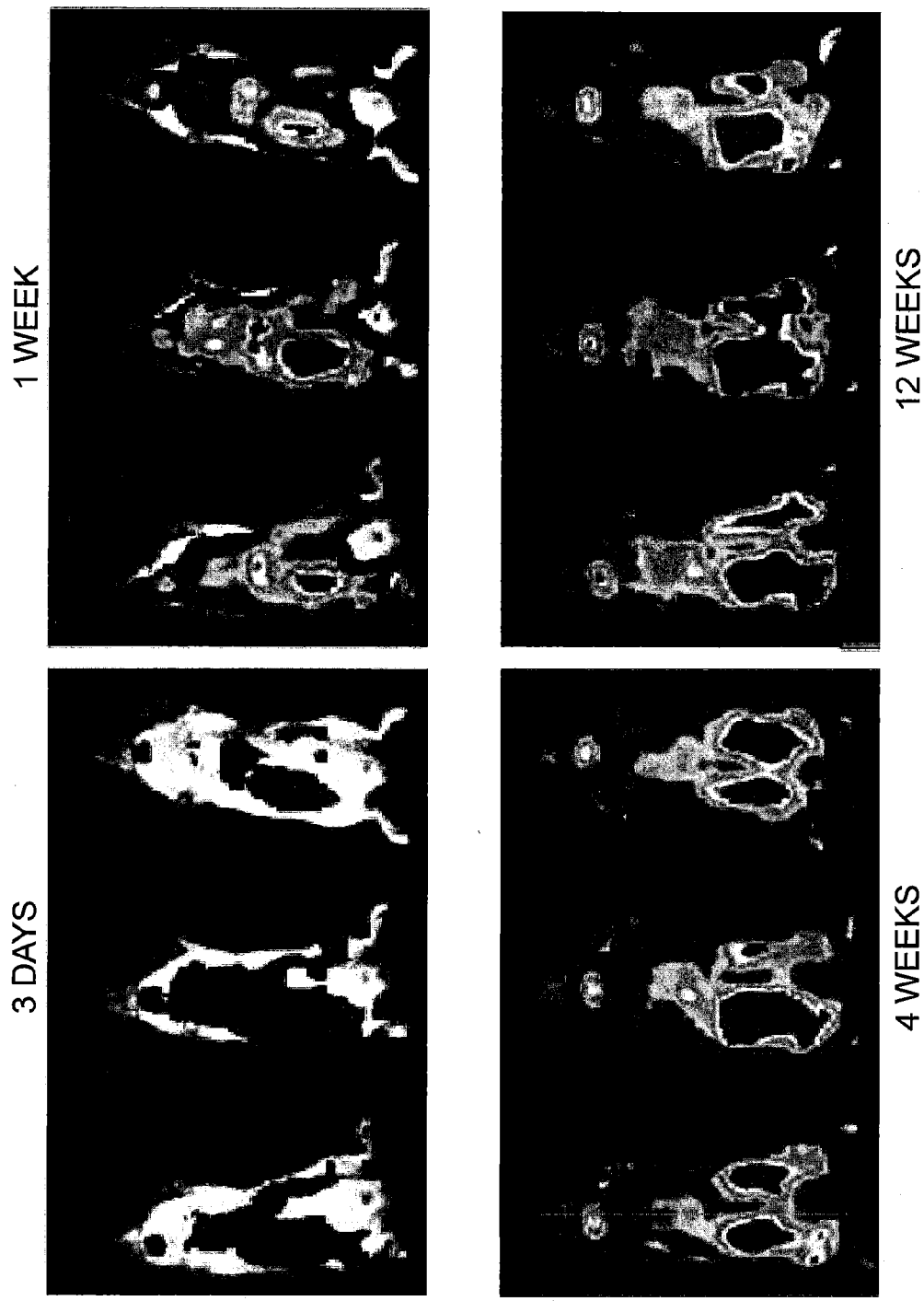

A striking exception in this regard is the AAV2i8 mutant, wherein a systemic transduction profile following intravenous administration is observed (FIG. 2, panel B). Further investigation led to the discovery that AAV2i mutants with a Q/NXXTXP (SEQ ID NO:164) motif demonstrate systemic tropism and superior transduction levels in contrast to parental AAV2 vectors and other AAV2i mutants in mice (Summarized in Table 5). Intriguingly, AAV2i8 and related mutants display an atypical transduction profile characterized by a switch in tropism from liver to muscle (FIGS. 6A, 6B, 8). Moreover, the latter transduction profile is also distinct from AAV8 and AAV9, which transduce multiple organs following systemic administration.

Example 11

Comparative Analysis of the Surface Map of AAV2i8 with AAV2 and AAV8 Capsids

A comparative analysis of the surface map of AAV2i8 with AAV2 and AAV8 capsids indicates that a unique footprint is generated upon incorporation of 585-QQNTAP-590 (SEQ ID NO:9) domain in the context of the AAV2 capsid template (data not shown). The resulting chimeric capsid surface can facilitate specific interactions with endogenous and/or alternative secondary receptors distinct from those mediated through AAV2-heparin interactions. In addition, the ability to significantly alter capsid surface topology by swapping a linear motif supports this approach for generating capsids with antigenic profiles distinct from parental serotypes (see Tables 6 and 7).

The foregoing is illustrative of the present invention, and is not to be construed as limiting thereof. The invention is defined by the following claims, with equivalents of the claims to be included therein.

That which is claimed is:

1. An adeno-associated virus (AAV) capsid protein, wherein the capsid protein comprises a modification resulting in the amino acid sequence SAQAQA (SEQ ID NO:10) at the amino acids corresponding to amino acid positions 585-590 (VP1 numbering) of the native AAV2 capsid protein.

2. An AAV capsid comprising the AAV capsid protein of claim 1.

3. A virus vector comprising:
   (a) the AAV capsid of claim 2; and
   (b) a nucleic acid comprising at least one terminal repeat sequence, wherein the nucleic acid is encapsidated by the AAV capsid.

4. A pharmaceutical formulation comprising the virus vector of claim 3 in a pharmaceutically acceptable carrier.

5. An adeno-associated virus (AAV) capsid protein, wherein the capsid protein comprises a modification resulting in the amino acid sequence QANTGP (SEQ ID NO:11) at the amino acids corresponding to amino acid positions 585-590 (VP1 numbering) of the native AAV2 capsid protein.

6. An AAV capsid comprising the AAV capsid protein of claim 5.

7. A virus vector comprising:
   (a) the AAV capsid of claim 6; and
   (b) a nucleic acid comprising at least one terminal repeat sequence, wherein the nucleic acid is encapsidated by the AAV capsid.

8. A pharmaceutical formulation comprising the virus vector of claim 7 in a pharmaceutically acceptable carrier.

* * * * *

UNITED STATES PATENT AND TRADEMARK OFFICE
CERTIFICATE OF CORRECTION

PATENT NO.        : 9,475,845 B2                                    Page 1 of 1
APPLICATION NO.   : 14/543459
DATED             : October 25, 2016
INVENTOR(S)       : Asokan et al.

It is certified that error appears in the above-identified patent and that said Letters Patent is hereby corrected as shown below:

Column 11, Line 49: Please correct "MV" to read -- AAV --
Column 11, Line 63: Please correct "MV TR sequence)," to read -- AAV TR sequence), --
Column 11, Line 63: Please correct "two MV TRs)," to read -- two AAV TRs), --
Column 12, Line 6: Please correct "non-MV" to read -- non-AAV --
Column 12, Line 19: Please correct "MV" to read -- AAV --
Column 12, Line 20: Please correct "terminal 1Q repeat" to read -- terminal repeat --
Column 14, Line 38: Please correct "575-60Q" to read -- 575-600 --
Column 14, Line 65: Please correct "MV" to read -- AAV --
Column 19, Line 66: Please correct "V 2Q. In"
                    to read -- V.
       In --
Column 24, Line 37: Please correct "13-barrel" to read -- β-barrel --
Column 26, Line 4: Please correct "ID 2Q NO:" to read -- ID NO: --
Column 26, Line 46: Please correct "NQ:86" to read -- NO:86 --
Column 29, Line 19: Please correct "cation 2Q now known" to read -- cation now known --
Column 30, Line 62: Please correct "other El a trans-" to read -- other E1a trans- --
Column 33, Line 14: Please correct "$α_r$," to read -- $α_1$ --
Column 33, Line 23: Please correct "µlatelet" to read -- platelet --
Column 33, Line 36: Please correct "RAP," to read -- IRAP, --
Column 38, Line 14: Please correct "RAP and TNFa" to read -- IRAP and TNFα --

Signed and Sealed this
Sixteenth Day of May, 2017

Michelle K. Lee
*Director of the United States Patent and Trademark Office*